US008889648B2

(12) United States Patent
Mitsutake et al.

(10) Patent No.: US 8,889,648 B2
(45) Date of Patent: Nov. 18, 2014

(54) NUCLEIC ACID HAVING AN ANTI-METABOLIC SYNDROME EFFECT

(75) Inventors: Susumu Mitsutake, Sapporo (JP); Kota Zama, Sapporo (JP); Yasuyuki Igarashi, Sapporo (JP); Tetsuya Yoshida, Sapporo (JP); Yoshikazu Tanaka, Sapporo (JP); Hiroshi Takemoto, Sapporo (JP)

(73) Assignees: National University Corporation Hokkaido University, Sapporo-Shi, Hokkaido (JP); Shionogi & Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 13/821,536

(22) PCT Filed: Sep. 21, 2011

(86) PCT No.: PCT/JP2011/005325
§ 371 (c)(1),
(2), (4) Date: May 20, 2013

(87) PCT Pub. No.: WO2012/039137
PCT Pub. Date: Mar. 29, 2012

(65) Prior Publication Data
US 2013/0231383 A1    Sep. 5, 2013

Related U.S. Application Data

(60) Provisional application No. 61/385,377, filed on Sep. 22, 2010.

(51) Int. Cl.
*C12N 15/113* (2010.01)
(52) U.S. Cl.
CPC .... *C12N 15/1137* (2013.01); *C12N 2310/3231* (2013.01); *C12Y 207/08* (2013.01); *C12N 2310/11* (2013.01); *C12N 2310/14* (2013.01)
USPC ...................................................... 514/44 A
(58) Field of Classification Search
None
See application file for complete search history.

(56) References Cited

U.S. PATENT DOCUMENTS

| 7,541,344 | B2 * | 6/2009 | Bhat et al. ............... 514/44 R |
| 2005/0255487 | A1 * | 11/2005 | Khvorova et al. ............ 435/6 |
| 2008/0113351 | A1 * | 5/2008 | Naito et al. .................. 435/6 |
| 2009/0264514 | A1 * | 10/2009 | Jiang et al. ............... 514/44 R |
| 2012/0315658 | A1 |  12/2012 | Mitsutake et al. |

FOREIGN PATENT DOCUMENTS

WO    WO 2011/036878    3/2011

OTHER PUBLICATIONS

Taylor et al. Drug Discovery Today 1999 vol. 4, pp. 562-567.*
Ding et al., "SMS overexpression and knockdown: impact on cellular sphingomyelin and diacylglycerol metabolism, and cell apoptosis", The Journal of Lipid Research, vol. 49, No. 2, Jan. 1, 2007, pp. 376-385, XP055015959.
Jepsen et al., "Locked nucleic acid: A potent nucleic acid analog in therapeutics and biotechnology", Oligonucleotides, Mary Ann Liebert, New York, NY, US, vol. 14, No. 2, Jan. 1, 2004, pp. 130-146, XP002395137.
Li et al., "Inhibition of sphingomyelin synthase (SMS) affects intracellular sphingomyelin accumulation and plasma membrane lipid organization", Biochimica and Biophysica Acta, Molecular and Cell Biology of Lipids, Elsevier, Amsterdam, NL, vol. 1771, No. 9, Sep. 17, 2007, pp. 1186-1194, XP022257634.
Milhas et al., "Sphingomyelin metabolism at the plasma membrane: Implications for bioactive sphingolipids", FEBS Letters, Elsevier, Amsterdam, NL, vol. 584, No. 9, May 3, 2010, pp. 1887-1894, XP027003147.
Mitsutake et al., "Dynamic Modification of Sphingomyelin in Lipid Microdomains Controls Development of Obesity, Fatty Liver, and Type 2 Diabetes", Journal of Biological Chemistry, vol. 286, No. 32, Aug. 12, 2011, pp. 28544-28555, XP055015955.
Mitsutake et al., "Sdudies of SMS2 or CerK deficiency mice and their relations to diet-induced obesity and mast cell activation," Chemistry and Physics of Lipids, Limerick, IR, vol. 163, Aug. 1, 2010, p. S4, XP027137784.
Mitsutake et al., "SMS2 deficiency prevents diet-induced obesity," Chemistry and Physics of Lipids, Limerick, IR, vol. 163, Aug. 1, 2010, p. S23, XP027137837.
Park et al., "Ceramide is a cardiotoxin in lipotoxic cardiomyopathy," The Journal of Lipid Research, vol. 49, No. 10, Jan. 1, 2008, pp. 2101-2112, XP055016038.
Summers et al., "A role for sphingolipids in producing the common features of type 2 diabetes, metabolic syndrome X, and Cushing's syndrome", Diabetes, vol. 54, No. 3, Mar. 1, 2005, pp. 591-602, XP055016182.
Tafess et al., "Both Sphingomyelin Synthases SMS1 and SMS2 are Required for Sphingomyelin Homeostasis and Growth in Human Hela Cells", Journal of Biological Chemistry, vol. 282, No. 24, Jan. 1, 2007, pp. 17537-17547, XP055015963.
Villani et al., "Sphingomyelin synthases regulate production of diacylglycerol at the Golgi", Biochemical Journal, vol. 414, No. 1, Aug. 15, 2008, p. 31, XP055015956.
Dong et al., "Adenovirus-mediated overexpression of sphingomyelin synthases 1 and 2 increases the atherogenic potential in mice", Journal of Lipid Research, vol. 47, 2006, pp. 1307-1314.

(Continued)

*Primary Examiner* — Tracy Vivlemore
(74) *Attorney, Agent, or Firm* — Ropes & Gray LLP; James F. Haley, Jr.; Yang Xu

(57) ABSTRACT

The problem of the present invention is to prove a medicament for decreasing body weigh, a medicament for decreasing visceral fat, a medicament for decreasing triglyceride in the liver, and a method for screening a medicament for ameliorating obesity and fatty liver. The problem is solved by a method comprising measuring an activity of a candidate material for inhibiting a sphingomyelin synthetase wherein if the candidate material has an activity for inhibiting a sphingomyelin synthetase, the candidate material is judged to have at least one function selected from the consisting of an anti-obesity drug, a drug for decreasing visceral fat, a drug for treating fatty liver and an agent for increasing adiponectin expression.

13 Claims, 28 Drawing Sheets

(56) References Cited

OTHER PUBLICATIONS

Elbashir et al., "Duplexes of 21-nucleotide RNAs mediate RNA interference in cultured mammalian cells", Nature, vol. 411, May 24, 2001, pp. 494-498.

Fire et al., "Potent and specific genetic interference by double-stranded RNA in *Caenorhabditis elegans*", Nature, vol. 391, Feb. 19, 1998, pp. 806-811.

Huitema, "Identification of a family of animal sphingomyelin synthases", The EMBO Journal, vol. 23, 2004, pp. 33-44.

Liu et al., "Macrophage Sphingomyelin Synthase 2 Deficiency Decreases Atherosclerosis in Mice", Circulation Research, (AHA), Jul. 9, 2009, 105:295-303.

Liu et al., "Sphingomyelin Synthase 2 Is One of the Determinants for Plasma and Liver Sphingomyelin Levels in Mice", Arteriosclerosis, Thrombosis, and Vascular Biology, (AHA), Mar. 12, 2009, 29:850-856.

Park et al., "Inhibition of Sphingomyelin Synthesis Reduces Atherogenesis in Apolipoprotein E-Knockout Mice", Circulation, (AHA), Nov. 15, 2004, 110:3465-3471.

Tafess et al., "The Multigenic Sphingomyelin Synthase Family", Journal of Biological Chemistry, Oct. 6, 2006, vol. 281, No. 40, pp. 29421-29425.

Ternes et al., "Sphingomyelin synthase SMS2 displays dual activity as ceramide phosphoethanolamine synthase", Journal of Lipid Research, vol. 50, 2009, 2270-2277.

Yamaoka et al., "Expression Cloning of a Human cDNA Restoring Sphingomyelin Synthesis and Cell Growth in Sphingomyelin Synthase-defective Lymphoid Cells", Journal of Biological Chemistry, Apr. 30, 2004, vol. 279, No. 18, pp. 18688-18693.

\* cited by examiner

Change in body weight from pre-administration

(N=3; unit =g)

|  | Day 10 |
|---|---|
| saline | + 5.1 |
| NC | + 5.2 |
| SMS2 (i11) | + 3.5 |
| SMS2 (i03) | + 3.5 |

Fig.16

SEQUENCE LISTING

<160> NUMBER OF SEQ ID NOS: 92

<210> SEQ ID NO 1
<211> LENGTH: 19
<212> TYPE: RNA
<213> ORGANISM: Artificial
<220> FEATURE:
<223> OTHER INFORMATION: SMS2-i6 sense strand

<400> SEQUENCE: 1
gcauuuucug uaucagaaa                                              19

<210> SEQ ID NO 2
<211> LENGTH: 19
<212> TYPE: RNA
<213> ORGANISM: Artificial
<220> FEATURE:
<223> OTHER INFORMATION: SMS2-i6 antisense strand

<400> SEQUENCE: 2
uuucugauac agaaaaugc                                              19

<210> SEQ ID NO 3
<211> LENGTH: 19
<212> TYPE: RNA
<213> ORGANISM: Artificial
<220> FEATURE:
<223> OTHER INFORMATION: SMS2-i7 sense strand

<400> SEQUENCE: 3
gucacuucug gugguauca                                              19

<210> SEQ ID NO 4
<211> LENGTH: 19
<212> TYPE: RNA
<213> ORGANISM: Artificial
<220> FEATURE:
<223> OTHER INFORMATION: SMS2-i7 antisense strand

<400> SEQUENCE: 4
ugauaccacc agaagugac                                              19

<210> SEQ ID NO 5
<211> LENGTH: 19
<212> TYPE: RNA
<213> ORGANISM: Artificial
<220> FEATURE:
<223> OTHER INFORMATION: SMS2-i8 sense strand

<400> SEQUENCE: 5
cuguuuuggu gguaccauu                                              19

<210> SEQ ID NO 6
<211> LENGTH: 19
<212> TYPE: RNA
<213> ORGANISM: Artificial
<220> FEATURE:
<223> OTHER INFORMATION: SMS2-i8 antisense strand

<400> SEQUENCE: 6
aaugguacca ccaaaacag                                              19

<210> SEQ ID NO 7
<211> LENGTH: 19
<212> TYPE: RNA
<213> ORGANISM: Artificial

```
<220> FEATURE:
<223> OTHER INFORMATION: SMS2-i104 sense strand

<400> SEQUENCE: 7
gggcauugcc uucauauau                                                  19

<210> SEQ ID NO 8
<211> LENGTH: 19
<212> TYPE: RNA
<213> ORGANISM: Artificial
<220> FEATURE:
<223> OTHER INFORMATION: SMS2-i104 antisense strand

<400> SEQUENCE: 8
auauaugaag gcaaugccc                                                  19

<210> SEQ ID NO 9
<211> LENGTH: 19
<212> TYPE: RNA
<213> ORGANISM: Artificial
<220> FEATURE:
<223> OTHER INFORMATION: SMS2-i105 sense strand

<400> SEQUENCE: 9
ggcuguuucu gagauacaa                                                  19

<210> SEQ ID NO 10
<211> LENGTH: 19
<212> TYPE: RNA
<213> ORGANISM: Artificial
<220> FEATURE:
<223> OTHER INFORMATION: SMS2-i105 antisense strand

<400> SEQUENCE: 10
uuguaucuca gaaacagcc                                                  19

<210> SEQ ID NO 11
<211> LENGTH: 19
<212> TYPE: RNA
<213> ORGANISM: Artificial
<220> FEATURE:
<223> OTHER INFORMATION: SMS2-i106 sense strand

<400> SEQUENCE: 11
ggugguggau uguccauaa                                                  19

<210> SEQ ID NO 12
<211> LENGTH: 19
<212> TYPE: RNA
<213> ORGANISM: Artificial
<220> FEATURE:
<223> OTHER INFORMATION: SMS2-i106 antisense strand

<400> SEQUENCE: 12
uuauggacaa uccaccacc                                                  19

<210> SEQ ID NO 13
<211> LENGTH: 19
<212> TYPE: RNA
<213> ORGANISM: Artificial
<220> FEATURE:
<223> OTHER INFORMATION: SMS2-i107 sense strand

<400> SEQUENCE: 13
ggauugucca uaacuggau                                                  19
```

```
<210> SEQ ID NO 14
<211> LENGTH: 19
<212> TYPE: RNA
<213> ORGANISM: Artificial
<220> FEATURE:
<223> OTHER INFORMATION: SMS2-i107 antisense strand

<400> SEQUENCE: 14
auccaguuau ggacaaucc                                                19

<210> SEQ ID NO 15
<211> LENGTH: 19
<212> TYPE: RNA
<213> ORGANISM: Artificial
<220> FEATURE:
<223> OTHER INFORMATION: SMS2-i108 sense strand

<400> SEQUENCE: 15
ccauaacugg aucacauau                                                19

<210> SEQ ID NO 16
<211> LENGTH: 19
<212> TYPE: RNA
<213> ORGANISM: Artificial
<220> FEATURE:
<223> OTHER INFORMATION: SMS2-i108 antisense strand

<400> SEQUENCE: 16
auaugugauc caguuaugg                                                19

<210> SEQ ID NO 17
<211> LENGTH: 19
<212> TYPE: RNA
<213> ORGANISM: Artificial
<220> FEATURE:
<223> OTHER INFORMATION: SMS2-i109 sense strand

<400> SEQUENCE: 17
gcacacgaac acuacacua                                                19

<210> SEQ ID NO 18
<211> LENGTH: 19
<212> TYPE: RNA
<213> ORGANISM: Artificial
<220> FEATURE:
<223> OTHER INFORMATION: SMS2-i109 antisense strand

<400> SEQUENCE: 18
uaguguagug uucgugugc                                                19

<210> SEQ ID NO 19
<211> LENGTH: 19
<212> TYPE: RNA
<213> ORGANISM: Artificial
<220> FEATURE:
<223> OTHER INFORMATION: CTR-i sense strand

<400> SEQUENCE: 19
uucuccgaac gugucacgu                                                19

<210> SEQ ID NO 20
<211> LENGTH: 19
<212> TYPE: RNA
<213> ORGANISM: Artificial
<220> FEATURE:
<223> OTHER INFORMATION: CTR-i antisense strand
```

```
<400> SEQUENCE: 20
acgugacacg uucggagaa                                              19

<210> SEQ ID NO 21
<211> LENGTH: 19
<212> TYPE: RNA
<213> ORGANISM: Artificial
<220> FEATURE:
<223> OTHER INFORMATION: SMS2-i3 sense strand

<400> SEQUENCE: 21 ggauggauauu gguugggu                                              19

<210> SEQ ID NO 22
<211> LENGTH: 19
<212> TYPE: RNA
<213> ORGANISM: Artificial
<220> FEATURE:
<223> OTHER INFORMATION: SMS2-i3 antisense strand

<400> SEQUENCE: 22
aacccaacca auaccaucc                                              19

<210> SEQ ID NO 23
<211> LENGTH: 19
<212> TYPE: RNA
<213> ORGANISM: Artificial
<220> FEATURE:
<223> OTHER INFORMATION: SMS2-i11 sense strand

<400> SEQUENCE: 23
ggcucuuucu gcguuacaa                                              19

<210> SEQ ID NO 24
<211> LENGTH: 19
<212> TYPE: RNA
<213> ORGANISM: Artificial
<220> FEATURE:
<223> OTHER INFORMATION: SMS2-i11 antisense strand

<400> SEQUENCE: 24
uuguaacgca gaaagagcc                                              19

<210> SEQ ID NO 25
<211> LENGTH: 23
<212> TYPE: DNA
<213> ORGANISM: Artificial
<220> FEATURE:
<223> OTHER INFORMATION: Adiponectin Fw primer

<400> SEQUENCE: 25
gtcagtggat ctgacgacac caa                                         23

<210> SEQ ID NO 26
<211> LENGTH: 19
<212> TYPE: DNA
<213> ORGANISM: Artificial
<220> FEATURE:
<223> OTHER INFORMATION: Adiponectin Rv primer

<400> SEQUENCE: 26
atgcctgcca tccaacctg                                              19

<210> SEQ ID NO 27
```

```
<211> LENGTH: 21
<212> TYPE: DNA
<213> ORGANISM: Artificial
<220> FEATURE:
<223> OTHER INFORMATION: insulin receptor Fw primer

<400> SEQUENCE: 27
cagctcgaaa ctgcatggtt g                                              21

<210> SEQ ID NO 28
<211> LENGTH: 22
<212> TYPE: DNA
<213> ORGANISM: Artificial
<220> FEATURE:
<223> OTHER INFORMATION: insulin receptor Rv primer

<400> SEQUENCE: 28
ggtgacatcc acctcacagg aa                                             22

<210> SEQ ID NO 29
<211> LENGTH: 23
<212> TYPE: DNA
<213> ORGANISM: Artificial
<220> FEATURE:
<223> OTHER INFORMATION: GLUT4 Fw primer

<400> SEQUENCE: 29
ctgtaacttc attgtcggca tgg                                            23

<210> SEQ ID NO 30
<211> LENGTH: 23
<212> TYPE: DNA
<213> ORGANISM: Artificial
<220> FEATURE:
<223> OTHER INFORMATION: GLUT4 Rv primer

<400> SEQUENCE: 30
aggcagctga gatctggtca aac                                            23

<210> SEQ ID NO 31
<211> LENGTH: 25
<212> TYPE: DNA
<213> ORGANISM: Artificial
<220> FEATURE:
<223> OTHER INFORMATION: HPRT Fw primer

<400> SEQUENCE: 31
ttgttgttgg atatgccctt gacta                                          25

<210> SEQ ID NO 32
<211> LENGTH: 21
<212> TYPE: DNA
<213> ORGANISM: Artificial
<220> FEATURE:
<223> OTHER INFORMATION: HPRT Rv primer

<400> SEQUENCE: 32
aggcagatgg ccacaggact a                                              21

<210> SEQ ID NO 33
<211> LENGTH: 19
<212> TYPE: DNA
<213> ORGANISM: Artificial
<220> FEATURE:
<223> OTHER INFORMATION: SMS2 Fw primer

<400> SEQUENCE: 33
```
tcaatggaga ctctcaggc                                          19

<210> SEQ ID NO 34
<211> LENGTH: 19
<212> TYPE: DNA
<213> ORGANISM: Artificial
<220> FEATURE:
<223> OTHER INFORMATION: SMS2 Rv primer

<400> SEQUENCE: 34
ccgctgaaga ggaagtctc                                          19

<210> SEQ ID NO 35
<211> LENGTH: 18
<212> TYPE: DNA
<213> ORGANISM: Artificial
<220> FEATURE:
<223> OTHER INFORMATION: human G3PDH Fw primer

<400> SEQUENCE: 35
ccttccgtgt ccccactg                                           18

<210> SEQ ID NO 36
<211> LENGTH: 19
<212> TYPE: DNA
<213> ORGANISM: Artificial
<220> FEATURE:
<223> OTHER INFORMATION: human G3PDH Rv primer

<400> SEQUENCE: 36
accctgttgc tgtagccaa                                          19

<210> SEQ ID NO 37
<211> LENGTH: 22
<212> TYPE: DNA
<213> ORGANISM: Artificial
<220> FEATURE:
<223> OTHER INFORMATION: mouse G3PDH Fw primer

<400> SEQUENCE: 37
caactcccac tcttccacct tc                                      22

<210> SEQ ID NO 38
<211> LENGTH: 23
<212> TYPE: DNA
<213> ORGANISM: Artificial
<220> FEATURE:
<223> OTHER INFORMATION: mouse G3PDH Rv primer

<400> SEQUENCE: 38
cttactcctt ggaggccatg tag                                     23

<210> SEQ ID NO 39
<211> LENGTH: 19
<212> TYPE: RNA
<213> ORGANISM: Artificial
<220> FEATURE:
<223> OTHER INFORMATION: SMS2-i1 sense strand

<400> SEQUENCE: 39
ggucacuugg aaagucaaa                                          19

<210> SEQ ID NO 40
<211> LENGTH: 19
<212> TYPE: RNA

```
<213> ORGANISM: Artificial
<220> FEATURE:
<223> OTHER INFORMATION: SMS2-i1 antisense strand

<400> SEQUENCE: 40
uuugacuuuc caagugacc                                                  19

<210> SEQ ID NO 41
<211> LENGTH: 19
<212> TYPE: RNA
<213> ORGANISM: Artificial
<220> FEATURE:
<223> OTHER INFORMATION: SMS2-i2 sense strand

<400> SEQUENCE: 41
ccggacuaca uccagauuu                                                  19

<210> SEQ ID NO 42
<211> LENGTH: 19
<212> TYPE: RNA
<213> ORGANISM: Artificial
<220> FEATURE:
<223> OTHER INFORMATION: SMS2-i2 antisense strand

<400> SEQUENCE: 42 aaaucggau guaguccgg                                                   19

<210> SEQ ID NO 43
<211> LENGTH: 19
<212> TYPE: RNA
<213> ORGANISM: Artificial
<220> FEATURE:
<223> OTHER INFORMATION: SMS2-i4 sense strand

<400> SEQUENCE: 43
gcagauuguu guugaucau                                                  19

<210> SEQ ID NO 44
<211> LENGTH: 19
<212> TYPE: RNA
<213> ORGANISM: Artificial
<220> FEATURE:
<223> OTHER INFORMATION: SMS2-i4 antisense strand

<400> SEQUENCE: 44
augaucaaca acaaucugc                                                  19

<210> SEQ ID NO 45
<211> LENGTH: 19
<212> TYPE: RNA
<213> ORGANISM: Artificial
<220> FEATURE:
<223> OTHER INFORMATION: SMS2-i5 sense strand

<400> SEQUENCE: 45
cauagagaca gcaaaacuu                                                  19

<210> SEQ ID NO 46
<211> LENGTH: 19
<212> TYPE: RNA
<213> ORGANISM: Artificial
<220> FEATURE:
<223> OTHER INFORMATION: SMS2-i5 antisense strand

<400> SEQUENCE: 46
aaguuuugcu gucucuaug                                                  19
```

```
<210> SEQ ID NO 47
<211> LENGTH: 21
<212> TYPE: DNA
<213> ORGANISM: Artificial
<220> FEATURE:
<223> OTHER INFORMATION: SMS2-i6 sense strand
<220> FEATURE:
<221> NAME/KEY: misc_feature
<222> LOCATION: (20)..(21)
<223> OTHER INFORMATION: n = dT

<400> SEQUENCE: 47
gcauuuucug uaucagaaan n                                              21

<210> SEQ ID NO 48
<211> LENGTH: 21
<212> TYPE: DNA
<213> ORGANISM: Artificial
<220> FEATURE:
<223> OTHER INFORMATION: SMS2-i6 antisense strand
<220> FEATURE:
<221> NAME/KEY: misc_feature
<222> LOCATION: (20)..(21)
<223> OTHER INFORMATION: n = dT

<400> SEQUENCE: 48
uuucugauac agaaaaugcn n                                              21

<210> SEQ ID NO 49
<211> LENGTH: 21
<212> TYPE: DNA
<213> ORGANISM: Artificial
<220> FEATURE:
<223> OTHER INFORMATION: SMS2-i7 sense strand
<220> FEATURE:
<221> NAME/KEY: misc_feature
<222> LOCATION: (20)..(21)
<223> OTHER INFORMATION: n = dT

<400> SEQUENCE: 49
gucacuucug gugguaucan n                                              21

<210> SEQ ID NO 50
<211> LENGTH: 21
<212> TYPE: DNA
<213> ORGANISM: Artificial
<220> FEATURE:
<223> OTHER INFORMATION: SMS2-i7 antisense strand
<220> FEATURE:
<221> NAME/KEY: misc_feature
<222> LOCATION: (20)..(21)
<223> OTHER INFORMATION: n = dT

<400> SEQUENCE: 50
ugauaccacc agaagugacn n                                              21

<210> SEQ ID NO 51
<211> LENGTH: 21
<212> TYPE: DNA
<213> ORGANISM: Artificial
<220> FEATURE:
<223> OTHER INFORMATION: SMS2-i8 sense strand
<220> FEATURE:
<221> NAME/KEY: misc_feature
<222> LOCATION: (20)..(21)
<223> OTHER INFORMATION: n = dT

<400> SEQUENCE: 51
```

-continued cguuuuuggu gguaccauun n                                              21

<210> SEQ ID NO 52
<211> LENGTH: 21
<212> TYPE: DNA
<213> ORGANISM: Artificial
<220> FEATURE:
<223> OTHER INFORMATION: SMS2-i8 antisense strand
<220> FEATURE:
<221> NAME/KEY: misc_feature
<222> LOCATION: (20)..(21)
<223> OTHER INFORMATION: n = dT

<400> SEQUENCE: 52
aaugguacca ccaaaacagn n                                              21

<210> SEQ ID NO 53
<211> LENGTH: 21
<212> TYPE: DNA
<213> ORGANISM: Artificial
<220> FEATURE:
<223> OTHER INFORMATION: SMS2-i104 sense strand
<220> FEATURE:
<221> NAME/KEY: misc_feature
<222> LOCATION: (20)..(21)
<223> OTHER INFORMATION: n = dT

<400> SEQUENCE: 53
gggcauugcc uucauauaun n                                              21

<210> SEQ ID NO 54
<211> LENGTH: 21
<212> TYPE: DNA
<213> ORGANISM: Artificial
<220> FEATURE:
<223> OTHER INFORMATION: SMS2-i104 antisense strand
<220> FEATURE:
<221> NAME/KEY: misc_feature
<222> LOCATION: (20)..(21)
<223> OTHER INFORMATION: n = dT

<400> SEQUENCE: 54
auauaugaag gcaaugcccn n                                              21

<210> SEQ ID NO 55
<211> LENGTH: 21
<212> TYPE: DNA
<213> ORGANISM: Artificial
<220> FEATURE:
<223> OTHER INFORMATION: SMS2-i105 sense strand
<220> FEATURE:
<221> NAME/KEY: misc_feature
<222> LOCATION: (20)..(21)
<223> OTHER INFORMATION: n = dT

<400> SEQUENCE: 55
ggcuguuucu gagauacaan n                                              21

<210> SEQ ID NO 56
<211> LENGTH: 21
<212> TYPE: DNA
<213> ORGANISM: Artificial
<220> FEATURE:
<223> OTHER INFORMATION: SMS2-i105 antisense strand
<220> FEATURE:
<221> NAME/KEY: misc_feature
<222> LOCATION: (20)..(21)
<223> OTHER INFORMATION: n = dT

<400> SEQUENCE: 56

-continued uuguaucuca gaaacagccn n                                        21

<210> SEQ ID NO 57
<211> LENGTH: 21
<212> TYPE: DNA
<213> ORGANISM: Artificial
<220> FEATURE:
<223> OTHER INFORMATION: SMS2-i106 sense strand
<220> FEATURE:
<221> NAME/KEY: misc_feature
<222> LOCATION: (20)..(21)
<223> OTHER INFORMATION: n = dT

<400> SEQUENCE: 57
ggugguggau uguccauaan n                                        21

<210> SEQ ID NO 58
<211> LENGTH: 21
<212> TYPE: DNA
<213> ORGANISM: Artificial
<220> FEATURE:
<223> OTHER INFORMATION: SMS2-i106 antisense strand
<220> FEATURE:
<221> NAME/KEY: misc_feature
<222> LOCATION: (20)..(21)
<223> OTHER INFORMATION: n = dT

<400> SEQUENCE: 58
uuauggacaa uccaccaccn n                                        21

<210> SEQ ID NO 59
<211> LENGTH: 21
<212> TYPE: DNA
<213> ORGANISM: Artificial
<220> FEATURE:
<223> OTHER INFORMATION: SMS2-i107 sense strand
<220> FEATURE:
<221> NAME/KEY: misc_feature
<222> LOCATION: (20)..(21)
<223> OTHER INFORMATION: n = dT

<400> SEQUENCE: 59
ggauugucca uaacuggaun n                                        21

<210> SEQ ID NO 60
<211> LENGTH: 21
<212> TYPE: DNA
<213> ORGANISM: Artificial
<220> FEATURE:
<223> OTHER INFORMATION: SMS2-i107 antisense strand
<220> FEATURE:
<221> NAME/KEY: misc_feature
<222> LOCATION: (20)..(21)
<223> OTHER INFORMATION: n = dT

<400> SEQUENCE: 60
auccaguuau ggacaauccn n                                        21

<210> SEQ ID NO 61
<211> LENGTH: 21
<212> TYPE: DNA
<213> ORGANISM: Artificial
<220> FEATURE:
<223> OTHER INFORMATION: SMS2-i108 sense strand
<220> FEATURE:
<221> NAME/KEY: misc_feature
<222> LOCATION: (20)..(21)
<223> OTHER INFORMATION: n = dT

```
<400> SEQUENCE: 61
ccauaacugg aucacauaun n                                              21

<210> SEQ ID NO 62
<211> LENGTH: 21
<212> TYPE: DNA
<213> ORGANISM: Artificial
<220> FEATURE:
<223> OTHER INFORMATION: SMS2-i108 antisense strand
<220> FEATURE:
<221> NAME/KEY: misc_feature
<222> LOCATION: (20)..(21)
<223> OTHER INFORMATION: n = dT

<400> SEQUENCE: 62
auaugugauc caguuauggn n                                              21

<210> SEQ ID NO 63
<211> LENGTH: 21
<212> TYPE: DNA
<213> ORGANISM: Artificial
<220> FEATURE:
<223> OTHER INFORMATION: SMS2-i109 sense strand
<220> FEATURE:
<221> NAME/KEY: misc_feature
<222> LOCATION: (20)..(21)
<223> OTHER INFORMATION: n = dT

<400> SEQUENCE: 63
gcacacgaac acuacacuan n                                              21

<210> SEQ ID NO 64
<211> LENGTH: 21
<212> TYPE: DNA
<213> ORGANISM: Artificial
<220> FEATURE:
<223> OTHER INFORMATION: SMS2-i109 antisense strand
<220> FEATURE:
<221> NAME/KEY: misc_feature
<222> LOCATION: (20)..(21)
<223> OTHER INFORMATION: n = dT

<400> SEQUENCE: 64
uaguguagug uucgugugcn n                                              21

<210> SEQ ID NO 65
<211> LENGTH: 21
<212> TYPE: DNA
<213> ORGANISM: Artificial
<220> FEATURE:
<223> OTHER INFORMATION: CTR-i sense strand
<220> FEATURE:
<221> NAME/KEY: misc_feature
<222> LOCATION: (20)..(21)
<223> OTHER INFORMATION: n = dT

<400> SEQUENCE: 65
uucuccgaac gugucacgun n                                              21

<210> SEQ ID NO 66
<211> LENGTH: 21
<212> TYPE: DNA
<213> ORGANISM: Artificial
<220> FEATURE:
<223> OTHER INFORMATION: CTR-i antisense strand
<220> FEATURE:
<221> NAME/KEY: misc_feature
<222> LOCATION: (20)..(21)
<223> OTHER INFORMATION: n = dT
```

-continued

```
<400> SEQUENCE: 66
acgugacacg uucggagaan n                                              21

<210> SEQ ID NO 67
<211> LENGTH: 21
<212> TYPE: DNA
<213> ORGANISM: Artificial
<220> FEATURE:
<223> OTHER INFORMATION: SMS2-i3 sense strand
<220> FEATURE:
<221> NAME/KEY: misc_feature
<222> LOCATION: (20)..(21)
<223> OTHER INFORMATION: n = dT

<400> SEQUENCE: 67
ggaugguauu gguuggguun n                                              21

<210> SEQ ID NO 68
<211> LENGTH: 21
<212> TYPE: DNA
<213> ORGANISM: Artificial
<220> FEATURE:
<223> OTHER INFORMATION: SMS2-i3 antisense strand
<220> FEATURE:
<221> NAME/KEY: misc_feature
<222> LOCATION: (20)..(21)
<223> OTHER INFORMATION: n = dT

<400> SEQUENCE: 68
aacccaacca auaccauccn n                                              21

<210> SEQ ID NO 69
<211> LENGTH: 21
<212> TYPE: DNA
<213> ORGANISM: Artificial
<220> FEATURE:
<223> OTHER INFORMATION: SMS2-i11 sense strand
<220> FEATURE:
<221> NAME/KEY: misc_feature
<222> LOCATION: (20)..(21)
<223> OTHER INFORMATION: n = dT

<400> SEQUENCE: 69
ggcucuuucu gcguuacaan n                                              21

<210> SEQ ID NO 70
<211> LENGTH: 21
<212> TYPE: DNA
<213> ORGANISM: Artificial
<220> FEATURE:
<223> OTHER INFORMATION: SMS2-i11 antisense strand
<220> FEATURE:
<221> NAME/KEY: misc_feature
<222> LOCATION: (20)..(21)
<223> OTHER INFORMATION: n = dT

<400> SEQUENCE: 70
uuguaacgca gaaagagccn n                                              21

<210> SEQ ID NO 71
<211> LENGTH: 21
<212> TYPE: DNA
<213> ORGANISM: Artificial
<220> FEATURE:
<223> OTHER INFORMATION: SMS2-i1 sense strand
<220> FEATURE:
<221> NAME/KEY: misc_feature
<222> LOCATION: (20)..(21)
```

```
<223> OTHER INFORMATION: n = dT

<400> SEQUENCE: 71
ggucacuugg aaagucaaan n                                          21

<210> SEQ ID NO 72
<211> LENGTH: 21
<212> TYPE: DNA
<213> ORGANISM: Artificial
<220> FEATURE:
<223> OTHER INFORMATION: SMS2-i1 antisense strand
<220> FEATURE:
<221> NAME/KEY: misc_feature
<222> LOCATION: (20)..(21)
<223> OTHER INFORMATION: n = dT

<400> SEQUENCE: 72
uuugacuuuc caagugaccn n                                          21

<210> SEQ ID NO 73
<211> LENGTH: 21
<212> TYPE: DNA
<213> ORGANISM: Artificial
<220> FEATURE:
<223> OTHER INFORMATION: SMS2-i2 sense strand
<220> FEATURE:
<221> NAME/KEY: misc_feature
<222> LOCATION: (20)..(21)
<223> OTHER INFORMATION: n = dT

<400> SEQUENCE: 73
ccggacuaca uccagauuun n                                          21

<210> SEQ ID NO 74
<211> LENGTH: 21
<212> TYPE: DNA
<213> ORGANISM: Artificial
<220> FEATURE:
<223> OTHER INFORMATION: SMS2-i2 antisense strand
<220> FEATURE:
<221> NAME/KEY: misc_feature
<222> LOCATION: (20)..(21)
<223> OTHER INFORMATION: n = dT

<400> SEQUENCE: 74
aaaucuggau guaguccggn n                                          21

<210> SEQ ID NO 75
<211> LENGTH: 21
<212> TYPE: DNA
<213> ORGANISM: Artificial
<220> FEATURE:
<223> OTHER INFORMATION: SMS2-i4 sense strand
<220> FEATURE:
<221> NAME/KEY: misc_feature
<222> LOCATION: (20)..(21)
<223> OTHER INFORMATION: n = dT

<400> SEQUENCE: 75
gcagauuguu guugaucaun n                                          21

<210> SEQ ID NO 76
<211> LENGTH: 21
<212> TYPE: DNA
<213> ORGANISM: Artificial
<220> FEATURE:
<223> OTHER INFORMATION: SMS2-i4 antisense strand
<220> FEATURE:
<221> NAME/KEY: misc_feature
```

```
<222> LOCATION: (20)..(21)
<223> OTHER INFORMATION: n = dT

<400> SEQUENCE: 76
augaucaaca acaaucugcn n                                              21

<210> SEQ ID NO 77
<211> LENGTH: 21
<212> TYPE: DNA
<213> ORGANISM: Artificial
<220> FEATURE:
<223> OTHER INFORMATION: SMS2-i5 sense strand
<220> FEATURE:
<221> NAME/KEY: misc_feature
<222> LOCATION: (20)..(21)
<223> OTHER INFORMATION: n = dT

<400> SEQUENCE: 77
cauagagaca gcaaaacuun n                                              21

<210> SEQ ID NO 78
<211> LENGTH: 21
<212> TYPE: DNA
<213> ORGANISM: Artificial
<220> FEATURE:
<223> OTHER INFORMATION: SMS2-i5 antisense strand
<220> FEATURE:
<221> NAME/KEY: misc_feature
<222> LOCATION: (20)..(21)
<223> OTHER INFORMATION: n = dT

<400> SEQUENCE: 78
aaguuuugcu gucucuaugn n                                              21

<210> SEQ ID NO 79
<211> LENGTH: 6246
<212> TYPE: DNA
<213> ORGANISM: Homo sapiens

<400> SEQUENCE: 79
atccactgtg aaatggagtt tcaaaatcac aagcttcttt cccacatgaa cataagacta      60
ggagcacata tggaagagta agttgaagg gaatttggat gatgatttgg caagatgctg     120
taagtggatt aggcaaggct gctaaagaga gacaggaaat ggctgtgtta gtgcttcgga    180
cctccgttag aagtagcagt tcatggtgtt gaaggtttgt tgttgaaaat accttcctga    240
ggcacctctt cattgtgctt attcttccca caacattgtg ccaagacact gtcaagcctg    300
ggcctgtcaa agcctgggat gtcaaaggcc tgggtctttc tcatcctgct gtaatgtatt    360
gatagctggg ggctctgcag aaggacaagg gaaggtggg atagtaacat cttttttgagg    420 gaagaattgg cttcctttct tgaaagtggt gaaggtacag catatagctg catggaagaa    480
acagtaatcg gatggctacc ttctacattt tgtattagga acaaagtcc attgtaagag    540 tccatgttga tcttggaaat agaaggattg aaaaagcta aatttccaca agaacaaga    600 acttgaccat ctcctttttg atctgaagac tagggacaa tggatatcat agagacagca    660
aaacttgaag aacatttgga aaatcaaccc agtgatccta cgaacactta tgcaagaccc    720
gctgaacctt ttgaagaaga aaacaaaaat ggcaatggta aacccaagag cttatccagt    780
gggctgcgaa aaggcaccaa aaagtacccg gactatatcc aaattgctat gcccactgaa    840
tcaaggaaca aatttccact agagtggtgg aaaacgggca ttgccttcat atatgcagtt    900
ttcaacctcg tcttgacaac cgtcatgatc acagttgtac atgagagggt ccctcccaag    960
```

```
gagcttagcc ctccactccc agacaagttt tttgattaca ttgatagggt gaaatgggca   1020
ttttctgtat cagaaataaa tgggattata ttagttggat tatggatcac ccagtggctg   1080
tttctgagat acaagtcaat agtgggacgc agattctgtt ttattattgg aactttatac   1140
ctgtatcgct gcattacaat gtatgttact actctacctg tgcctggaat gcatttccag   1200
tgtgctccaa agctcaatgg agactctcag gcaaaagttc aacggattct acgattgatt   1260
tctggtggtg gattgtccat aactggatca catatcttat gtggagactt cctcttcagc   1320
ggtcacacgg ttacgctgac actgacttat tgttcatca aagaatattc gcctcgtcac    1380
ttctggtggt atcatttaat ctgctggctg ctgagtgctg ccgggatcat ctgcattctt   1440
gtagcacacg aacactacac tatcgatgtg atcattgctt attatatcac aacacgactg   1500
ttttggtggt accattcaat ggccaatgaa aagaacttga aggtctcttc acagactaat   1560
ttcttatctc gagcatggtg gttccccatc tttattttt ttgagaaaaa tgtacaaggc    1620
tcaattcctt gctgcttctc ctggccgctg tcttggcctc ctggctgctt caaatcatca   1680
tgcaaaaagt attcacgggt tcagaagatt ggtgaagaca tgagaaatc gacctgagga    1740 gcaaaacaaa ggcatcagct cttacaccaa aagagttaac gctgtaacca aaggtatagt   1800
tttgtttttt attttaggag aactgactgg taaatgaaga aatggaccaa attttgtgta   1860
aacgattaga aagatgaaca aagtattgcc ctttgactgg ttttcttctt catcctgaga   1920
aagatacatt ctcttgcagc tcttcattca ttggtgacaa gccccaccc cgggacttta    1980 ctaatgagct tgttaaagag gtgccaaaga acatattcct cctttcttta ttctttctcc   2040
accaaaaccc tctacttcag aattttttca ggatatttt cagcccaagg tcagaagaat    2100
gtgttaatat tttaaataaa atatctggac atctacagcc actgtgtaaa tagaactgcc   2160
taatgttgag agtggttttt agcattaggt ttagcaaggg ggagatccgt ggggttgtgcg  2220 tcagctttgg gtgaattttg tttctaccct gtcacgggga agttcgggt tgagtccagg    2280 agtgcacact gctgctgcca cccaatgcgc tacatcac ttttttttgt tttgttttgt     2340
tttgttttta aagatcatt ttatcttaaa aaggaaagct gatccaagta aacacgaaag    2400
tatttgacac accccacaga ttttacatgt gtgtaaatgt ttcactttaa aatctctatg   2460
acagatacac aggaaacatg agatggtttc tgctaatgag tggcccttga gtacacactt   2520
agatgctgtc tgccctgtaa atttggatct ggtgccccag gcagtcaac tcttctagca    2580 caggctgaaa acacgtgtgt gtcaactgag gttcacacca cttggggaat gagcctgttt   2640
tctttccagg tcaggccctg gtgtgagatc aatttaggg ctcctaattg gagcacagaa    2700
atgtatttgg tcaaatttca ttgaaggtga tttcttcctt ttttctgttgt actttatgga  2760 aaaaccaaga tggaacctga agttaatgt atccttgctt ttagcaagag actcagtttc    2820
ttataactag tcctaaggac atatgccgca attgagtaat tttacttta ccctatgaaa    2880 ataacatggt gctgcactat aatatactct cggaatcagt gtgttagtta cagctataca   2940
gtgaaggggg ataactgttt ctaaatttct ttaaggtgat gccaaaaaat ggattaaaaa   3000
atctgatcag atttaatgtt accagattta gtgcattatt taatgctatt ggatcttttg   3060
gataattctt ggcttaattt cttagctact gaaggttaa tttgcaagac ttttaaaacc    3120
ttagaaaagt tttaaggttg caagttatc aacactgggg cagagggtgg agaggccaat    3180
gcgggtagaa ggaggcagtt atgtttatat tgaaggtgaa attttctttt catttagaat   3240
ggaaaacatc cccaaatgta tcattataaa ctagtcagcc ttgactacac aaaattgacc   3300
tttaagttgc ttgagaaaaa cacaatgcaa atcgttcaga agggtcaaca tcctttggtg   3360
```

```
ctaaaatctt gtgtatgttt tcagaatggc ttttctgta tgttatagaa taatcactaa    3420
aggaaaggta gttgaattta aagtcatgaa gcaagactct ttaattcagt tattttaaac    3480
aagaattaaa accccaaaca tccttggcag gctttgaagc acacagaatt ttctagtatt    3540
tcttattaaa tacaccaata ataaacatat acttagttta cctgatgagt ttagacataa    3600
ttctatataa tgttcgctta tattcattta ttaactagca acacttgtgc aagaacaagg    3660
tattctgctt gaaaacactg atttttaagt tcctgttgcc cgattgtaaa gaaaatcatc    3720
tgacacagaa gcctggtttt tgctctccta acactggtgt tttccttgag cctctaattc    3780
aaaataaaca aactgataca ccttacagcc ttattcatct gtgtctggat aactcacttt    3840
tcatctattg aataagaaaa agtgtttaaa cttaataaaa taaaaaattg tgcaccaatt    3900
actacagatc cttgaaacag taagccttgg attttagtca agtaatccag ttttttttta    3960
atttaaaaaa aaccatcacc ttttaaagaa ctttaaaaac acctgtgatg ccaatgtgga    4020
cattgccgct gccatgtctt tacacgcatg tgtcgtatag ctctgtcatc gagttgagga    4080
agtccatggt ttgcaaataa gggtggggga atcaaaattt caagatggaa aaataaaaca    4140
aatagtaaaa cccatttaca tgtaggaaag aaaagttgag cttcaaccca atgtgccact    4200
ttgatataaa acaagtatga tatatatata aactgaagat ataaaacaag tatgatcttg    4260
cctttgaaat cataaatgtt tggggtacct gttctttgcc agttaagata catatcttat    4320
tatctttgtt ttttttcaagt ctatgctcct gtttgaagct tttcctgtaa tttaggttgt    4380
ctgtgaaata cctataacat ataattccta tagagtatgc cacattttt ttctaactca    4440 tttcaaatga aattctctca gattctagtt tttgagcttg tccactagat ctgaaaataa    4500
agcatccttt cctgagtcca cttgaactaa ttgtgaattt gttacttaat ttactggcat    4560
cttgggaaac aagttttgct gtggcaggaa ggctgttttg agagtgagcg ttgagtctac    4620
tctggtttgt ggatgacatt gcattagggt tatttcctgt attaccagtg cccccttgtg    4680
gcaatatact ttatgacttg gaatgcaaac accacttta aaagcctgtt ttcaagtttt    4740
tgaaaggcat ttgttttctg ttgttttgcca ataatctgaa agtatcatgt gaaaggaatt    4800
attttaaaag cattttaaac ctttcccaaa ggtaaaatgt gctcagatta taggcacttg    4860
taattctaac cttgtatcca tttgatcaaa gaaaatttgt agaacatttt tacctctcat    4920
gatcacaatc attagtgtct ccctttataa cgacctatgt tttgtttact ttgaaacacc    4980
aaatttgttg tcttggtttt ttttacatga cagaactcat gcagtttctt ttttagttga    5040
aagttcacat cttgccccctt gaatagtttg aacattcctt tcttaattct tttttgtttt    5100
tgttttgcac tgtaaaactg atgaaaactt taagccaatc ttaatgcact agcctctgta    5160
gtgtaaggaa gtgtgagaag gagtttctta atgagtttac acgtttaaat caagcatatt    5220
ataagttata tgccatgtgt tgaaggcttt tctatttata tatataaga ttttagtat    5280 ttgttttag tgtccttgtg ttgcaataat ttaactcctt tgactcagtt gctgaaaata    5340
tttcttctat taagaagtgc tcttgacttc aacacccaaa cactgaaaat catgtcaatg    5400
ttacccaaag ataagttttt atacagatac acaccttata agttctgatt tatttttctta    5460 ctcattatgc tgtgttctaa ataaatcatg aatgagaaga gtgctttatt gtgaaattat    5520
ttaaaactgt cctttaaaag aaaagagga aacgatgaac aaaaactaat ctaattgcca    5580
agttagaatt cattatttaa tttacctcct atgcaatgat taatgctgca aaatgtatgg    5640
ttatgttacc gtatattcac aaaagaaata ttattacaag gtttcagagg tagccaattg    5700
```

```
cattcttttg gaaatttact gtactgtttc aatgtgttaa gtgccttgtt gtaaagtaaa    5760
attttaagtc tagattcatt attttcctga catatatttt tcattatgat atctactgta    5820
tgctattgtg atagttttat gaaatgctta catttttaatc aaatatgtaa atttcagaag   5880 ctctttttc ctacccacca gtaccttaat cattggttta tcacattgga ttcaaattca     5940
ggttcctttt ttgataaaga ggaaatttgt tttccatgct gtgattttg tgtttgtaaa     6000 catttcagga ggaatttagg agtgtaacta tagtttatac ttctataatg ttgtcttaca    6060
tttacatttt taagtgccta attgttaaaa ctgatttatg tttctcttct aaagaggata    6120
tgtgtacttg gtttctaatc tctttggttt tgcttttttaa aaaatgcaag agcctatact   6180
ttgtatttac ctaataaacc acagtgacat caacagtctt ttcaaaatta aaaaaaaaa    6240 aaaaaa                                                               6246

<210> SEQ ID NO 80
<211> LENGTH: 5791
<212> TYPE: DNA
<213> ORGANISM: Mus musculus

<400> SEQUENCE: 80
tgtctgtcct cggttgaagc ttcttggatg catgaccacc aggctaggag cacatgccgg     60
aatgttagat atgttcagtc aactaggttg gagtgggtag acgccagcca tcgctgcgtg   120
agggcctggg tatcttcctc aggagggatc catggtagag agagttgctc ttggattcat   180
cttgctgagg gtcctcctca ggagttcatt cttcccacgg cctttcctaa aggcaccgaa   240
gagagcattg tcaggccag aggaacgctg gcttcctcac tccctctact agggtcttgg   300
tacttggaga gactttcaca gggacaagag gaagaaggaa caataacatc atctgtggga   360
aagagaacca gcttccttgt ggtgactaca cagcaggttg ttgtatggaa ggactaggaa   420
ccagcaggcc accgactaca tttcgtatca gcacacatca tcagttctaa gagtccatgt   480
tgatctcgca agtagaagga tttaaaagag aaaggttccc acagaaacca agaaccttac   540
catctccttt agccctggag ggtggcggac aatggatatc atagagacag caaaacttga   600
aggtcacttg gaaagtcaaa ccaacgactc caccaacact tacacaagcc ccaccgaagc   660
tgtagaggaa gagggcaaaa atggcaaggg caaacccaag accttatcca acgggttacg   720
aaagggtgcc aaaaaatacc cggactacat ccagatttcc atgcccaacg actccaagaa   780
caagtttccc ctggagtggt ggaaaacagg catcgccttt gtgtatgcgc tcttcaacct   840
catcctgaca accgtcatga tcaccgtcgt gcacagagg gtccctccca aggagctcag    900
ccctccgctc ccagacaagt ttttgatta cttcgaccgg gtcaaatggg cattttctgt   960
atcagaaata aacgggatgg tattggttgg gttatggatc acccagtggc tctttctgcg   1020
ttacaagtca atagtggggc gcagattctt cttcatcatg ggaactttat acctgtatcg   1080
ctgtataact atgtatgtca ctacgttacc tgtgcccgga atgcacttcc agtgtgctcc   1140
caagctcaat ggagactctc aggcaaaaat acagcggatt ctccggctga tttctggcgg   1200
gggactgtct atcacgggat ctcacatcct gtgcggagac ttcctcttca gcggccacac   1260
tgtcgtgctc acacttactt acttgttcat caaagaatat tcacctcgtc acttctggtg   1320
gtatcacttg gtctgctggc tgctgagtgc ggctgggatc atctgcattc tcgtagcgca   1380
tgaacactat accgtggacg tcatcattgc ttactatatc acaacacggc tgttttggtg   1440
gtaccattcc atggccaacg aaaagaactt gaaggtctct tcccagacga acttcttgtc   1500
tcgggcttgg tggttcccca tcttctactt ttttgagaag aatgtgcaag gctcaattcc   1560
```

```
ttgctgcttt tcctggccgc tgtcctggcc ccctggctgc ttcaagtcat cgtgcagaaa    1620
gtattcccgg gtccagaaga tcggggagga taatgagaag tctacctgag ctgccaaccc    1680
ggcagccgct ctcacaccaa aagagtccgt gctgcaaccg aaggcacgtg cggctttata    1740
tttattttca gagaactgac tggtaaaatg aagtggacca aatttttatgc aaaagattgg    1800 agcgatgaag tattaccttt ggcttttttt tattcatccc aagaaacata tattttcctg    1860
cagctcttcg ttcattgatg acaaagcccc cacactggag ttctgaagag gtggcaaaga    1920
acacgccgag cctctcctcg ccttccttca cttccacgtt cttttccagat tgcttttttt    1980 ctcccttcaa ggtcagaaga gtttgctaac gttttgaata aaatgtctgg atatatacag    2040
ccactgtgta aatacagtca gttgatggca gtgggttttc accacagagc ttagtaaggg    2100
gcagcctgca ggtggggcaa ggtcattagg gtgatgtctg gtgtccctc ccctcccccg    2160 ccacccatta tgcatgactt ttactctttt tggggaggg gggttggctt ttggttttc    2220 aagacagggt ttctctgtgt agccttggct gtcctggaac tcactctgaa gaccacaccc    2280
ggcctctttt tttttttttt ttttaaacct ggtaatttta gttttaaag aaagagtatt    2340 gcaaggtcat gtgaaagaga cacacccatg gatattttt ccctgtgtgg ggattttcc    2400 actttcaagt gtccgtggca gataaccggc aggctccggg cttttcctgc tatacccgtt    2460
agatgctgcc tgccgggagc ccaaggcttg ttaaccgcac cagcacaggc tgaaaccagt    2520
gtgaacagat gctcacactg gagagcaagc ttgtgctctc tgctagcttg ggccctgccg    2580
tgccatgccg tgatgccgtt acttattgga ccctagagaa acatttgggc acattccatg    2640
aaaacagctt cttttatt taatatcgtg tgtctcggga atgcaagatg gatcccaaag    2700
gttttactgt ttccctgcct tttagcaaga cccccccccc cagcgctcct tagggcgtgc    2760
accaccgctg agcaactcac ttcaccctgt gcacataaca cgcggtgctg cccttgaaca    2820
tgtccctggc atcagctctt aacctcagcc atgtaggaat gagggacaac tgttatctca    2880
tgtgaaaaga tgggtctcta agatctggtg ggtttaagaa catcggactc agttagaagg    2940
ttactcagtg ctgggatatc atagtccttg cctttggttg agatctactg aaagattagt    3000
ttgtggaact tgtagaaaaa cttctaagga ttcacagcat gggagcagcc agtggaaggg    3060
gtggttacat tctcatgggt atggcataga gaacatccct gggttcgtcc ctgtaagcta    3120
gtcggccttg attgtttaaa attaaacttt aaattgcttg ggagaaaaaa aaagcacaa    3180 tacagatgtg ttcagaaggg ccattgtctt ctggtgctat aattctgtgt gtgtgtttca    3240
gagggtctcg ttttctgtgt tactgggtgg gtaaaggata ggatgctaaa cccaaagaca    3300
cgagcataaa aatctaagtc tgactatcct cacaagagca gagaccctaa gtgtctttgg    3360
cagactttga aatgcaggga ctttttttt tcaagtattt ttatcgagta agccaataat    3420
aaattcatac ccagtttacc ttgtactaga caattcggta caactcctca cgtgttcatt    3480
tcctcagctc tgtggaaagc tctgctccga acactagttt accttcaggg tctgattatg    3540
agagaatcat ttggcgctga agcctggcct ttgctctgcg agtctctcac tgaaacaaaa    3600
cactgaaaca aaacacctga aaagccttat ccagcctggc taggattctc catgattctt    3660
caaccgagga aaatgcttag acattgttac atttcatgtt gattgttggg aacccttcaa    3720
acagaaaact ttgcatttag tcaggtaaac caggctgttg gaaacaatac catcactttc    3780
ttaaggtttg aaaatacccca tgagcccgt gtggaccctg ctgttccctg ttcttgtagt    3840
agctgtgatt cctaataggt accgatgggg atgcaagatg acaactcatt gcagtgcagg    3900
```

| | |
|---|---|
| aaagtaagac ttcctttaag atggtctcat ctcactgtgt agcccagatt ggcctccaac | 3960 |
| cttcagccct cctgtatcag cccctgggt gctgggattg caggtgtgtt tccatgccta | 4020 |
| cccaggcaca gcaggacatg gtaccagcac cttttctttg cccattaaga tgcagatttt | 4080 |
| acccattaag tgtgggtaag gcgcaagcgg gcgcctgtgc tcctgttgga aggttttccc | 4140 |
| cataatatag agcttctgga aaacgtccac aaatatagaa cacacatgtt tttcctgaac | 4200 |
| cttcccaatg ggactggagt tctctgagac tccgggtttg agctcctcca ctagatcggg | 4260 |
| aaaaggaggt atccttcccc cagtgacccc tgagctaatt ttgactgtct tttgggttgc | 4320 |
| tgtcatcaca ggaagcagct ttttgctggg gacacaaggt tggctgagag tcagctcttg | 4380 |
| caatccctgg gcaggtttgt ggccatccat cccttgctgt gttgccagcg cccccttgtg | 4440 |
| gtgatatgtc atgtctgaaa tccaaatgcc actttaaaaa tatattttca aggtttctct | 4500 |
| aaagtttatc tgttgggcct tttgttgttg ctgttttcag ggttttttgc caaaagttga | 4560 |
| aattcccatg ggaaaggagc tattttaaag acattcttat ccttcccaaa gggaaagttc | 4620 |
| tcagaatttg agtcaaagaa agttgaaggt cacatttacc tcttatgtca caatcattcg | 4680 |
| tgtctggccc atagctacag actttgttta cttcaaaacc caaagtcagc tgtctcattt | 4740 |
| ttatttatgt gccagaactc atcatttcac ttgtaattga aaggtcttac cttgttccat | 4800 |
| aaaatatttt aaactctttg ttaaatgttt tgatttata ctataaaact gatttaaaaa | 4860 |
| ttaagccagt cttaacacac tcaccctgtc tgtagtgtaa ggaagtgtga gaaggaagtt | 4920 |
| cttttttatt gtttgtttgt ttgtttgttt gtttgtttga gacagggttt ctttgtgtag | 4980 |
| ccctggctgt cctggaactc acgcagtaga ccaggctggc cttgaactca gaaatccgcc | 5040 |
| tgcctctgcc tctgcctctg cctcctgaat gctaggatta aaggcatatg ccaccaccgc | 5100 |
| ctgacgagaa ggaatttctt aataaatgag tttacatgtc taaatcaagt gtaagttata | 5160 |
| tgcgttgtgt tggaaccttt tctacgttta tgtataaaga tttcttatat tattattttt | 5220 |
| aatgccattg cgttgcaata atttagctcc tgactcattt gacaaaaata catcttttat | 5280 |
| gaagaagtac tcttgacttt gatatctgta cactgaaaat catgtcagaa gtacccaaag | 5340 |
| ataagttttt atacagatag acgcttcgta agcgctggct tgttacccac taactaactg | 5400 |
| tactgtgttc tcaatgaatc atgaaagaca agagtgggtc actgtagaat tattttaaac | 5460 |
| tgtcctttaa aagagaagaa actataagct aatctagttg ccaagtagga attccttatt | 5520 |
| taatttacct cctatgcaat gattaatgct gcgaaatgta tggttaataa gttacagtat | 5580 |
| attcacagaa gaaatatctt tccaaggtgt aagaagcagc cagttgcatt cttttggaaa | 5640 |
| tttactatac tgtttcaatg tgttaagtgc cttgttgtaa agtaaaattt taagtctcga | 5700 |
| gttcattatt ttcctgacct atattttca ttatgattat ctactgtgtg ctgttgtaat | 5760 |
| cattttatta aatgcttaca ttttaatcaa a | 5791 |

```
<210> SEQ ID NO 81
<211> LENGTH: 13
<212> TYPE: DNA
<213> ORGANISM: Artificial
<220> FEATURE:
<223> OTHER INFORMATION: SMS2-13-003
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid
```

<400> SEQUENCE: 81
tgataccacc aga                                                          13

<210> SEQ ID NO 82
<211> LENGTH: 13
<212> TYPE: DNA
<213> ORGANISM: Artificial
<220> FEATURE:
<223> OTHER INFORMATION: SMS2-13-006
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 82
tgcagatgat ccc                                                          13

<210> SEQ ID NO 83
<211> LENGTH: 13
<212> TYPE: DNA
<213> ORGANISM: Artificial
<220> FEATURE:
<223> OTHER INFORMATION: SMS2-13-007
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 83
cgtgttgtga tat                                                          13

<210> SEQ ID NO 84
<211> LENGTH: 13
<212> TYPE: DNA
<213> ORGANISM: Artificial
<220> FEATURE:
<223> OTHER INFORMATION: SMS2-13-008
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 84
acttgtctgg gag                                                          13

<210> SEQ ID NO 85
<211> LENGTH: 13
<212> TYPE: DNA
<213> ORGANISM: Artificial
<220> FEATURE:
<223> OTHER INFORMATION: SMS2-13-009
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)

<223> OTHER INFORMATION: Locked nucleic acid

<400> SEQUENCE: 85
agaggaagtc tcc                                                            13

<210> SEQ ID NO 86
<211> LENGTH: 13
<212> TYPE: DNA
<213> ORGANISM: Artificial
<220> FEATURE:
<223> OTHER INFORMATION: SMS2-13-010
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 86
agatggggaa cca                                                            13

<210> SEQ ID NO 87
<211> LENGTH: 13
<212> TYPE: DNA
<213> ORGANISM: Artificial
<220> FEATURE:
<223> OTHER INFORMATION: SMS2-13-011
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 87
agtctccatt gag                                                            13

<210> SEQ ID NO 88
<211> LENGTH: 13
<212> TYPE: DNA
<213> ORGANISM: Artificial
<220> FEATURE:
<223> OTHER INFORMATION: SMS2-13-012
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 88
ccagaagtga cga                                                            13

<210> SEQ ID NO 89
<211> LENGTH: 13
<212> TYPE: DNA
<213> ORGANISM: Artificial
<220> FEATURE:
<223> OTHER INFORMATION: SMS2-13-014
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 89
ttgcctgaga gtc                                                            13

<210> SEQ ID NO 90
<211> LENGTH: 13
<212> TYPE: DNA
<213> ORGANISM: Artificial
<220> FEATURE:
<223> OTHER INFORMATION: SMS2-13-017
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 90
aagttttgct gtc                                                            13

<210> SEQ ID NO 91
<211> LENGTH: 13
<212> TYPE: DNA
<213> ORGANISM: Artificial
<220> FEATURE:
<223> OTHER INFORMATION: SMS2-13-019
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 91
ttgaagcagc cag                                                            13

<210> SEQ ID NO 92
<211> LENGTH: 13
<212> TYPE: DNA
<213> ORGANISM: Artificial
<220> FEATURE:
<223> OTHER INFORMATION: SMS2-13-020
<220> FEATURE:
<221> NAME/KEY: misc_feature
<222> LOCATION: (1)..(3)
<223> OTHER INFORMATION: Locked nucleic acid
<220> FEATURE:
<221> NAME/KEY: misc_feature
<222> LOCATION: (12)..(13)
<223> OTHER INFORMATION: Locked nucleic acid

<400> SEQUENCE: 92
gcagcaagga att                                                            13

NUCLEIC ACID HAVING AN ANTI-METABOLIC SYNDROME EFFECT

CROSS-REFERENCE TO RELATED APPLICATIONS

This application is a national stage application under 35 U.S.C. §371 of International Application PCT/JP2011/005325, filed on Sep. 21, 2011, which application claims priority from U.S. Provisional Patent Application 61/385,377, filed Sep. 22, 2010. The disclosure of each of these referenced applications is incorporated by reference herein in its entirety. International Application PCT/JP2011/005325 was published under PCT Article 21(2) in English.

TECHNICAL FIELD

The present invention relates to a novel usage of SMS2. More specifically, the present invention relates to a pharmaceutical composition for treating a metabolic syndrome, which uses SMS2.

BACKGROUND ART

The induction of obesity has been known to be involved in an action of accelerating eating via proteins that are expressed in the hypothalamus such as neuropeptide Y5 receptor, or melanocortin receptor, an action of accelerating the synthesis of fatty acids via acyl-CoA carboxylase (ACC) or the like. Currently, as an anti-obesity drug, a neuropeptide Y5 receptor antagonist, a melanocortin receptor antagonist and an ACC inhibitor or the like have been developed. However, to date, an effective anti-obesity drug has not been found.

Fatty liver is a disease, which a neutral fat accumulates in the liver, and obesity are deemed as a major cause of developing it. However, similarly to an anti-obesity drug, an effective drug for treating fatty liver has not been found to date. In addition, regarding diabetes which is deemed as a representative example of a metabolic syndrome and which is deemed as a fundamental cause of lifestyle related diseases such as obesity or circulatory system diseases, sulfonylurea drugs, biguanides, alphaglucosidase and azolidine derivatives and the like have been developed. However, problems for side effect and efficacy thereof exist. Therefore, a more effective drug for treatment is expected to be developed.

A sphingomyelin synthetase (SMS) is an enzyme which synthesizes sphingomyelin(SM), a sphingolipid most abundant in a cell membrane, and plays an important role in cell death and survival (see, NPLs 1 and 2). SMS was identified in 2004, and are known to be present as two kinds, SMS1 and SMS2. SMS1 is known to be expressed in the Golgi body and be involved in de novo synthesis of SM. On the other hand, SMS2 is expressed in the Golgi body and cell membrane and unknown for its physiological function in detail (see, NPL 3) and merely suggested in NPLs 4-6 for the possibility of involving in arteriosclerosis.

To date, methods for ameliorating a metabolic syndrome by using neutral fat metabolism/absorbance inhibitors or inhibiting agents, agents for accelerating neutral fat metabolism or the like have been attempted. Specifically, these are drugs for ameliorating hyperlipidemia and type II diabetes by synthetic ligands of intranuclear receptor PPARs, drugs for ameliorating hyperlipidemia via inhibiting cholesterol synthesis by statin agents, or the like.

To date, an action of inducing obesity via controlling the synthesis of sphingolipids have not been known. A SMS inhibitor developed as anti-diabetes drug, anti-obesity drug or a drug for treating fatty liver does not exist, either.

On the other hand, RNAi is a phenomenon found by Fire et al in 1998 (NPL 7), in which a double stranded RNA strongly suppresses the expression of a target gene homologous thereto. It is recently taken notice since it is easier than conventional transgenic methods using a vector or the like, has a high specificity to the target and can be applied to a gene therapy. Among molecules that mediate RNAi, a short chain interfering RNA (siRNA) is advanced for its application (NPL 8). However, it has not been developed as an SMS inhibitor. It has not been known to have an effect of ameliorating a metabolic syndrome as an SMS inhibitor, either.

CITATION LIST

Non Patent Literature

[NPL 1] Yamaoka et al, The Journal of Biological Chemistry, 279, 18688-18693, (2004)
[NPL 2] Huitema et al, The EMBO Journal, 23, 33-44, (2004)
[NPL 3] Tafesse et al, The Journal of Biological Chemistry, 281, 29421-29425, (2006)
[NPL 4] Park et al, Circulation, 110, 3465-3471, (2004)
[NPL 5] Liu et al, Arteriosclerosis, Thrombosis, and Vascular Biology, 29, 850-856, (2009)
[NPL 6] Liu et al, Circulation Research, 105, 295-303, (2009)
[NPL 7] Fire et al, Nature. 391: 806-11, (1998)
[NPL 8] Elbashire et al, Nature. 411: 494-8, (2001)

SUMMARY OF INVENTION

Technical Problem

The present invention relates to decreasing body weight, decreasing visceral fat, decreasing triglycerides in the liver and ameliorating obesity and fatty liver by suppressing the synthesis of sphingolipids, as well as a drug for treating a metabolic syndrome such as diabetes.

Solution to Problem

Regarding the above problem, it is found that the above disease can be treated or prevented by suppressing and controlling the expression of sphingomyelin synthetases, in particular, SMS2 and the present invention has been completed. Therefore, the present invention provides the followings:
(Item 1)
A pharmaceutical composition for treating or preventing a metabolic syndrome, comprising a nucleic acid that suppresses the expression of SMS2.
(Item 2)
The pharmaceutical composition according to Item 1, wherein said nucleic acid is an siRNA.
(Item 3)
The pharmaceutical composition according to Item 2, wherein said siRNA consists of any one or more selected from the group consisting of siRNAs of the following (a)-(o):
(a) an siRNA wherein one strand of the duplex RNA portion is a base sequence set forth by SEQ ID NO: 1 and the other strand of the duplex RNA portion is a base sequence set forth by SEQ ID NO: 2 <SMS2-i6>;
(b) an siRNA wherein one strand of the duplex RNA portion is a base sequence set forth by SEQ ID NO: 3 and the other strand of the duplex RNA portion is a base sequence set forth by SEQ ID NO: 4 <SMS2-i7>;

(c) an siRNA wherein one strand of the duplex RNA portion is a base sequence set forth by SEQ ID NO: 5 and the other strand of the duplex RNA portion is a base sequence set forth by SEQ ID NO: 6 <SMS2-i8>;
(d) an siRNA wherein one strand of the duplex RNA portion is a base sequence set forth by SEQ ID NO: 7 and the other strand of the duplex RNA portion is a base sequence set forth by SEQ ID NO: 8 <SMS2-i104>;
(e) an siRNA wherein one strand of the duplex RNA portion is a base sequence set forth by SEQ ID NO: 9 and the other strand of the duplex RNA portion is a base sequence set forth by SEQ ID NO: 10 <SMS2-i105>;
(f) an siRNA wherein one strand of the duplex RNA portion is a base sequence set forth by SEQ ID NO: 11 and the other strand of the duplex RNA portion is a base sequence set forth by SEQ ID NO: 12 <SMS2-i106>;
(g) an siRNA wherein one strand of the duplex RNA portion is a base sequence set forth by SEQ ID NO: 13 and the other strand of the duplex RNA portion is a base sequence set forth by SEQ ID NO: 14 <SMS2-i107>;
(h) an siRNA wherein one strand of the duplex RNA portion is a base sequence set forth by SEQ ID NO: 15 and the other strand of the duplex RNA portion is a base sequence set forth by SEQ ID NO: 16 <SMS2-i108>;
(i) an siRNA wherein one strand of the duplex RNA portion is a base sequence set forth by SEQ ID NO: 17 and the other strand of the duplex RNA portion is a base sequence set forth by SEQ ID NO: 18 <SMS2-i109>;
(j) an siRNA wherein one strand of the duplex RNA portion is a base sequence set forth by SEQ ID NO: 21 and the other strand of the duplex RNA portion is a base sequence set forth by SEQ ID NO: 22 <SMS2-i3>;
(k) an siRNA wherein one strand of the duplex RNA portion is a base sequence set forth by SEQ ID NO: 23 and the other strand of the duplex RNA portion is a base sequence set forth by SEQ ID NO: 24 <SMS2-i11>;
(l) an siRNA wherein one strand of the duplex RNA portion is a base sequence set forth by SEQ ID NO: 39 and the other strand of the duplex RNA portion is a base sequence set forth by SEQ ID NO: 40 <SMS2-i1>;
(m) an siRNA wherein one strand of the duplex RNA portion is a base sequence set forth by SEQ ID NO: 41 and the other strand of the duplex RNA portion is a base sequence set forth by SEQ ID NO: 42 <SMS2-i2>;
(n) an siRNA wherein one strand of the duplex RNA portion is a base sequence set forth by SEQ ID NO: 45 and the other strand of the duplex RNA portion is a base sequence set forth by SEQ ID NO: 46 <SMS2-i5>; and
(o) an siRNA of any of (a)-(n), wherein one to several nucleotides are added, inserted, deleted or substituted in one or both of the base sequences, and having an activity of suppressing the expression of SMS2.
(Item 4)
The pharmaceutical composition according to Item 1, wherein said nucleic acid is an antisense nucleic acid.
(Item 5)
The pharmaceutical composition according to Item 1 or 4, wherein said nucleic acid is an antisense nucleic acid comprising a locked nucleic acid (LNA).
(Item 5A)
The pharmaceutical composition according to any of Item 1, 4 or 5, wherein said nucleic acid is an antisense nucleic acid comprising a locked nucleic acid (LNA) at 5' end and an LNA at 3' end.

(Item 6)
The pharmaceutical composition according to Item 4, 5 or 5A, wherein said antisense nucleic acid consists of any one or more of SEQ ID NOs: 81-92.
(Item 7)
The pharmaceutical composition according to any one of Items 1-5, 5A or 6, wherein said metabolic syndrome is one or two or more selected from the group consisting of obesity, diabetes, dyslipidemia and fatty liver.
(Item 7A)
The pharmaceutical composition according to any one of Items 1-5, 5A, 6, 7 or 7A, wherein said nucleic acid is comprised in an amount effective to suppress the expression of SMS2.
(Item 7B)
The pharmaceutical composition according to any one of Items 1-5, 5A, 6 or 7, further comprising a pharmaceutically acceptable carrier.
(Item 8)
An siRNA set forth in any one selected from the group consisting of the following (a)-(o):
(a) an siRNA wherein one strand of the duplex RNA portion is a base sequence set forth by SEQ ID NO: 1 and the other strand of the duplex RNA portion is a base sequence set forth by SEQ ID NO: 2 <SMS2-i6>;
(b) an siRNA wherein one strand of the duplex RNA portion is a base sequence set forth by SEQ ID NO: 3 and the other strand of the duplex RNA portion is a base sequence set forth by SEQ ID NO: 4 <SMS2-i7>;
(c) an siRNA wherein one strand of the duplex RNA portion is a base sequence set forth by SEQ ID NO: 5 and the other strand of the duplex RNA portion is a base sequence set forth by SEQ ID NO: 6 <SMS2-i8>;
(d) an siRNA wherein one strand of the duplex RNA portion is a base sequence set forth by SEQ ID NO: 7 and the other strand of the duplex RNA portion is a base sequence set forth by SEQ ID NO: 8 <SMS2-i104>;
(e) an siRNA wherein one strand of the duplex RNA portion is a base sequence set forth by SEQ ID NO: 9 and the other strand of the duplex RNA portion is a base sequence set forth by SEQ ID NO: 10 <SMS2-i105>;
(f) an siRNA wherein one strand of the duplex RNA portion is a base sequence set forth by SEQ ID NO: 11 and the other strand of the duplex RNA portion is a base sequence set forth by SEQ ID NO: 12 <SMS2-i106>;
(g) an siRNA wherein one strand of the duplex RNA portion is a base sequence set forth by SEQ ID NO: 13 and the other strand of the duplex RNA portion is a base sequence set forth by SEQ ID NO: 14 <SMS2-i107>;
(h) an siRNA wherein one strand of the duplex RNA portion is a base sequence set forth by SEQ ID NO: 15 and the other strand of the duplex RNA portion is a base sequence set forth by SEQ ID NO: 16 <SMS2-i108>;
(i) an siRNA wherein one strand of the duplex RNA portion is a base sequence set forth by SEQ ID NO: 17 and the other strand of the duplex RNA portion is a base sequence set forth by SEQ ID NO: 18 <SMS2-i109>;
(j) an siRNA wherein one strand of the duplex RNA portion is a base sequence set forth by SEQ ID NO: 21 and the other strand of the duplex RNA portion is a base sequence set forth by SEQ ID NO: 22 <SMS2-i3>;
(k) an siRNA wherein one strand of the duplex RNA portion is a base sequence set forth by SEQ ID NO: 23 and the other strand of the duplex RNA portion is a base sequence set forth by SEQ ID NO: 24 <SMS2-i11>;
(l) an siRNA wherein one strand of the duplex RNA portion is a base sequence set forth by SEQ ID NO: 39 and the other strand of the duplex RNA portion is a base sequence set forth by SEQ ID NO: 40 <SMS2-i1>;
(m) an siRNA wherein one strand of the duplex RNA portion is a base sequence set forth by SEQ ID NO: 41 and the other strand of the duplex RNA portion is a base sequence set forth by SEQ ID NO: 42 <SMS2-i2>;
(n) an siRNA wherein one strand of the duplex RNA portion is a base sequence set forth by SEQ ID NO: 45 and the other strand of the duplex RNA portion is a base sequence set forth by SEQ ID NO: 46 <SMS2-i5>; and
(o) an siRNA of any of (a)-(n), wherein one to several nucleotides are added, inserted, deleted or substituted in one or both of the base sequences, and having an activity of suppressing the expression of SMS2.
(Item 9)
The siRNA according to Item 8, for treating or preventing a metabolic syndrome.
(Item 10)
The siRNA according to Item 9, wherein said metabolic syndrome is one or two or more selected from the group consisting of obesity, diabetes, dyslipidemia and fatty liver.
(Item 10A)
Use of siRNA according to any one of Items 8-10, for the manufacture of a medicine for treating or preventing a metabolic syndrome.
(Item 10B)
Use according to Item 10A, wherein said metabolic syndrome is one or two or more selected from the group consisting of obesity, diabetes, dyslipidemia and fatty liver.
(Item 11)
A locked nucleic acid (LNA)-containing nucleic acid consisting of any one or more of SEQ ID NOs: 81-92.
(Item 12)
The locked nucleic acid (LNA)-containing nucleic acid according to Item 11, for treating or preventing a metabolic syndrome.
(Item 13)
The locked nucleic acid (LNA)-containing nucleic acid according to Item 12, wherein said metabolic syndrome is one or two or more selected from the group consisting of obesity, diabetes, dyslipidemia and fatty liver.
(Item 14)
A method for treating or preventing a metabolic syndrome, said method comprising: administering the pharmaceutical composition according to any one of Items 1-5, 5A, 6, 7, 7A or 7B to a subject in need of said treatment or prevention.
(Item 15)
The method according to Item 14, wherein said metabolic syndrome is one or two or more selected from the group consisting of obesity, diabetes, dyslipidemia and fatty liver.
(Item 16)
A method for treating or preventing a metabolic syndrome, said method comprising: administering the siRNA according to any one of Items 8-10, 10A or 10B to a subject in need of said treatment or prevention.
(Item 17)
The method according to Item 16, wherein said metabolic syndrome is one or two or more selected from the group consisting of obesity, diabetes, dyslipidemia and fatty liver.
(Item 18)
A method for treating or preventing a metabolic syndrome, said method comprising: administering the locked nucleic acid (LNA)-containing nucleic acid according to any one of Items 11-13 to a subject in need of said treatment or prevention.

(Item 19)
The method according to Item 18, wherein said metabolic syndrome is one or two or more selected from the group consisting of obesity, diabetes, dyslipidemia and fatty liver.

Relating to the present invention, it has been known that a metabolic syndrome result from complex factors. Therefore, it is likely that an occurrence of a medicament having a new mechanism of action can supplement the weakness of conventional drugs.

The present inventors has developed a method for ameliorating a metabolic syndrome by controlling sphingolipid metabolism, thereby indirectly affecting neutral lipid synthesis/metabolism, which has been not known to date.

The present inventors propose a method for ameliorating a metabolic syndrome by controlling sphingomyelin synthetases such as SMS2, a synthetase of sphingomyelin that is one of sphingolipids, to affect the synthesized amount of triacylglycerol. SMS produces equimolar amount of diacylglycerol in synthesizing sphingomyelin. From the experiments exemplified herein, it is demonstrated that the diacylglycerol is likely to be a material for the synthesis of triglycerol, a representative neutral lipid. Specifically, as an illustrative example, increase in body weight of SMS2 gene-deficient mice fed by a high fat diet was significantly decreased compared to a control group and closer to weight of mice fed by normal diet. That is, it can be expected that by controlling the activity of SMS, the synthesized amount of triacylglycerol is controlled and consequently a metabolic syndrome are ameliorated.

Then, it has been considered that a therapeutic effect on a metabolic syndrome can be expected by inhibiting SMS2 function and, for example, application of an RNAi (RNA interference) method that is a novel molecular-specific knockdown method, to a therapy has been investigated.

An RNAi method is a technique that quickly suppresses the expression of a specific gene at a gene level by using a short interfering dsRNA (siRNA (small interfering RNA)) (Non-patent Document 7 and 8). The present inventors have selected multiple target sequences from SMS2 mRNA sequence, synthesized their siRNA and found that knockdown of SMS2 can be linked to healing diseases.

Advantageous Effects of Invention

Conventionally, there has not been drugs for ameliorating a metabolic syndrome that are via controlling the synthesis of sphingolipids. Therefore, the present invention enables it possible to make a medicament having a new mechanism of action.

BRIEF DESCRIPTION OF DRAWINGS

In FIG. 5A, in the order from left, shown are a group wherein wild types were fed by normal diet (WT/ND), a group wherein wild types were fed by high fat diet (WT/HFD), a group wherein SMS2-KO mice were fed by normal diet (SMS2 KO/ND), and a group wherein SMS2-KO mice were fed by high fat diet (SMS2 KO/HFD). Y axis shows relative amount of mRNA. In the WT group, by feeding high fat diet, the expression of adiponectin was suppressed, while in the SMS2 KO group, even when high fat diet was fed, a relatively high expression amount was maintained.

FIG. 5B-1 shows the result in Example 1 wherein the effect of 60% fat diet administration on an insulin receptor in adipose tissues was investigated. The comparison of relative expression amount of insulin receptor is shown between wild type (WT) and SMS2-KO mice to which high fat diet (HFD; 60% fat diet) or control normal diet (ND) were administered. In the order from left, shown are a group wherein wild types were fed by normal diet (WT/ND), a group wherein wild types were fed by high fat diet (WT/HFD), a group wherein SMS2-KO mice were fed by normal diet (SMS2 KO/ND), and a group wherein SMS2-KO mice were fed by high fat diet (SMS2 KO/HFD). Y axis shows relative amount of mRNA. In the wild type mice, when high fat diet (HFD; 60% fat diet) was fed, the expression amount of insulin receptor decreased. In SMS2-KO mice, decrease in the expression of insulin receptor did not occur by high fat diet and it was an almost similar expression amount to that of a case which control normal diet was fed. In addition, the expression amount of insulin receptor when high fat diet was administered to SMS2-KO mice was significantly higher compared to when high fat diet was administered to wild type. From the above results, it was suggested that in adipose tissues of SMS2-KO mice, decrease in the expression of insulin receptor by high fat diet as observed in wild type mice did not occur, and thus the SMS2-KO mice did not become insulin resistance.

FIG. 5B-2 shows the result in Example 1 wherein the effect of 60% fat diet administration on Glut4 in adipose tissues was investigated. The comparison of relative expression amount of Glut4 is shown between wild type (WT) and SMS2-KO mice to which high fat diet (HFD; 60% fat diet) or control normal diet (ND) were administered. In the order from left, shown are a group wherein wild types were fed by normal diet (WT/ND), a group wherein wild types were fed by high fat diet (WT/HFD), a group wherein SMS2-KO mice were fed by normal diet (SMS2 KO/ND), and a group wherein SMS2-KO mice were fed by high fat diet (SMS2 KO/HFD). Y axis shows relative amount of mRNA. In the wild type mice, when high fat diet (HFD; 60% fat diet) was fed, the expression amount of Glut4 decreased, while in SMS2-KO mice, the degree of decrease in the expression of Glut4 by high fat diet was suppressed and it was an almost similar expression amount to that of a case which control normal diet was fed. In addition, the expression amount of Glut4 when high fat diet was administered to SMS2-KO mice was significantly higher compared to when high fat diet was administered to wild type. From the above results, it was suggested that in adipose tissues of SMS2-KO mice, decrease in the expression of Glut4 by high fat diet as observed in wild type mice did not occur, and thus the SMS2-KO mice did not become insulin resistance.

FIG. 5H-1 shows the result in Example 1 wherein the blood glucose concentration in response to insulin was investigated. 4 weeks old wild type (WT) and SMS2-KO mice were administered high fat diet (HFD; 60% fat diet) for 6 weeks, at the time 6 weeks had elapsed, insulin were intraperitoneally administered in 0.5 U/kg. The results of blood glucose concentrations that were measured before administration and at 15, 30, 60, 90 and 120 minutes after administration are shown. In particular, since blood glucose concentration in SMS2-KO mice was significantly decreased compared to in wild type mice at 30, 60 and 90 minutes after administration, it became apparent that SMS2-KO mice were more sensitive to insulin. White circle shows wild type (WT) and black circle shows SMS2-KO mice. * and ** both show significant ($p<0.05$ and $p<0.01$, respectively). Y axis shows blood glucose concentration (mg/dL) and X axis shows elapsed time after administration (minute).

FIG. 5H-2 shows a radio of area under curve (AUC) in FIG. 5H-1 to wild type (WT) (WT=1) in a bar graph. Since it was significantly decreased by about 20% in SMS2-KO mice compared to in wild type mice, it became apparent that SMS2-KO mice are more sensitive to insulin. From the above results of FIG. 5F, G, H-1 and H-2, it can be said that if SMS2 is knocked out, it is resistant to diabetes with insulin resistance compared to WT.

FIG. 16 shows a result wherein SMS2-i3 or SMS2-i11 were administered into mice via tail vein injection and the change of body weight was investigated at the time when 10 days has elapsed after administration. In the case which SMS2-i3 or SMS2-i11 were administered and in the control group mice, there was no significant difference in change of body weight.

FIG. 20A shows a result wherein HepG2 cell that is a human liver parenchymal cell strain, was transformed with control siRNA sequence (CTR-i) and stained with a fluorescent reagent AdipoRed (NileRed) after 72 hours which can specifically stain triglyceride, and the cell was observed with a fluorescent microscope after 5 minutes. FIG. 20-C shows a result wherein HepG2 cell that is a human liver parenchymal cell strain, was transformed with SMS2-i109 and stained with a fluorescent reagent AdipoRed (NileRed) after 72 hours which can specifically stain triglyceride, and the cell was observed with a fluorescent microscope after 5 minutes. It could be confirmed that when the cell was transformed with SMS2-i109, particle size of lipid droplet in the cell was smaller compared to when CTR-i was used.

DESCRIPTION OF EMBODIMENTS

Figure 1:
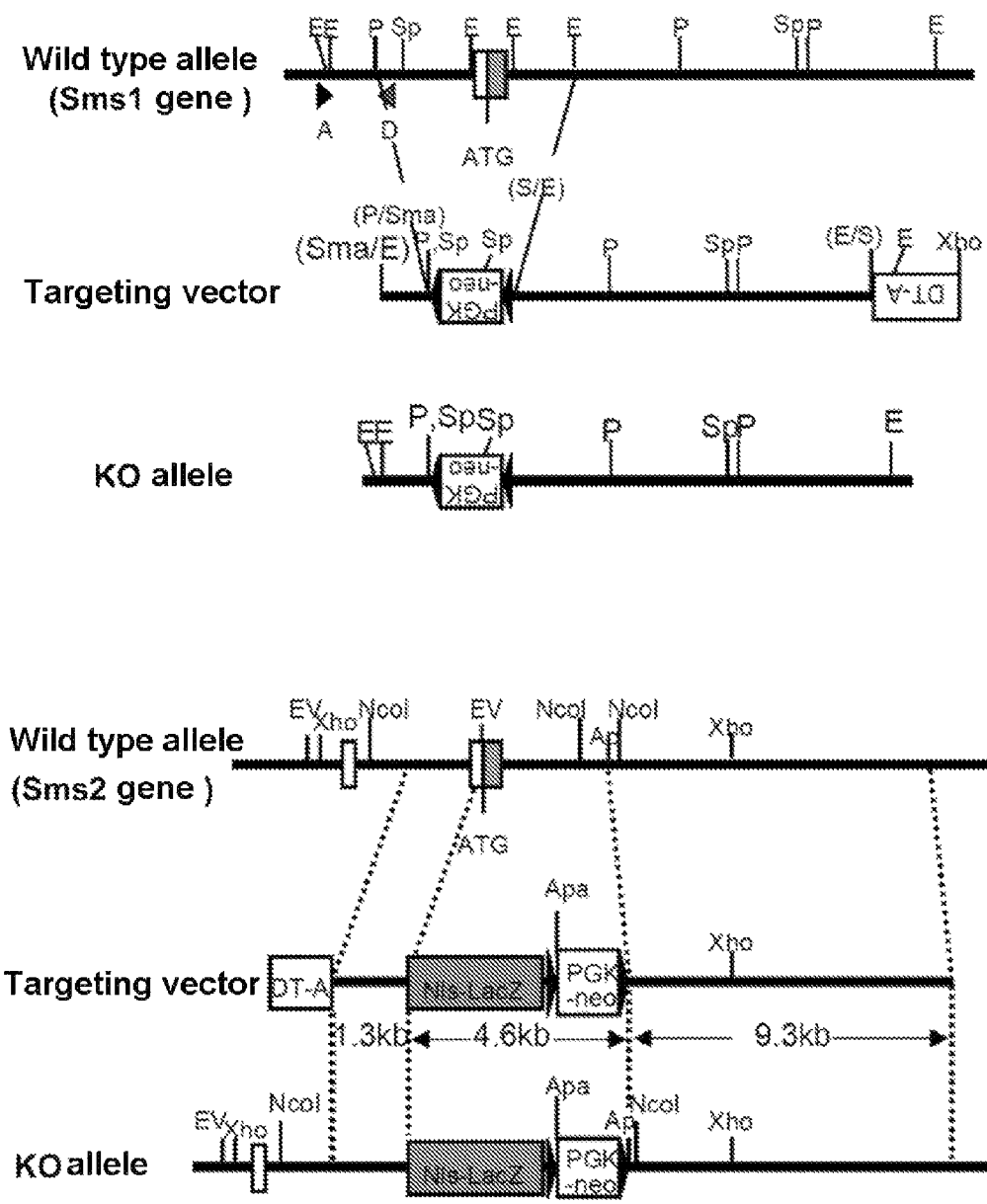
FIG. 1 shows a summary of targeting vectors used in the production of SMSs knockout (NO) mice in Example 1. Left shows a summary of a targeting vector used in knocking out SMS 1 gene, while right shows a summary of a targeting vector used in knocking out SMS2 gene. In the Figure, E refers to restriction enzyme cutting sites of EcoRI, P refers to those of PstI, S refers to those of SalI, Sp refers to those of SpeI, Sma refers to those of SmaI and Xho refers to those of XhoI.

Preferred embodiments of the present invention are explained below. Throughout the present specification, unless specifically referred to, an expression in a singular form is to be understood to encompass the concept of its plurality form. Therefore, unless specifically referred to, singular form articles (for example, "a", "an", "the" or the like in English, and corresponding articles and adjectives or the like in other languages) are to be understood to encompass the concept of their plurality form. Furthermore, terms used herein, unless specifically referred to, are to be understood to be used in the meaning usually used in the art. Therefore, unless defined otherwise, all technical terms and scientific terms herein have the same meaning as generally recognized by those skilled in the art to which the present invention belongs. If they contradict, the present specification (including the definition) governs.

DEFINITION

The definition of terms specifically used herein are listed.

As used herein, "sphingomyelin synthetase" (also referred herein as "SMS") refers to an enzyme that synthesizes sphingomyelin (also referred herein as "SM") wherein it converts ceramide into sphingomyelin in the presence of phosphatidylcholine (also referred herein as "PC"), and which plays an important role in cell death and survival (see, Non-patent Documents 1 and 2). Here, phosphatidylcholine after conversion is converted into diacylglycerol. As sphingomyelin synthetases, typically, SMS 1 and SMS2 are known, as well as homologs (see, Non-patent Documents 1 and 2). SMS1 is known to be expressed in the Golgi body and be involved in de novo synthesis of SM. On the other hand, SMS2 is expressed in the Golgi body and cell membrane, and its physiological function is not known in detail (see, Non-patent Document 3). In addition, GenBank Accession numbers of SMS1 are NM_147156 (human) and NM_144792 (mouse), and those of SMS2 are BC028705.1 (human), BC041369.2 (human) and NM_028943 (mouse).

"Metabolic syndrome" or "metabolic disease" herein are used in the broadest meaning used in the art, and refer to states wherein hyperglycemia, dyslipidemia or hypertension are caused with a common factor of visceral fat obesity and are previously called as "lifestyle related disease", "adult diseases" or the like. All these terms are exchangably used herein. Metabolic syndrome or metabolic disease herein specifically comprise at least one of diseases such as diabetes, obesity, dyslipidemia (excess of visceral fat), fatty liver or the like, or states such as decreased expression of adiponectin. Furthermore, since arteriosclerosis is often developed after some years as a result of metabolic syndrome, it is understood that "metabolic syndrome" does not comprise arteriosclerosis in general but comprises the arteriosclerosis caused by metabolic syndrome (for example, diabetes, obesity or the like).

"Anti-diabetes" herein refer to a drug capable of treating (for example, suppressing, preventing or the like) diabetes. Diabetes is used in the meaning usually used in the art and refers to a state wherein a blood glucose level (glucose concentration in blood) is pathologically high, and diabetes is largely divided into type 1 diabetes which is caused by not secreting insulin from the pancreas and type 2 diabetes which is caused by decreased function of insulin. In the present specification, diabetes encompasses type I and type II and is not constricted to its type. In the present specification, "type I anti-diabetes" is referred when specifically referring to type I and "type II anti-diabetes" is referred when specifically referring to type II.

Here, insulin resistance syndrome is a major cause of diabetes (in particular, type 2 diabetes) and is a fundamental cause for lifestyle related diseases such as obesity and circulatory system disease. Insulin resistance means a state which a response to insulin of peripheral tissues is dull. Since, as a result of a response to insulin being dull, since peripheral tissues cannot respond to insulin, they cannot uptake blood glucose and state in which blood glucose level is high is maintained. Since pancreas releases a large amount of insulin so as to decrease blood glucose, the concentration of insulin in blood becomes high.

Therefore, by ameliorating insulin resistance, blood glucose level decreases and thus it is useful for treating or preventing the above lifestyle related diseases. An index of amelioration of insulin resistance is that the concentration of insulin in blood is decreased when measured. In addition, increased concentration of adiponectin in blood is another index. In view of above, a drug for increasing adiponectin or a drug which decreases the concentration of insulin in blood while maintaining blood glucose level at a normal level becomes a drug for ameliorating insulin resistance and thus is also effective for treating diabetes or obesity, circulatory system diseases (arteriosclerosis, hypertension or the like) and metabolic syndrome resulting from insulin resistance.

"Anti-obesity drug" herein refers to a drug capable of treating (for example, suppressing, preventing or the like) obesity. "obesity" is one of metabolic syndromes and can be recognized as one of diseases. Obesity state can include, for example, excess of body weight, excess of fat or the like. If BMI measured as a body mass index is 25 or more, it is deemed as obesity. When body fat percentage is used, 18% or more is a criteria. An effect of treating obesity can be judged by measuring body weight, measuring fat, measuring triglyceride accumulated in fat, or the like.

"Drug for decreasing body weight" herein refers to a drug which decreases body weight or suppresses feeding. "decrease in body weight" or "decreasing body weight" herein must be interpreted in the broadest manner to encompass a case of decreasing the current body weight as well as a case of suppressing increase in body weight and maintaining the current body weight. Decrease in body weight can be judged by measuring body weight, measuring fat, measuring triglyceride accumulated in fat, or measuring the amount of feeding.

"Drug for decreasing visceral fat" herein refers to a drug which decreases visceral fat or prevent increase in visceral fat. Visceral fat is used in the meaning usually used in the art and refers to fat accumulated around viscera among body fat. Decrease in visceral fat can be judged by measuring white fat cell mass, measuring with abdominal CT image, or the like. An object for decreasing visceral fat can include diseases or symptoms such as excess of visceral fat or dyslipidemia. "Dyslipidemia" refers to a state in which fat included in blood is excess or short, and was previously also called as hyperlipidemia. Dyslipidemia is one of metabolic syndromes and can be recognized as one of diseases.

"Drug for treating fatty liver" herein refers to a drug capable of treating (for example, suppressing, preventing) fatty liver. "Fatty liver" is used in the meaning usually used in the art and refers to a status in which a large amount of fat accumulates in the liver. As a cause for it, alcoholic, nutritive, diabetic, drug-induced causes or the like are known. Fatty liver is said to be partly developed to cirrhosis. In the sense, the present invention can be recognized to be a drug for preventing cirrhosis. An effect of treating fatty liver can be judged by measuring triglyceride (TG) in fat, measuring liver weight, grossly inspecting liver, or the like.

"Drug for increasing adiponectin expression" herein refers to a drug which increases the expression of adiponectin. Adiponectin is used in the meaning usually used in the art, is a secretory protein that is secreted from fat cell and is said to be negatively correlated with visceral fat amount, and said to be an index for so-called metabolic diseases. Increase in adiponectin expression can be judged, for example, by obtaining fat, extracting mRNA thereof and measuring the expression amount of adiponectin mRNA, by immunological measurement using an anti-adiponectin antibody, or the like.

"Expression" of a gene, polynucleotide, polypeptide or the like herein refers to that such gene or the like undergo in vivo a certain action to become another form. Preferably, it refers to that gene, polynucleotide or the like are transcribed and translated into a polypeptide form. It can be also one embodiment of the expression that they are transcribed so as to produce mRNA. More preferably, such forms of polypeptide can be one after post-translation processing.

Therefore, "decrease" in "expression" of gene, polynucleotide, polypeptide or the like herein refers to that the amount of expression is significantly decreased when the agent of the present invention is acted, compared to a case it is not acted. Preferably, decrease in expression encompasses decrease in the expression amount of a polypeptide. "Increase" in "expression" of gene, polynucleotide, polypeptide or the like herein refers to that the amount of expression is significantly increased when the agent of the present invention is acted, compared to a case it is not acted. Preferably, increase in expression encompasses increase in the expression amount of a polypeptide. "Induction" of "expression" of a gene herein refers to that a cell is acted by an agent so as to increase the expression amount of the gene. Therefore, induction of expression encompasses allowing the gene to be expressed when the expression of the gene is not found at all, and increasing the expression of the gene when the expression of the gene has been already found.

"Detection" or "quantification" of a gene expression (for example, mRNA expression, and polypeptide expression) herein can be achieved by using a suitable method, for example, including measurement of mRNA and immunological measuring methods. As molecular biological measuring methods, for example, Northern blot method, dot blot method or PCR method or the like are exemplified. As immunological measuring methods, for example, ELISA method using a microtiter plate, RIA method, fluorescent antibody method, Western blot method, immunohistological staining method or the like are exemplified. In addition, as a quantifying method, ELISA method or RIA method or the like are exemplified. It can be also carried out by a gene analyzing method using an array (for example, DNA array, and protein array). A DNA array is broadly in reviewed in (Shujunsha Co., Ltd., ed., Saibo Kogaku Bessatsu [Cell Engineering, Separate zvolume], "DNA Maikuroarei to Saishin PCR Ho [DNA Microarray and the Latest PCR Method]"). A protein array is described in detail Nat. Genet. 2002 December; 32 Suppl: 526-32. In addition to the above, a method for analyzing gene expression include, but not limited to, RT-PCR, RACE method, SSCP method, immunoprecipitation, two-hybrid system, in vitro translation or the like. Additional such analyzing method is described, for example, in Genomu Kaiseki Jikken Ho [A Experimental Method for Genome Analysis], Nakamura Yusuke Rabo Manyuaru [Laboratory Manual by Yusuke Nakamura], Yusuke Nakamura ed., Yodosha Co., Ltd. (2002), the description of which are all incorporated herein as reference.

"Expression amount" herein refers to an amount in which a polypeptide or mRNA is expressed in a cell of interest or the like. Such expression amount includes expression amount of the polypeptide of the present invention at a protein level evaluated by any suitable methods using the antibody of the present invention including immunological measuring methods such as ELISA method, RIA method, fluorescent antibody method, Western blot method, immunohistological staining method or the like, or expression amount of the polypeptide of the present invention at an mRNA level evaluated by any suitable method including molecular biological measuring methods such as Northern blot method, dot blot method, PCR method or the like. "Change of expression amount" means increase or decrease in expression amount of a polypeptide of present invention at a protein level or mRNA level evaluated by any suitable method including the above immunological measuring methods or molecular biological measuring methods.

"A material (for example, nucleic acid) that suppresses the expression (of a gene such as SMS2)" herein is not specifically limited as long as it is a material that suppresses the transcription of mRNA of a target gene, a material (for example, a nucleic acid) that degrades a transcribed mRNA, or a material that suppresses the translation of a protein from mRNA. As such materials, nucleic acids such as siRNA, an antisense oligonucleotide, a ribozyme or expression vector thereof or the like are exemplified. Among them, siRNA and expression vector thereof are preferred, and siRNA is specifically preferred. A "material that suppresses gene expression" also includes proteins, peptides, and other small molecules, besides the above.

Here, the target gene in the present invention is an SMS2 gene.

"siRNA" herein is an RNA molecule having a double stranded RNA portion consisting of 15-40 bases, and has a function of cleaving the mRNA of a target gene having a sequence complementary to an antisense strand of the siRNA, thereby suppressing the expression of the target gene. Specifically, the siRNA in the present invention is an RNA comprising a double stranded RNA portion which consists of a sense RNA strand consisting of a sequence homologous to a contiguous RNA sequence in the mRNA of a SMS2 gene, and an antisense RNA strand consisting of a sequence complementary to the sense RNA sequence. Designing and producing such siRNA and variant siRNA described below fall within the scope of technique of those skilled in the art.

The length of the double stranded RNA portion in base is 15-40 bases, preferably 15-30 bases, more preferably 15-25 bases, further more preferably 18-23 bases and most preferably 19-21 bases. It is understood that the upper and lower limits are not such specific ones and can be any combination of the listed ones. The terminal structure of sense strand or antisense strand of siRNA can be suitably selected, without specific limitation, depending on its purpose, and can be, for example, one with blunt end, or one with protruding end (overhung), and one with 3' protruding end is preferred. siRNA which has overhangs consisting of several bases, preferably 1-3 bases, more preferably 2 bases at 3' ends of the sense RNA strand and antisense RNA strand often has a excellent effect of suppressing the expression of its target gene and is thus preferred. The kind of the base constituting the overhung is not specifically limited and can be any of bases that constitute an RNA or bases that constitute a DNA. Preferred overhung sequence can include dTdT (2 bp of deoxyTs) at 3' end or the like. For example, preferred siRNA includes, but not limited to, all siRNA whose sense and antisense strands have dTdT (2 bp of deoxyTs) at their 3' ends.

Furthermore, siRNA wherein one to several nucleotides are deleted, substituted, inserted, and/or added in one or both of the sense strand or antisense strand of the above siRNA can be also used. Here, one to several bases are, but not specifically limited to, preferably 1-4 bases, more preferably 1-3 bases, most preferably 1-2 bases. Specific examples of such variation include, but not limited to, one wherein the number of 3' overhung portion is 0-3 bases, one wherein the base nucleotide of 3' overhung portion is changed into other base sequence, or one wherein the lengths of the above sense RNA strand and antisense RNA strand differ in 1-3 bases due to insertion, addition or deletion of base(s), one wherein the base(s) in the sense strand and/or antisense strand is replaced with other base(s), or the like. However, in the variant siRNAs it is necessary that the sense strand and antisense strand hybridize and that such variant siRNAs have an ability of suppressing a gene expression similarly to siRNA without any variation.

Furthermore, the siRNA can be a molecule with a structure of one closed end, for example, siRNA with a hairpin structure (Short Hairpin RNA; shRNA). shRNA is an RNA comprising a sense strand RNA of a specific sequence of a target gene, an antisense strand RNA consisting of a sequence complementary to the sense strand sequence, and a liker sequence that links the both strands, and wherein the sense strand portion and the antisense strand portion hybridize to form a double stranded RNA portion.

It is desirable that siRNA does not exhibit so-called off-target effect in clinical use. Off-target effect refers to an effect of suppressing the expression of a gene different from a target gene which partly has a homology to the siRNA used. In order to avoid the off-target effect, it is possible to pre-confirm by using a DNA microarray or the like that a candidate siRNA does not have a cross reactivity. In addition, it is possible to avoid off-target effect by confirming with known databases provided by NCBI (National Center for Biotechnology Information) or the like whether there is any gene other than a target gene which comprises a portion highly homologous to the sequence of a candidate siRNA.

In order to make the siRNA of the present invention, known methods such as methods using chemical synthesis and methods using genetic recombination technique can be suitably used. In methods using chemical synthesis, a double stranded RNA can be synthesized by using conventional methods based on sequence information. In methods using genetic recombination technique, it can be made by constructing an expression vector encoding a sense strand sequence or antisense strand sequence, introducing the vector into a host cell, then obtaining the sense strand RNA or antisense strand RNA which are produced by transcription, respectively. In addition, a desired double stranded RNA can be made by expressing shRNA comprising a sense strand of a specific sequence of a target gene, an antisense strand consisting of a sequence complementary to the sense strand sequence, and a linker sequence liking the both strands, and forming a hairpin structure.

Regarding siRNA, as long as it has an activity of suppressing the expression of a target gene, all or part of the nucleic acid that constitutes the siRNA can be a natural nucleic acid or modified nucleic acid.

In the nucleic acid of the present invention that suppresses the expression of a gene such as SMS2 or the like, a modified nucleic acid can be used. A modified nucleic acid means one wherein a nucleoside (base portion, sugar portion) and/or internucleoside bond portion are modified and which has a different structure from that of a native nucleic acid. A "modified nucleoside" that constitutes a modified nucleic acid includes abasic nucleoside; arabinonucleoside, 2'-deoxyuridine, alpha-deoxyribonucleoside, beta-L-deoxyribonucleoside, other nucleoside having sugar modification; peptide nucleic acid (PNA), peptide nucleic acid bearing phosphate group (PHONA), locked nucleic acid (LNA), morpholino nucleic acid or the like. The nucleoside having sugar modification includes substituted pentoses such as 2'-O-methylribose, 2'-deoxy-2'-fluororibose, 3'-O-methylribose or the like; 1',2'-deoxyribose; arabinose; substituted arabinose; nucleosides whose sugar is modified in hexose and alpha-anomer. Such nucleosides can be a modified base wherein the base portion is modified. Such modified bases include, for example, pyrimidines such as 5-hydroxycytosine, 5-fluorouracil, 4-thiouracil or the like; purines such as 6-methyladenine, 6-thioguanosine or the like; and other heterocyclic bases, or the like.

A "modified internucleoside bond" that constitutes a modified nucleic acid includes, for example, non-native intranucleoside bonds such as alkyl linker, glyceryl linker, amino linker, poly(ethylene glycol) bond, methylphosphonate internucleoside bond; methylphosphothioate, phosphotriester, phosphothiotriester, phosphorothioate, phosphodithioate, triester prodrug, sulfone, sulfonamide, sulfamate, formacetal, N-methylhydroxylamine, carbonate, carbamate, morpholino, boranophosphonate, phosphoramidate or the like.

As a nucleic acid sequence included in the double stranded siRNA of the present invention, the sequences set forth in the Sequence Listing can be preferably used. The nucleotide sequences of these siRNA are shown in Table 1. In Table 1, shown in capital letters are sense RNA sequence and antisense RNA sequence, and shown in lower-case letters or d+capital letters (meaning deoxy forms) are 3' end overhung sequences.

TABLE 1

| siRNA name | Sequence | |
|---|---|---|
| SMS2-i1 | GGUCACUUGGAAAGUCAAA-dTdT | (SEQ ID NO: 71) |
|  | dTdT-CCAGUGAACCUUUCAGUUU | (SEQ ID NO: 72) |

TABLE 1-continued

| siRNA name | Sequence | |
|---|---|---|
| SMS2-i2 | CCGGACUACAUCCAGAUUU-dTdT | (SEQ ID NO: 73) |
|  | dTdT-GGCCUGAUGUAGGUCUAAA | (SEQ ID NO: 74) |
| SMS2-i3 | GGAUGGUAUUGGUUGGGUU-dTdT | (SEQ ID NO: 67) |
|  | dTdT-CCUACCAUAACCAACCCAA | (SEQ ID NO: 68) |
| SMS2-i4 | GCAGAUUGUUGUUGAUCAU-dTdT | (SEQ ID NO: 75) |
|  | dTdT-CGUCUAACAACAACUAGUA | (SEQ ID NO: 76) |
| SMS2-i5 | CAUAGAGACAGCAAAACUU-dTdT | (SEQ ID NO: 77) |
|  | dTdT-GUAUCUCUGUCGUUUUGAA | (SEQ ID NO: 78) |
| SMS2-i6 | GCAUUUCUGUAUCAGAAA-dTdT | (SEQ ID NO: 47) |
|  | dTdT-CGUAAAAGACAUAGUCUUU | (SEQ ID NO: 48) |
| SMS2-i7 | GUCACUUCUGGUGGUAUCA-dTdT | (SEQ ID NO: 49) |
|  | dTdT-CAGUGAAGACCACCAUAGU | (SEQ ID NO: 50) |
| SMS2-i8 | CUGUUUUGGUGGUACCAUU-dTdT | (SEQ ID NO: 51) |
|  | dTdT-GACAAAACCACCAUGGUAA | (SEQ ID NO: 52) |
| SMS2-i11 | GGCUCUUUCUGCGUUACAA-dTdT | (SEQ ID NO: 69) |
|  | dTdT-CCGAGAAAGACGCAAUGUU | (SEQ ID NO: 70) |
| SMS2-i104 | GGGCAUUGCCUUCAUAUAU-dTdT | (SEQ ID NO: 53) |
|  | dTdT-CCCGUAACGGAAGUAUAUA | (SEQ ID NO: 54) |
| SMS2-i105 | GGCUGUUUCUGAGAUACAA-dTdT | (SEQ ID NO: 55) |
|  | dTdT-CCGACAAAGACUCUAUGUU | (SEQ ID NO: 56) |
| SMS2-i106 | GGUGGUGGAUUGUCCAUAA-dTdT | (SEQ ID NO: 57) |
|  | dTdT-CCACCACCUAACAGGUAUU | (SEQ ID NO: 58) |
| SMS2-i107 | GGAUUGUCCAUAACUGGAU-dTdT | (SEQ ID NO: 59) |
|  | dTdT-CCUAACAGGUAUUGACCUA | (SEQ ID NO: 60) |
| SMS2-i108 | CCAUAACUGGAUCACAUAU-dTdT | (SEQ ID NO: 61) |
|  | dTdT-GGUAUUGACCUAGUGUAUA | (SEQ ID NO: 62) |
| SMS2-i109 | GCACACGAACACUACACUA-dTdT | (SEQ ID NO: 63) |
|  | dTdT-CGUGUGCUUGUGAUGUGAU | (SEQ ID NO: 64) |
| CTR-i | UUCUCCGAACGUGUCACGU-dTdT | (SEQ ID NO: 65) |
|  | dTdT-AAGAGGCUUGCACAGUGCA | (SEQ ID NO: 66) |

"Transgenic" herein refers to integration of a specific gene into an organism (or cell or the like), or an organism (for example, including animals (such as a mouse)) (or cell or the like) wherein such gene is integrated or deleted or suppressed. Among transgenic organisms (or cell or the like), one wherein a gene is deleted or suppressed is referred to as a knockout organism (or cell or the like). Therefore, "knockout", when referring to animal or cell or the like, means states wherein a native gene which is targeted does not function or is not expressed.

"Transgenesis" herein refers to introducing a gene of interest into a cell, tissue or animal, conceptually encompasses "transformation", "transduction" and "transfection" or the like, and can be realized by any technique known in the art. In addition, "transgenesis" also encompasses any of one wherein a site to be introduced is not limited and one via homologous recombination wherein a site to be introduced is limited. A method for transgenesis include, but not limited to, for example, methods using retrovirus, plasmid, vector or the like, or electroporation method, methods using particle gun (gene gun), calcium phosphate method. A cell used for transgenesis can be any cell, and use of an undifferentiated cell (for example, fibroblast or the like) is preferred.

"Preventing" herein refers to, by any means, not allowing the occurrence of or at least delaying a disease, disorder or symptom which the present invention targets before occurrence of the disease, disorder or symptom, or not allowing the occurrence of a disorder even if any cause itself of the disease, disorder or symptom occurs.

"Treating" herein refers to stopping the progression of a disease, disorder or symptom which the present invention targets, or completely or partly arresting or ameliorating a disease, disorder or symptom which the present invention targets.

"Treatment" herein refers to somewhat affecting a disease, disorder or symptom or preventing a subject from being in such a disease, disorder or symptom, and can encompass therapy and prevention. In narrower sense, "treatment" refers to the above action after occurrence thereof compared to "prevention".

"Cell death inducing drug" refers to any drug capable of inducing cell death. In the present invention, any material can be used as long as it is a drug capable of inducing cell death by biding to cholesterol in cell membrane and destroying the cell membrane. In an SMS deficient cell, cyclodextrins can be used so as to induce cell death, but it is understood that the drug is not limited to them. "Cyclodextrin" as referred to herein is used in broader sense, refers to any cyclic oligosaccharide and derivatives thereof which several molecules of D-glucose are bound via alpha(1->4) glycoside bond, and refers to any one of substituted (for example, substituent includes, but not limited to, alkyl group, hydroxylalkyl group or the like) or unsubstituted cyclodextrins. Cyclodextrin which can be used as a cell death inducing drug includes, for example, methyl-alpha-cyclodextrin, methyl-beta-cyclodextrin, 2-hydroxylpropyl-beta-cyclodextrin, alpha-cyclodextrin, beta-cyclodextrin or the like (for reference, see, J. Biol. Chem. 270, 29, 17250-17256, 1995; J. Biol. Chem. 275, 44, 34028-34034; Japanese Laid-Open Publication No. 2007-332128 or the like).

"Reconstructed cell" herein refers to a cell produced by introducing a gene of interest into it, optionally after deleting a specific gene by knocking out it. Reconstructed cell can include cells wherein at least one sphingomyelin synthetase (for example, SMS 1, SMS2 or both of SMS1 and SMS2) are transgenically introduced into a cell wherein the sphingomyelin synthetase SMS 1 and SMS2 of the present invention are knocked out, or the like.

It is understood that "medicament" herein is interpreted in the broadest sense in the art, comprise any drug and encompass pharmaceuticals under the Parmaceutical Affaris Law, quasi-drugs or the like as well as any usage of drug and composition or the like which is intended for treatment or prevention by osteogenesis. As such examples, applications in medical art, dental art or the like are listed, for example, a gene therapeutic agent or the like is listed. Usually, a medicament comprises a solid or liquid excipient and can optionally comprise additives such as a disintegrating agent, a flavoring agent, a delayed releasing agent, a lubricant, a binding agent, a coloring agent or the like. The form of a medicament includes, but not limited to, tablets, injections, capsules, granules, powders, fine granules, controlled release formulations or the like.

DESCRIPTION OF PREFERRED EMBODIMENTS

It should be understood that while description of preferred embodiments is described below, the embodiments are illustrative of the present invention and the scope of the present invention is not limited to such preferred embodiments. It should be also understood that those skilled in the art can readily carry out modification, alternation or the like within the scope of the present invention with reference to the preferred embodiments below.

(A Nucleic Acid which Suppresses the Expression of SMS2)

The present invention provides a nucleic acid which suppresses the expression of SMS2. The nucleic acid of the present invention has a function that suppresses the translation or transcription or the like of a nucleic acid. Such a nucleic acid can include an antisense nucleic acid, a nucleic acid having RNAi effect (for example, siRNA), a nucleic acid having a ribozyme activity, or the like. The nucleic acid which suppresses the expression of SMS2 of the present invention can comprise a modified nucleic acid.

Such a nucleic acid (for example, siRNA, antisense nucleic acid) is used for ameliorating, treating or preventing a metabolic syndrome.

A preferred embodiment of the nucleic acid which suppresses the expression of SMS2 of the present invention such as siRNA of SMS2 can include, for example, nucleic acids selected from the group consisting of the following (a)-(c): (a) an antisense nucleic acid toward a transcript of a gene encoding an SMS2 protein or part thereof, (b) a nucleic acid having a ribozyme activity which specifically cleaves a transcript encoding an SMS2 protein; and (c) a nucleic acid having an effect of inhibiting the expression of a gene encoding SMS2 protein via RNAi effect (for example, siRNA).

SMS2 can include, typically, SEQ ID NO: 79 (human) (Locus: NM_152621, 6246 bp), SEQ ID NO: 80 (mouse) (NM_028943, 5791 bp)(full length sequence of SMS2) or the like. However, it is understood that besides above, any sequence known as SMS2 can be used as a target. As such sequences, sequences referred to by a plurality of Accession numbers on genome databases (for example, on nucleotide databases, besides above, NM_001136257, NM_001136258, BC041369, BC028705 (human) or the like are searched, and on protein databases, NP_001129730, NP_689834, NP_001129729, Q8NHU3, AAH41369, AAH28705, Q86VZ5 (the precedings are human), NP_083219 (mouse) or the like) are searched on the public gene database NCBI.

Even if it is not above proteins, for example, proteins which have a high homology (usually 70% or more, preferably 80% or more, more preferably 90% or more, most preferably 95% or more) to the sequences described in these Accession numbers and have functions which the above proteins have (for example, a function of synthesizing sphingomyelin in a cell, or the like), are encompassed in proteins which the present invention targets. It is understood that proteins consisting of an amino acid sequence wherein one or more of amino acids are added, deleted, substituted, or inserted in the amino acid sequences set forth by the Accession numbers related to the above proteins and wherein the number of amino acids that are changed is usually within 30 amino acids, preferably within 10 amino acids, more preferably within 5 amino acids and most preferably within 3 amino acids are also encompassed. Alternatively, ones having a high homology to the DNA sequences set forth by the Accession numbers related to the above nucleotide sequences are also encompassed. High homology means 50% or more, preferably 70% or more, more preferably 80% or more, further more preferably 90% or more (for example, 95% or more, further 96%, 97%, 98% or 99% or more) of homology. Such homology can be determined by mBLAST algorithm (Altschul et al. (1990) Proc. Natl. Acad. Sci. USA 87: 2264-8; Karlin and Altschul (1993) Proc. Natl. Acad. Sci. USA 90: 5873-7). Alternatively, the sequence which the present invention targets can be one which hybridizes under stringent condition to the DNA sequences set forth by Accession numbers related to the above nucleotide sequences. Here, "stringent condition" can include, for example, "2×SSC, 0.1% SDS, 50° C.", "2×SSC, 0.1% SDS, 42 degrees Celsius", "1×SSC, 0.1% SDS, 37 degrees Celsius", more stringent condition can include conditions of "2×SSC, 0.1% SDS, 65 degrees Celsius", "0.5× SSC, 0.1% SDS, 42 degrees Celsius" and "0.2×SSC, 0.1% SDS, 65 degrees Celsius".

Those skilled in the art can suitably obtain a protein functionally equivalent to the above proteins among the above proteins having a high homology by using a method of measuring an activity of synthesizing sphingomyelin. Specific methods for measuring the activity are illustratively described in the Examples. In addition, those skilled in the art can suitably obtain an endogenous gene in other organism which corresponds to the gene based on the base sequence of the gene. Here, in the present specification, protein and gene in organism other than a human which corresponds to the above protein and gene, or protein and gene functionally equivalent to the above protein and gene are, in some times, merely described with the above names.

As a method of inhibiting the expression of a specific endogenous gene such as SMS2, methods using an antisense technique are well known to those skilled in the art. As an action that an antisense nucleic acid inhibits the expression of a target gene, a plurality of factors as follows exist. That is, inhibition of starting transcription by triplex formation, inhibition of transcription by forming a hybrid with a portion wherein opened loop structure is locally made by an RNA polymerase, inhibition of transcription by forming a hybrid with an RNA which is being synthesized, inhibition of splicing by hybrid formation at junction of an intron and an exon, inhibition of splicing by forming hybrid with a spliceosome forming site, inhibition of translocation from nucleus to cytoplasm by hybrid formation with mRNA, inhibition of splicing by forming hybrid with a capping site or poly(A) addition site, inhibition of starting translation by forming hybrid with translation initiator-binding site, inhibition of translation by forming hybrid with ribosome binding site near start codon, inhibition of elongation of peptide chain by forming hybrid with translated region or polysome binding site of mRNA, and inhibition of gene expression by forming hybrid with nucleic acid-protein interacting site, or the like. As explained above, an antisense nucleic acid inhibits the expression of a target gene by inhibiting various processes such as transcription, splicing or translation (Hirashima and Inoue, Shin Seikagaku Jikken Koza [New Lectures on Biochemical Experiment] 2, Kakusan [Nucleic acid] IV, Idenshi no Fukusei to Hatsugen [Gene Replication and Expression], The Japanese Biochemical Society, ed., Tokyo Kagaku Dojin, 1993, 319-347.).

The antisense nucleic acid used in the present invention can inhibit the expression and/or function of the gene encoding SMS2 described above via any actions above. As one embodiment, if an antisense sequence is designed which is complementary to untranslated region near 5' end of mRNA of the gene encoding SMS2 described above, it is considered to be effective in inhibiting the translation of the gene. In addition, a sequence complementary to the coding region or 3' untranslated region can be also used. As such, a nucleic acid comprising an antisense sequence of not only the translated regions of the gene encoding the above SMS2 but also the untranlated regions is also encompassed by antisense nucleic acid used in the present invention. An antisense nucleic acid used is liked downstream of a suitable promoter and is preferably liked, 3' thereto, to a sequence comprising a transcription termination signal. A nucleic acid thus prepared can be transformed into a desired animal (cell) by using known methods. The sequence of an antisense nucleic acid is desirably a sequence complementary to a gene encoding an endogenous SMS2 which the animal (cell) to be transformed has or part thereof, but are not necessarily completely complement as long as it can effectively suppress the expression of the gene. The transcribed RNA is preferably 90% or more, most preferably 95% or more complementary to the transcript of a target gene. In order to effectively inhibit the expression of a target gene by using an antisense nucleic acid, it is preferably that the length of the antisense nucleic acid is at least 12 bases or more and less than 25 bases, but the antisense nucleic acid of the present invention is not necessarily limited to such length and can be, for example, 11 bases or less, 100 bases or more, or 500 bases or more. The antisense nucleic acid can be composed of DNA only, but can comprise nucleic acids other than DNA, for example, a locked nucleic acid (LNA). As an embodiment, the antisense nucleic acid used in the present invention can be an antisense nucleic acid comprising a locked nucleic acid (LNA) at 5' end and an LNA at 3' end. Such an LNA-containing antisense nucleic acid can include, but not limited to, SEQ ID NOs: 81-92 or the like. In addition, in an embodiment of the present invention which uses an antisense nucleic acid, using, for example, the method described in Hirashima and Inoue, Shin Seikagaku Jikken Koza [New Lectures on Biochemical Experiment] 2, Kakusan [Nucleic acid] IV, Idenshi no Fukusei to Hatsugen [Gene Replication and Expression], The Japanese Biochemical Society, ed., Tokyo Kagaku Dojin, 1993, 319-347, based on the nucleic acid sequences of SMS2 set forth in SEQ ID NO: 79 or 80, antisense sequences can be designed. As sequences that can be referred to, SEQ ID NO: 1-18, 21-24, 39-42, 45, 46 or the like can be used, but not limited thereto. For example, those such as SEQ ID NOs: 81-92 described in Example 10 are preferably used, but not limited thereto. These antisense nucleic acids can be confirmed for the effect of the antisense of the present invention by the methods exemplified in Examples 7 and 8 which use mice and HepG2 cell.

The inhibition of the expression of SMS2 can be carried out by utilizing a ribozyme or a DNA encoding a ribozyme. A ribozyme refers to an RNA molecule having a catalytic activity. Various ribozymes have various activities. Among them, a study focusing a ribozyme as an enzyme that cleaves an RNA enabled it possible to design a ribozyme that site-specifically cleaves an RNA. Some ribozymes are 400 nucleotides or more such as Group I intron type or M1 RNA included in RNase P, others called as hammer head type and hairpin type have about 40 nucleotides of activity domain (Mokoto Koizumi and Eiko Otsuka, Tanpakushitsu Kakusan Koso [Protein, Nucleic Acid and Enzyme], 1990, 35, 2191).

For example, autocleaving domain of a hammerhead type ribozyme cleaves 3' of C 15 of a sequence G13U14C15, and base-paring of U14 and A9 is important for the activity and it was demonstrated that A15 or U15 instead of C15 can be cleaved (Koizumi, M. et al., FEBS Lett, 1988, 228, 228.). If a ribozyme whose substrate-binding site is complementary to an RNA sequence near its target site is designed, an RNA-cleaving ribozyme which recognizes sequences UC, UU or UA in the target RNA like a restriction enzyme can be made (Koizumi, M. et al., FEBS Lett, 1988, 239, 285., Mokoto Koizumi and Eiko Otsuka, Tanpakushitsu Kakusan Koso [Protein, Nucleic Acid and Enzyme], 1990, 35, 2191., Koizumi, M. et al., Nucl Acids Res, 1989, 17, 7059).

Furthermore, a hairpin type ribozyme is also useful for the purpose of the present invention. The ribozyme is found in, for example, a minus strand of satellite RNA of tobacco ringspot virus (Buzayan, J M., Nature, 1986, 323, 349). It was demonstrated that a target specific RNA cleaving ribozyme can be also made from a hairpin type ribozyme (Kikuchi, Y. & Sasaki, N., Nucl Acids Res, 1991, 19, 6751, Yo Kikuchi, Chemistry and Biology, 1992, 30, 112.). As described above, by specifically cleaving the transcript of a gene encoding SMS2 with a ribozyme, the expression of the gene can be inhibited.

Furthermore, the suppression of the expression of an endogenous gene such as SMS2 can be also carried out by RNA interference (abbreviated as "RNAi", hereinafter) with a double stranded RNA having an identical or similar sequence to its target gene sequence. RNAi is a recently noted technique wherein when a double stranded RNA (dsRNA) is directly taken into a cell, the expression of a gene having a sequence homologous to the dsRNA is suppressed. In a mammalian cell, it is possible to induce RNAi by using a short chain dsRNA (siRNA). RNAi has many advantages over a knockout mouse that the effect is stable, experiment for it is easy, the cost is reasonable or the like. For siRNA, it is also described in detail in other postions herein.

As described above, those skilled in the art can suitably produce the "siRNA" of the present invention based on the base sequences of the genes encoding SMS2 described above which the double stranded RNA targets. As an example, a sense strand of the duplex RNA portion includes, but not limited to, SEQ ID NOs: 1, 3, 5, 7, 9, 11, 13, 15, 17, 21 and 23 or the like. It can be suitably carried out by those skilled in the art within the scope of usual trial to select any contiguous RNA region of the mRNA that is a transcript of SMS2 sequence and then make a double stranded RNA corresponding to the region. It can be also suitably carried out by those skilled in the art with known methods to select an siRNA sequence having a stronger RNAi effect among mRNA sequences that are the transcript of the sequence. In addition, if one strand is known, those skilled can also readily know the base sequence of the other strand (a complementary chain). Those skilled in the art can suitably make an siRNA by using a commercially available nucleic acid synthesizer. Alternatively, for the synthesis of a desired RNA, a usual contract service for synthesis can be used.

Therefore, in one embodiment, the present invention is an siRNA of SMS2 (for example, SEQ ID NO: 79 or 80 which are the full length sequences of SMS2). Such siRNA specifically includes, but not limited to, siRNA of any one selected from the group consisting of the following (a)-(o), which are siRNAs based on the sequences which the prevent inventors have originally designed:

(a) an siRNA wherein one strand of the duplex RNA portion is a base sequence set forth by SEQ ID NO: 1 and the other strand of the duplex RNA portion is a base sequence set forth by SEQ ID NO: 2 <SMS2-i6>;

(b) an siRNA wherein one strand of the duplex RNA portion is a base sequence set forth by SEQ ID NO: 3 and the other strand of the duplex RNA portion is a base sequence set forth by SEQ ID NO: 4 <SMS2-i7>;

(c) an siRNA wherein one strand of the duplex RNA portion is a base sequence set forth by SEQ ID NO: 5 and the other strand of the duplex RNA portion is a base sequence set forth by SEQ ID NO: 6 <SMS2-i8>;

(d) an siRNA wherein one strand of the duplex RNA portion is a base sequence set forth by SEQ ID NO: 7 and the other strand of the duplex RNA portion is a base sequence set forth by SEQ ID NO: 8 <SMS2-i104>;

(e) an siRNA wherein one strand of the duplex RNA portion is a base sequence set forth by SEQ ID NO: 9 and the other strand of the duplex RNA portion is a base sequence set forth by SEQ ID NO: 10 <SMS2-i105>;

(f) an siRNA wherein one strand of the duplex RNA portion is a base sequence set forth by SEQ ID NO: 11 and the other strand of the duplex RNA portion is a base sequence set forth by SEQ ID NO: 12 <SMS2-i106>;

(g) an siRNA wherein one strand of the duplex RNA portion is a base sequence set forth by SEQ ID NO: 13 and the other strand of the duplex RNA portion is a base sequence set forth by SEQ ID NO: 14 <SMS2-i107>;

(h) an siRNA wherein one strand of the duplex RNA portion is a base sequence set forth by SEQ ID NO: 15 and the other strand of the duplex RNA portion is a base sequence set forth by SEQ ID NO: 16 <SMS2-i108>;

(i) an siRNA wherein one strand of the duplex RNA portion is a base sequence set forth by SEQ ID NO: 17 and the other strand of the duplex RNA portion is a base sequence set forth by SEQ ID NO: 18 <SMS2-i109>;

(j) an siRNA wherein one strand of the duplex RNA portion is a base sequence set forth by SEQ ID NO: 21 and the other strand of the duplex RNA portion is a base sequence set forth by SEQ ID NO: 22 <SMS2-i3>;

(k) an siRNA wherein one strand of the duplex RNA portion is a base sequence set forth by SEQ ID NO: 23 and the other strand of the duplex RNA portion is a base sequence set forth by SEQ ID NO: 24 <SMS2-i11>;

(l) an siRNA wherein one strand of the duplex RNA portion is a base sequence set forth by SEQ ID NO: 39 and the other strand of the duplex RNA portion is a base sequence set forth by SEQ ID NO: 40 <SMS2-i1>;

(m) an siRNA wherein one strand of the duplex RNA portion is a base sequence set forth by SEQ ID NO: 41 and the other strand of the duplex RNA portion is a base sequence set forth by SEQ ID NO: 42 <SMS2-i2>;

(n) an siRNA wherein one strand of the duplex RNA portion is a base sequence set forth by SEQ ID NO: 45 and the other strand of the duplex RNA portion is a base sequence set forth by SEQ ID NO: 46 <SMS2-i5>; and (o) an siRNA of any of (a)-(n), wherein one to several nucleotides are added, inserted, deleted or substituted in one or both of the base sequences, and having an activity of suppressing the expression of SMS2.

siRNA in the present invention is not necessarily a pair of double stranded RNA to its target sequence, but can be a mixture of multiple pairs of double stranded RNA toward regions comprising the target sequence. Here, siRNA as a nucleic acid mixture corresponding to a target sequence can be suitably made by those skilled in the art with a commercially available nucleic acid synthesizer and DICER enzyme. Alternatively, for the synthesis of a desired RNA, a usual contract service for synthesis can be used. Here, siRNA of the present invention encompasses so-called "cocktail siRNA". Furthermore, not all nucleotides in the siRNA in the present invention are necessarily ribonucleotide (RNA). That is, in the present invention, one or plurality of ribonucleotide(s) that constitutes siRNA can be a corresponding deoxyribonucleotide. The "corresponding" refers to being same kind of base (adenine, guanine, cytosine, thymine (uracil)) with different sugar structures. For example, a corresponding deoxyribonucleotide to a ribonucleotide having adenine refers to a deoxyribonucleotide having adenine. In addition, the above "plurality" refers to, but not specifically limited to, preferably as small number as about 2-5.

Furthermore, a DNA (a vector) capable of expressing the RNA of the present invention can also be encompassed by preferred embodiment of the nucleic acid of the present invention that is capable of suppressing the expression of SMS2. For example, a DNA (a vector) capable of expressing the double stranded RNA of the present invention is a DNA having a structure wherein a DNA encoding one strand of the double stranded RNA and a DNA encoding the other strand of the double stranded RNA are liked to promoters so that each of the DNA can be expressed.

Those skilled in the art can suitably make the DNA of the present invention by general genetic engineering techniques. More specifically, the expression vector of the present invention can be made by suitably inserting a DNA encoding the RNA of the present invention into various known expression vectors.

(A Medicament for a Metabolic Syndrome and a Method for Treating or Preventing a Metabolic Syndrome)

In another aspect, the present invention provides a pharmaceutical composition for treating or preventing a metabolic syndrome, comprising a nucleic acid that suppresses the expression of SMS2. Here, it is understood that as a nucleic acid that suppresses the expression of SMS2 used, any nucleic acid described in (A nucleic acid which suppresses the expression of SMS2) herein can be used.

Alternatively, the present invention provides a nucleic acid (for example, siRNA or an antisense nucleic acid) which suppresses the expression of SMS2 for treating or preventing a metabolic syndrome. It is understood that as a nucleic acid which suppresses the expression of SMS2 used for treating or preventing a metabolic syndrome, any nucleic acid described in (A nucleic acid which suppresses the expression of SMS2) herein can be used.

Preferably, the nucleic acid of the present invention that suppresses the expression of SMS2 is siRNA or an antisense nucleic acid, and the above specific siRNAs or antisense nucleic acids can be exemplified.

In various embodiments, it is understood that a metabolic syndrome which the present invention targets is selected from the group consisting of obesity, diabetes, dyslipidemia and fatty liver. Therefore, when the nucleic acid or medicament of the present invention is used, site to be applied or kind of a disease is not limited as long as the disease is a metabolic disease and it is applied to for example, obesity, diabetes, dyslipidemia and fatty liver or the like as an object. The above disease can be one with which other disease concurrently occurs.

In an embodiment, the medicament of the present invention further comprises a pharmaceutically acceptable excipient. When the composition of the present invention is used as a medicament or pharmaceuticals, the dosage form includes, for example, tablets, powders, fine granules, granules, coated tablets, controlled release formulations, capsules, injections or the like. The pharmaceuticals can comprise an excipient, optionally, additives such as a binding agent, a disintegrating agent, a lubricant, a flavoring agent, a coloring agent, a delayed releasing agent or the like. In a case of an oral formulation, as an excipient, for example, lactose, corn starch, sucrose, glucose, mannitol, sorbite, crystalline cellulose or the like; as a binding agent, for example, polyvinyl alcohol, polyvinylether, methylcellulose, hydroxylpropylcellulose, gum arabic, tragacanth, gelatin, shellac, polyvinylpyrrolidone, block copolymers or the like; as a disintegrating agent, for example, starch, agar, gelatin powder, crystalline cellulose, calcium carbonate, sodium bicarbonate, calcium citrate, dextrin, pectin or the like; as a lubricant, for example, magnesium stearate, talc, polyehylene glycol, silica, hydrogenated vegetable oils or the like; as a flavoring agent, for example, cocoa powder, peppermint oil, cinnamic powder or the like can be used, but not limited thereto. Optionally, it can be coated so as to be a controlled release formulation or enteric coated formulation. In a case of a formulation for injection, a pH modulating agent, a solubilizing agent, an isotonic agent, a buffering agent or the like can be used, but not limited thereto.

The medicament of the present invention can be mixed with a physiologically acceptable carrier, excipient or diluent or the like as above, and orally or parenterally administered as a pharmaceutical composition. As an oral formulation, it can be in dosage forms above such as granules, powders, tablets, capsules, solvents, emulsions, or suspensions. As a parenteral formulation, dosage forms such as injections, drops, medicines for external use, inhalant (nebulizer) or suppository or the like can be selected. As injections, hypodermic injections, intramuscular injections, intraperitoneal injections, intracranial injections, or intranasal injections or the like can be shown. As a medicine for external use, transnasal drugs or ointments or the like can be shown. Technique for formulating the above dosage form so as to comprise the medicament of the present invention as a major ingredient is known.

For example, tablets for oral administration can be made by adding to the nucleic acid or medicament of the present invention an excipient, a disintegrating agent, a binding agent, a lubricant or the like, mixing them and compression molding them. As an excipient, lactose, starch or mannitol or the like are generally used. As a disintegrating agent, calcium carbonate or carboxymethyl cellulose calcium or the like are generally used. As a binding agent, gum arabic, carboxymethyl cellulose or polyvinylpyrrolidone is used. As a lubricant, talc or magnesium stearate or the like are known.

Tablets comprising the nucleic acid or medicament of the present invention can be made with known coating so as to make them to be masked or a enteric coated formulation. As a coating agent, ethylcellulose or polyoxyethylene glycol or the like can be used.

Injections can be also obtained by dissolving the nucleic acid or medicament of the present invention as a major ingredient with a suitable dispersing agent, or dissolving or dispersing them in a disperse medium. Depending on selecting the disperse medium, any dosage form of an aqueous solvent or an oily solvent can be taken. For making an aqueous solvent, a distilled water, a saline, or Ringer's solution or the like are used as a disperse medium. For an oily solvent, various vegetable oils or propylene glycol or the like is used as a disperse medium. In such a case, preservative agents such as paraben or the like can be optionally added. Into injections, known isotonic agents such as sodium chloride or glucose or the like can be also added. Furthermore, analgesics such as benzalkonium chloride or procaine hydrochloride can be added.

The nucleic acid or medicament of the present invention can be also made to be a medicament for external use by making it to be a solid, liquid or semi-solid composition. A solid or liquid composition can be made as a medicament for external use by making them to be similar to the composition as described above. A semi-solid composition can be prepared by optionally adding a thickening agent to a suitable solvent. For the solvent, water, ethyl alcohol or polyethylene glycol or the like can be used. For a thickening agent, bentonite, polyvinyl alcohol, acrylic acid, methacrylic acid, or polyvinylpyrrolidone or the like are generally used. To the composition, a preservative agent such as benzalknoum hydrochloride or the like can be added. It can also be made to be a suppository by combining with, as a carrier, a oily substrate such as cacao butter or an aqueous gel substrate such as cellulose derivatives.

When the nucleic acid or medicament of the present invention is used as a gene therapic agent, a method of directly administering the nucleic acid or medicament of the present invention by an injection, as well as a method of administering a vector wherein the nucleic acid is incorporated are listed. As the vector, an adenoviral vector, an adeno-associated viral vector, a herpesviral vector, a vaccinia viral vector, a retroviral vector, a lentiviral vector or the like are listed, and it can be effectively administerd by using these viral vectors.

It is also possible to introduce the nucleic acid or medicament of the present invention into a phospholipid vesicle such as a liposome and administer it. A vesicle retaining an siRNA or shRNA can be introduced into a given cell by lipofection method. Then, the cell thus obtained is administered systemically, for example, intravenously, intraarterially or the like. It can be also administered locally to site or the like of obesity, diabetes, dyslipidemia and fatty liver. Since siRNA exerts a highly excellent effect of specific and post-transcriptional suppression in vitro but is quickly degraded by a nuclease activity in a serum and has limited duration time in vivo, a more optimal and effective delivery system has been sought to be developed. As one example, by Ochiya, T et al; Nature Med., 5: 707-710, 1999, Curr. Gene Ther., 1:31-52, 2001, it was reported that when atelocollagen that is a biocompatible material is mixed with a nucleic acid to form a complex, it has a effect of protecting the nucleic acid from degrading enzymes in vivo and thus is a carrier which is very suitable as a carrier for an siRNA. Therefore, such a form can be used, but a method for introducing the nucleic acid or medicament of the present invention is not limited thereto. Since it is not degraded in vivo quickly by nucleic acid degrading enzymes in a serum, lasting a long term effect can be achieved in such a way. For example, in Takeshita F. PNAS. (2003) 102(34) 12177-82, Minakuchi Y Nucleic Acids Research(2004) 32(13) e109, it was reported that atelocollagen derived from a bovine skin forms a complex with a nucleic acid and has an effect of protecting the nucleic acid from degrading enzymes in vivo, which is thus very suitable as a carrier for an siRNA. Such techniques can be used.

The nucleic acid or medicament of the present invention is administered to a mammal including a human in a necessary amount (an effective amount) which is within the scope of dosage amount that is deemed as safe. The dosage amount for the nucleic acid or medicament of the present invention can be suitably determined, ultimately by the judgment of a doctor or vetenarian in view of the kind of dosage form, administration method, age or body weight of a patient, symptom of a patient or the like. As an example, although it varies depending on age, sex, symptom, route for administration, times of administration, dosage form, for example, the dosage amount in a case of an adenovirus is about $10^6$-$10^{13}$ per one administration per day and is administered at interval of a week-8 weeks.

It is also possible to use a commercially available kit for transgenesis (for example, Adeno Express: Clontech) in order to introduce an siRNA or shRNA into a tissue or organ of interest.

The medicament or pharmaceutical composition of the present invention can further comprise an effective ingredient. Such additional medicaments that can be comprised are variously considered depending on its purpose.

In another aspect, the present invention provides use of a nucleic acid (for example, siRNA, antisense nucleic acid) that suppresses the expression of SMS2 of the present invention for the manufacture of a medicament for treating or preventing a metabolic syndrome. Here, it is understood that as a nucleic acid that suppresses the expression of SMS2 of the present invention, any nucleic acid described in the above section of (A nucleic acid which suppresses the expression of SMS2) or the present section of (A medicament for a metabolic syndrome and a method for treating or preventing a metabolic syndrome) can be used.

In another aspect, the method of the present invention is a method for manufacturing a pharmaceutical composition or medicament for treating or preventing a metabolic syndrome comprising a nucleic acid that suppresses the expression of SMS2, comprising mixing the nucleic acid that suppresses the expression of SMS2 with a pharmaceutically acceptable excipient. Besides a medicament form, food, health food, functional food or the like which are approved by the authorities can be similarly manufactured. In such cases, in place of a pharmaceutically excipient, a secondary ingredient can be used depending on its purpose.

An effective amount of the medicament or pharmaceutical composition of the present invention refers to an amount in which the medicament or pharmaceutical composition of the present invention can exert an intended pharmaceutical efficacy, and the smallest concentration among such effective amounts is sometime referred herein as a minimal effective amount, which can be suitably determined by those skilled in the art based on the description of the present specification. For determining such effective amounts, besides actual administration, animal model or the like can be used. The present invention is also useful in determining such effective amounts.

In a further aspect, the present invention provides a method for treating or preventing a metabolic syndrome, said method comprising: administering the nucleic acid (for example, siRNA, antisense nucleic acid) that suppresses the expression of SMS2 of the present invention to a subject in need of said treatment or prevention. Here, it is understood that as a nucleic acid that suppresses the expression of SMS2 which can be used, any nucleic acid described in the above section of (A nucleic acid which suppresses the expression of SMS2) or the present section of (A medicament for a metabolic syndrome and a method for treating or preventing a metabolic syndrome) can be used.

Administration to an individual is as explained in the present section of (A medicament for a metabolic syndrome and a method for treating or preventing a metabolic syndrome), any method can be used for it, and it can be generally carried out by methods known to those skilled in the art, for example, intraarterial injection, intravenous injection, hypodermic injection or the like. Dosage amounts vary depending on body weight or age of a patient, administration method or the like, but those skilled in the art (doctors, veterinarians, pharmacists or the like) can suitably select a reasonable dosage amount.

An individual that is an object for the method for treatment or prevention of the present invention is not specifically limited as long as it is an organism that can develop a metabolic syndrome, but preferably a human.

The amount of an effective ingredient used in the method for treatment or prevention of the present invention can be readily determined by those skilled in the art by taking into consideration purpose of use, objective diseases (kind, severity or the like), age, body weight, sex, anamnesis of a patient, form or kind of cell, or the like. Frequency at which the method of treatment of the present invention is carried out on a subject (or a patient) can be also readily determined by those skilled in the art in view of purpose of use, objective diseases (kind, severity or the like), age, body weight, sex, anamnesis of a patient, course of treatment or the like. Such frequency includes, for example, administration once per day to once per several months (for example, once per week to once per month). It is preferable to carry out administration once per day to once per month with observing the course.

Type and amount of ingredients used in the method of treatment of the present invention can be readily determined by those skilled in the art in view of purpose of use, objective diseases (kind, severity or the like), age, bodyweight, sex, anamnesis of a patient, form or kind of site of a patient to be administered or the like, based on information obtained by the method of the present invention (for example, information regarding a disease). Frequency at which the method of monitoring of the present invention is administered on a subject (or a patient) can be also readily determined by those skilled in the art in view of purpose of use, objective diseases (kind, severity or the like), age, body weight, sex, anamnesis of a patient, course of treatment or the like. Frequency for monitoring a status of a disease includes, for example, monitoring once per day to once per several months (for example, once per week to once per month). It is preferable to carry out monitoring once per day to once per month with observing the course.

The present invention can be used as a kit or the like, in such a case, it can be accompanied with written instructions. "Written instructions" herein refers to ones wherein the method of treatment of the present invention is described to a human who carries out the administration such as a doctor, a patient or the like. The written instructions describe, for example, a statement that instructs to suitably administer the medicament or the like of the present invention. The written instructions are made according to the form which is defined by the authorities of a country in which the present invention is carried out (for example, Ministry of Health, Labour and Welfare in Japan, Food and Drug Administration in the United State of America (FDA) or the like), and explicitly describes that it is approved by the authorities. The written instructions is so-called appendant document (package insert), which is usually provided in paper media but not limited thereto, and can be provided, for example, in forms such as electronic media (for example, homepages provided by internet, electronic mail).

(General Techniques)

Techniques of manufacturing a medical devise, techniques of formulation, techniques of microfabrication, molecular biological methods, biochemical methods, microbiological methods, saccharide chain related methods used in herein are well known and routine in the art, and described in for example, Maniatis, T. et al. (1989) Molecular Cloning: A Laboratory Manual, Cold Spring Harbor and 3rd Ed. (2001); Ausubel, F. M., et al. eds, Current Protocols in Molecular Biology, John Wiley & Sons Inc., NY, 10158 (2000); Innis, M. A. (1990) PCR Protocols: A Guide to Methods and Applications, Academic Press; Innis, M. A. et al. (1995) PCR Strategies, Academic Press; Sninsky, J. J. et al. (1999) PCR Applications: Protocols for Functional Genomics, Academic Press; Gait, M. J. (1985) Oligonucleotide Synthesis: A Practical Approach, IRL Press; Gait, M. J. (1990) Oligonucleotide Synthesis: A Practical Approach, IRL Press; Eckstein, F. (1991) Oligonucleotides and Analogues: A Practical Approac, IRL Press; Adams, R. L. et al. (1992) The Biochemistry of the Nucleic Acids, Chapman & Hall; Shabarova, Z. et al. (1994) Advanced Organic Chemistry of Nucleic Acids, Weinheim; Blackburn, G. M. et al. (1996) Nucleic Acids in Chemistry and Biology, Oxford University Press; Hermanson, G. T. (1996) Bioconjugate Techniques, Academic Press; Method in Enzymology 230, 242, 247, Academic Press, 1994; Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997 or the like, relevant portions (that can be all) of which are incorporated herein by reference.

Methods of culture used in the present invention are described and supported in for example, Dobutsu Baiyo Saibo Manyuaru [Animal Cultured Cell Manual], Seno et al. ed., Kyoritsu Syuppan, 1993 or the like, the entire description of which are incorporated herein.

Hereinabove, the present invention has been described with showing preferred embodiments for easiness of understanding. While the present invention is described hereinbelow based on examples, the above description and the examples below are provided for illustrative purpose only, but not provided for a purpose for limiting the present invention. Therefore, the scope of the present invention is not limited by embodiments or examples that are specifically described herein, but limited only by the Claims.

EXAMPLES

Handling animals used in the examples below were in accordance with the criteria defined in Hokkaido University.

Abbreviations used are as follows:
SMS: sphingomyelin synthetase
SMS1, SMS2: names of genes
KO: knockout
wKO: double knockout
MEF: mouse embryonic fibroblast
FBS: fetal bovine serum
DMEM: Dulbecco's modified Eagle medium
TG: triglyceride
SM: sphingomyelin
Me-beta-CD: methyl-beta-cyclodextrin
HFD: high fat diet
ND: normal diet
WAT: white fat cell mass
WT: wild type Example 1

Suppression of Accumulation of Neutral Fat in the Liver by Suppressing SMS2

1) Making SMSs Knockout Mice

As a mouse SMS, three isoforms have been found to date, SMS 1 which was isolated by an expression cloning method, and SMS2 and SMSr which were identified as its homologs. SMS1 knockout (SMS1-KO) mice and SMS2 knockout (SMS2-KO) mice were both made by using the targeting vectors shown in FIG. 1 in accordance with a general method for making a knockout mouse so as to make their exon 1 deficient.

Figure 2:
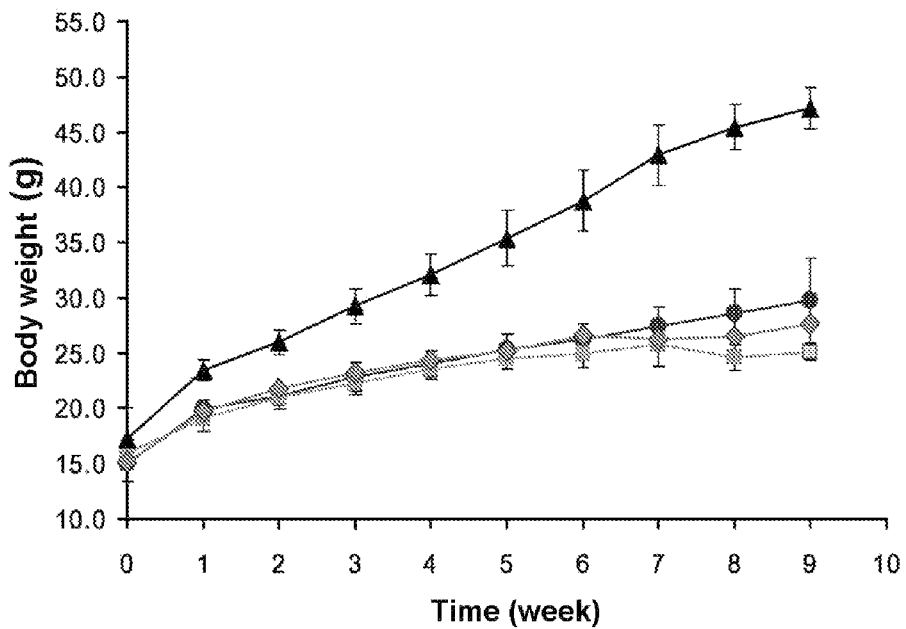
FIG. 2 shows the result in Example 1 wherein the effect of 60% fat diet administration on body weight was investigated. The change of body weight (g) for 9 weeks is shown wherein high fat diet (HFD; 60% fat diet) or control normal diet (ND) were administered to wild type (WT) and SMS2-KO mice. The wild type mice to which high fat diet was administered (WT/HFD) increased their body weight, while in the SMS2-KO mice to which high fat diet was administered (SMS2 KO/HFD), increase in their body weight did not differ from that in wild type mice to which normal diet was administered (WT/ND) and SMS2-KO mice to which normal diet was administered (SMS2 KO/ND) and increase in their body weight was significantly suppressed. Triangle shows WT/HFD; diamond, WT/ND; circle, SMS2 KO/HFD; square, SMS2 KO/ND.

2) Investigation of the Effect of 60% Fat Diet Administration on Body Weight 4 weeks old male wild type mice (WT; C57BL6) and SMS2-KO mice were administered a high fat diet (HFD; 58Y1, testDiet) and a control normal diet (ND; AIN76A, testDiet), respectively, and change in body weight were measured for 9 weeks. As a result, as shown in FIG. 2, when SMS2 KO mice were fed by HFD, increase in body weight was significantly suppressed compared to when similar HFD was administered to WT.

3) Investigation of the Effect of 60% Fat Diet Administration on White Fat Cell Mass (WAT)

Figure 3:
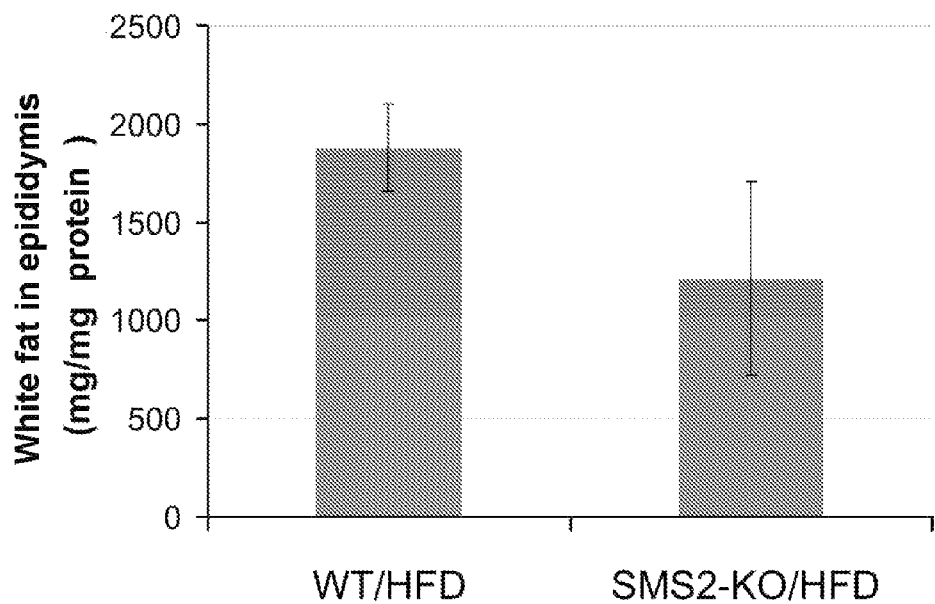
FIG. 3 shows the result in Example 1 wherein the effect of 60% fat diet administration on white fat cell mass (WAT) was investigated. The comparison of weight (mg) of fat attached to epididymis is shown between wild type (WT) and SMS2-KO mice to which high fat diet (HFD; 60% fat diet) were administered for 12 weeks. Compared to WT/HFD group (left), white fat cell mass (WAT) appeared to tend to decrease in SMS2 KO/HFD group (right), which was not a significant difference. Although not shown in the Figure, a similar experiment wherein a control normal diet (ND) was fed in parallel was also carried out. In the latter experiments, white fat cell mass (WAT) was decreased in SMS2 KO/HFD group compared to WT/HFD group, on the other hand, any significant difference was not found between the SMS2 KO/HFD group and the SMS2 KO/ND group.

WT and SMS2 KO mice to which HFD were administered similarly to 2) (12 weeks later) were subjected to abdominal section, and fat attached to epididymis was obtained and then the weights were measured. As a result, as shown in FIG. 3, in SMS2 KO/HFD, white fat cell mass (WAT) appeared to tend to decrease, which was not a significant difference. Although not shown in the Figure, a similar experiment wherein a control normal diet (ND) was fed in parallel was also carried out. In the latter experiments, white fat cell mass (WAT) was decreased in the SMS2 KO/HFD group compared to the WT/HFD group, on the other hand, any significant difference was not found between the SMS2 KO/HFD group and the SMS2 KO/ND group.

Figure 4:
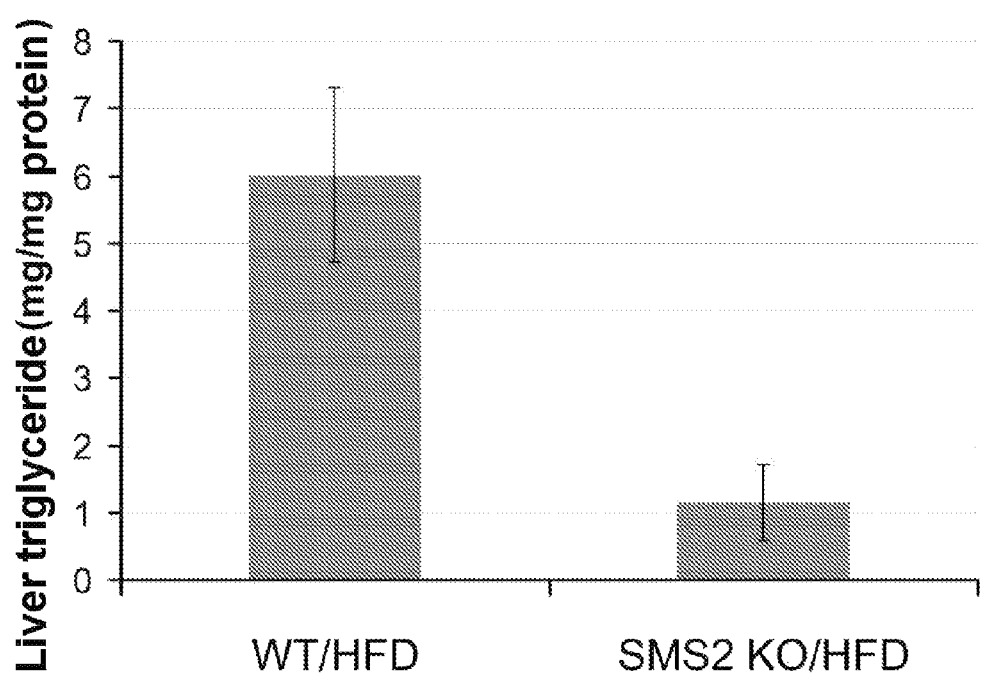
FIG. 4 shows the result in Example 1 wherein the effect of 60% fat diet administration on liver triglyceride amount was investigated. The comparison of triglyceride amount in liver homogenate (mg/mg protein) is shown between wild type (WT) and SMS2-KO mice to which high fat diet (HFD; 60% fat diet) were administered for 12 weeks. Compared to the WT/HFD group (left), the triglyceride amount was significantly decreased in the SMS2 KO/HFD group (right).

4) Investigation of the Effect of 60% Fat Diet Administration on Liver Triglyceride Amount WT and SMS2 KO mice to which HFD were administered similarly to 2) (12 weeks later) were subjected to abdominal section, and the livers thereof were obtained. Triglyceride in the liver homogenate were quantified by Triglyceride Quantification Kit (Biovision). The methods were in accordance with the writen instructions of the kit. The protein amount in the homogenate was quantified with BCA protein assay (Pierce) and used for correction of triglyceride amounts. As a result, as shown in FIG. 4, compared to the WT/HFD group, the triglyceride amount was significantly decreased in the SMS2 KO/HFD group.

Figure 4A:
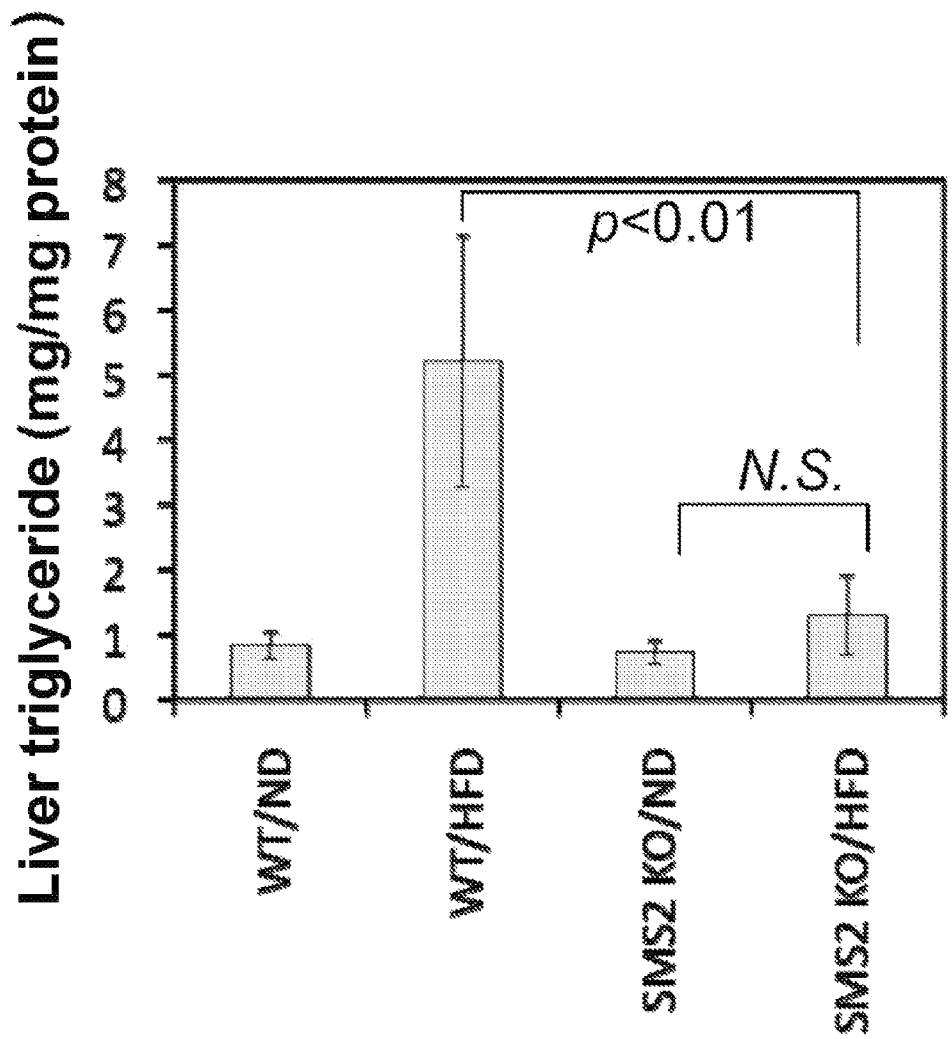
FIG. 4A shows the result in Example 1 wherein the effect of 60% fat diet administration on liver triglyceride amount was investigated. The comparison of triglyceride amount in liver homogenate (mg/mg protein) is shown between wild type (WT) and SMS2-KO mice to which high fat diet (HFD; 60% fat diet) or control normal diet (ND) were administered for 12 weeks. Compared to WT/HFD group (left), the triglyceride amount was significantly decreased in SMS2 KO/HFD group (right). On the other hand, any significant difference was found between SMS2 KO/HFD group and SMS2 KO/ND group.

Furthermore, the result of comparing triglyceride amount in liver homogenate (mg/mg protein) is shown in FIG. 4A between wild type (WT) and SMS2-KO mice to which a high fat diet (HFD; 60% fat diet) or a control normal diet (ND) were administered for 12 weeks. As a result, as shown in FIG. 4A, compared to the WT/HFD group (left), the triglyceride amount was significantly decreased in the SMS2 KO/HFD group (right). On the other hand, any significant difference was not found between the SMS2 KO/HFD group and the SMS2 KO/ND group.

5) Investigation of the Effect of 60% Fat Diet Administration on Adiponectin Amount WT and SMS2 KO mice to which HFD were administered similarly to 2) (12 weeks later) were subjected to abdominal section, and fat attached to epididymis was obtained, mRNA thereof was extracted and then the mRNA expression amount of adiponectin was measured by QPCR (Thermal Cycler Dice TP800, TAKARA BIO INC.). At that time, correction was made with the mRNA expression amount of GAPDH in the same samples. As reagents, PrimeScript RT-reagent Kit (TAKARA BIO INC.) was used for the first strand cDNA synthesis and SYBR premix EX Taq II (TAKARA BIO INC.) was used for QPCR. As PCR primers,

```
                                   (SEQ ID NO: 25)
    Fw primer:    GTCAGTGGATCTGACGACACCAA;

(SEQ ID NO: 26)
    Rv primer:    ATGCCTGCCATCCAACCTG
``` were used.

Figure 5:
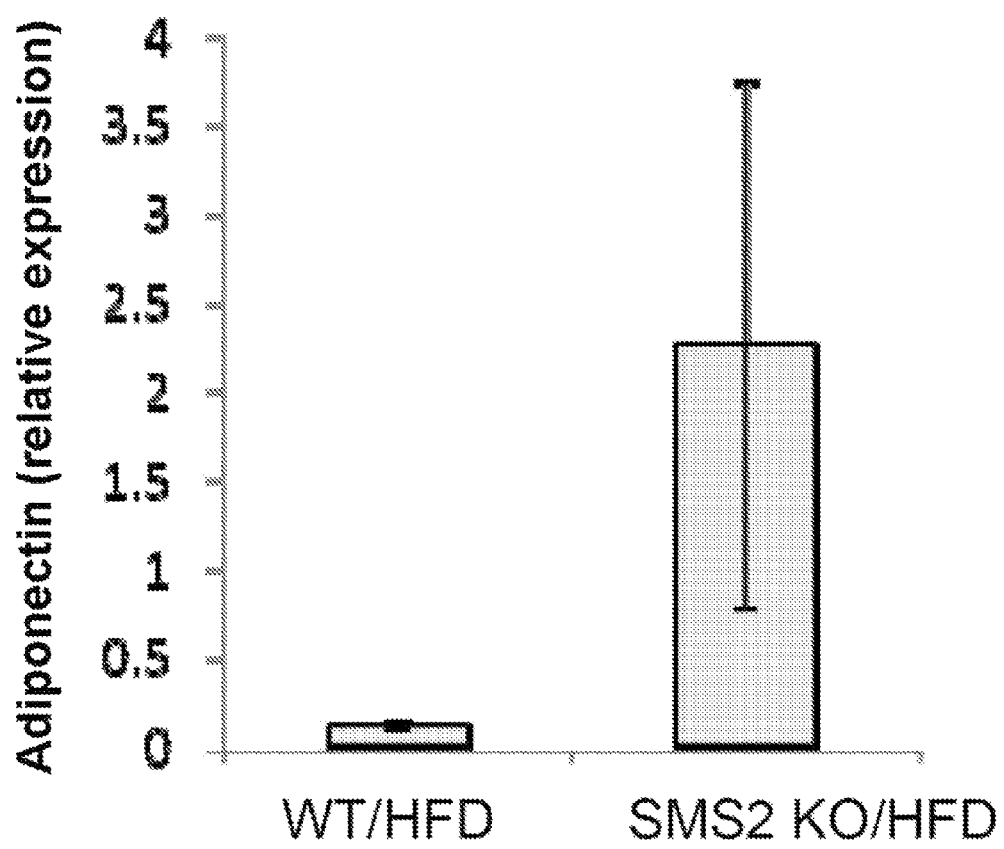
FIG. 5 shows the result in Example 1 wherein the effect of 60% fat diet administration on adiponectin amount was investigated. The comparison of relative expression amount of adiponectin mRNA in adipose tissue is shown between wild type (WT) and SMS2-KO mice to which high fat diet (HFD; 60% fat diet) were administered for 12 weeks. The expression of adiponectin was suppressed in WT/HFD group (left), while a relatively high expression amount was maintained in SMS2 KO/HFD group (right).
Figure 5A:
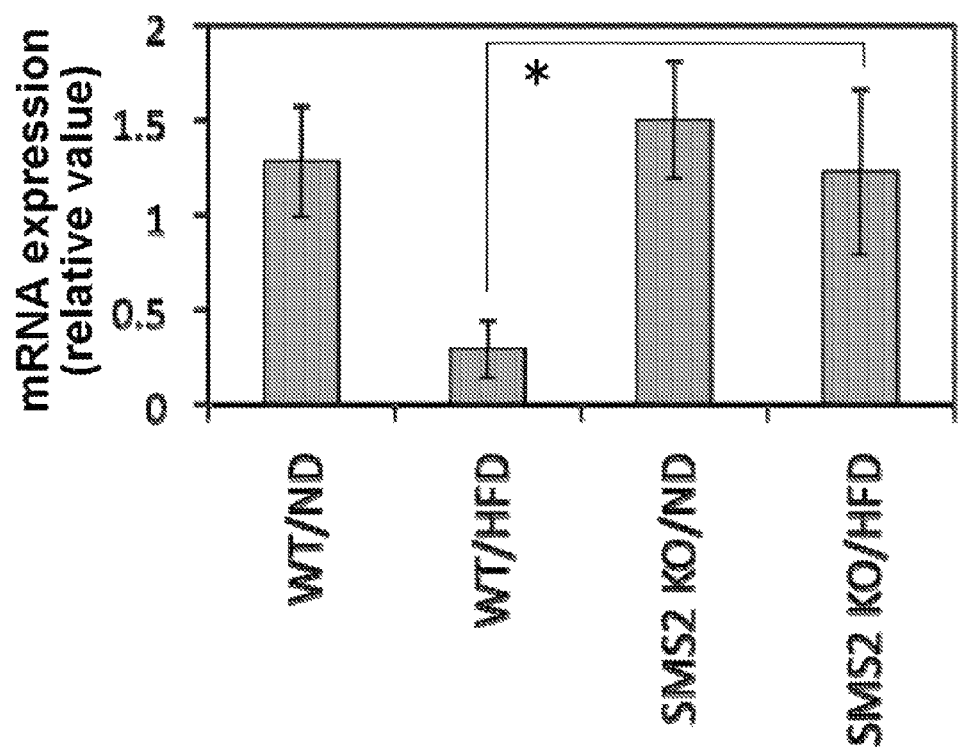
FIG. 5A shows the result in Example 1 wherein the effect of 60% fat diet administration on adiponectin amount was investigated. The comparison of relative expression amount of adiponectin mRNA in adipose tissue is shown between wild type (WT) and SMS2-KO mice to which high fat diet (HFD; 60% fat diet) or control normal diet (ND) were administered for 12 weeks.

As a result, as shown in FIG. 5, the expression of adiponectin was suppressed in the WT/HFD group, while a relatively high expression amount was maintained in the SMS2 KO/HFD group. Furthermore, relative expression amount of adiponectin was compared between wild type (WT) and SMS2-KO mice to which a high fat diet (HFD; 60% fat diet) or a control normal diet (ND) were administered for 12 weeks. As a result, as shown in FIG. 5A, in the WT group, by feeding the high fat diet, the expression of adiponectin was suppressed, while in the SMS2 KO group, even when the high fat diet was fed, a relatively high expression amount was maintained.

From the above results, it was found that there was possibility that the accumulation of neutral fat in the liver is suppressed by suppressing SMS2.

6) Experiments Regarding Insulin Resistance

6-1) Expression Analysis of an Insulin Receptor

Next, mRNA expression amount of an insulin receptor in adipose tissues in WT and SMS2KO mice was analyzed by a quantitative PCR. The relative expression amount of insulin receptor was investigated when wild type (WT) and SMS2-KO mice were administered a high fat diet (HFD; 60% fat diet) or a control normal diet (ND). The primer sequence and control primer sequence used are shown. The quantitative PCR was carried out in the same way as described in 5).

Insulin Receptor (IR)

```
                                   (SEQ ID NO: 27)
    Forward (Fw):     CAGCTCGAAACTGCATGGTTG (SEQ ID NO: 28)
    Reverse (Rv):     GGTGACATCCACCTCACAGGAA
```

Figures 1, 5B:
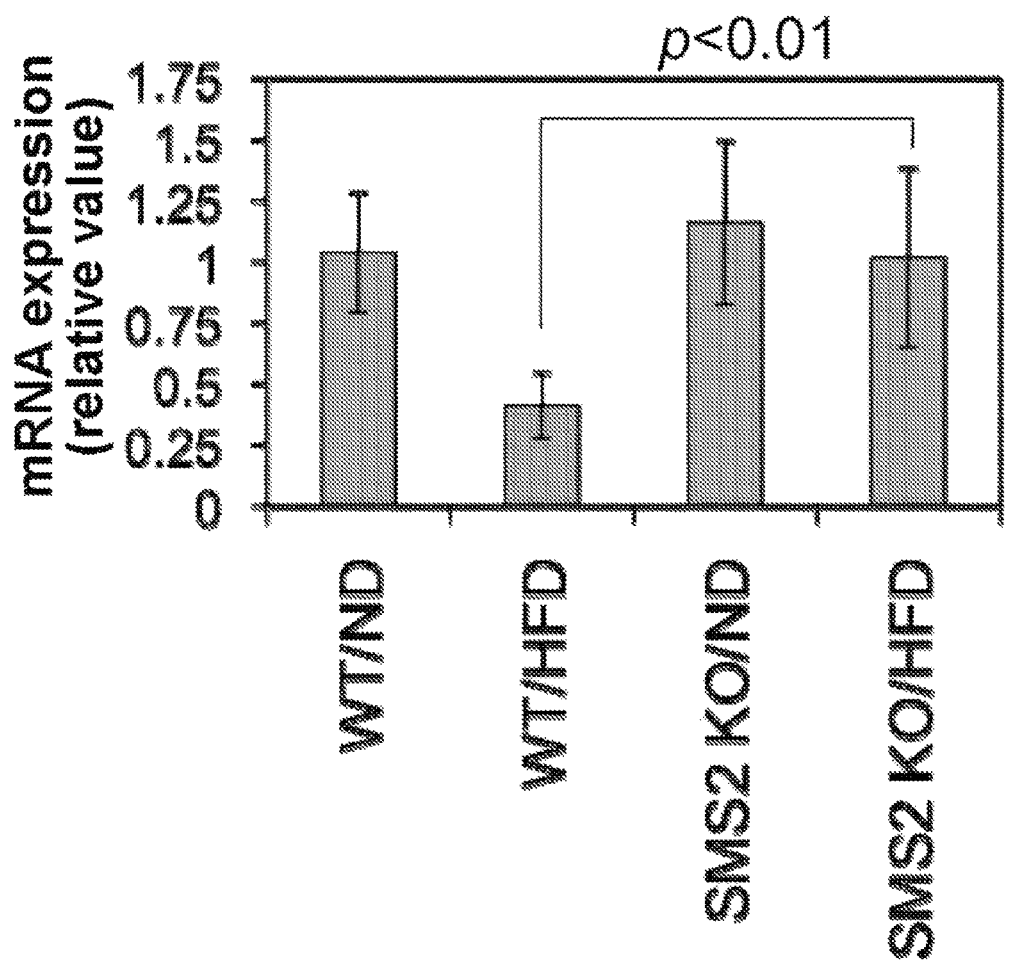
Figures 2, 5B:
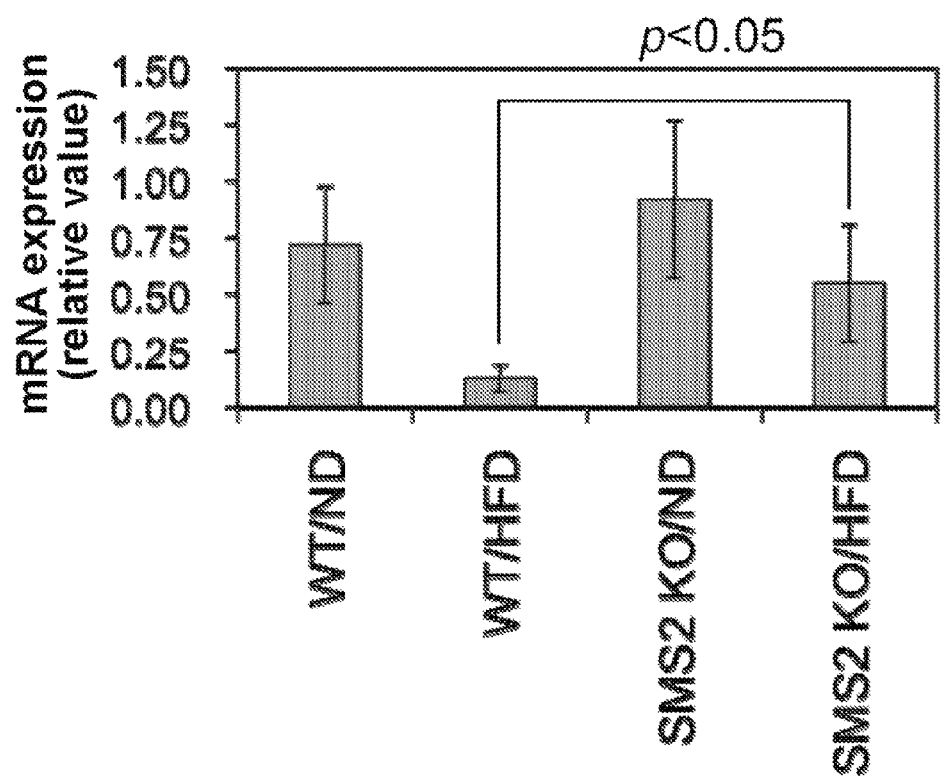

The result is shown in FIG. 5B-1. As shown in FIG. 5B-1, in the wild type mice, when a high fat diet (HFD; 60% fat diet) was fed, the expression amount of insulin receptor decreased. On the other hand, in the SMS2-KO mice, decrease in the expression of insulin receptor by the high fat diet did not occur and it was an almost similar expression amount to that of a case which the control normal diet was fed. In addition, the expression amount of insulin receptor when the high fat diet was administered to the SMS2-KO mice was significantly higher compared to when the high fat diet was administered to the wild type mice.

From above, in the SMS2-KO mice, decrease in expression of an insulin receptor by HFD as observed in the wild type did not occur and the expression amount was almost similar to that with ND. From the above results, it was suggested that in adipose tissues of the SMS2-KO mice, decrease in the expression of insulin receptor by HFD as observed in the WT did not occur, and thus the SMS2-KO mice did not become insulin resistance (FIG. 5B-1).

6-2) Expression Analysis of Glut4

Next, the effect of 60% fat diet administration on Glut4 in adipose tissues was investigated. The relative expression amount of Glut4 was compared between a wild type (WT) and SMS2-KO mice to which a high fat diet (HFD; 60% fat diet) or a control normal diet (ND) were administered. The primer sequences and control primer sequences used are shown.

GLUT4:

```
                                   (SEQ ID NO: 29)
    Forward (Fw):     CTGTAACTTCATTGTCGGCATGG
```

```
                                                     (SEQ ID NO: 30)
     Reverse (Rv):           AGGCAGCTGAGATCTGGTCAAAC
```

Hypoxanthine-guanine phosphoribosyltransferase (HPRT) that is an endogenous control gene:

```
                                                      (SEQ ID NO: 7)
     Forward (Fw):           TTGTTGTTGGATATGCCCTTGACTA (SEQ ID NO: 8)
     Reverse (Rv):           AGGCAGATGGCCACAGGACTA.
```

The result is shown in FIG. 5B-2. As apparent from FIG. 5B-2, In the wild type mice, when a high fat diet (HFD; 60% fat diet) was fed, the expression amount of Glut4 was decreased, while in the SMS2-KO mice, the degree of decrease in the expression of Glut4 by a high fat diet was suppressed and it was a almost similar expression amount to that of a case which a control normal diet was fed. In addition, the expression amount of Glut4 when the high fat diet was administered to the SMS2-KO mice was significantly higher compared to when the high fat diet was administered to the wild type. From the above results, it was suggested that in adipose tissues of the SMS2-KO mice, decrease in the expression of Glut4 by the high fat diet as observed in the wild type mice did not occur, and thus the SMS2-KO mice did not become insulin resistance.

6-3) Glucose Tolerance Test

Figure 5C:
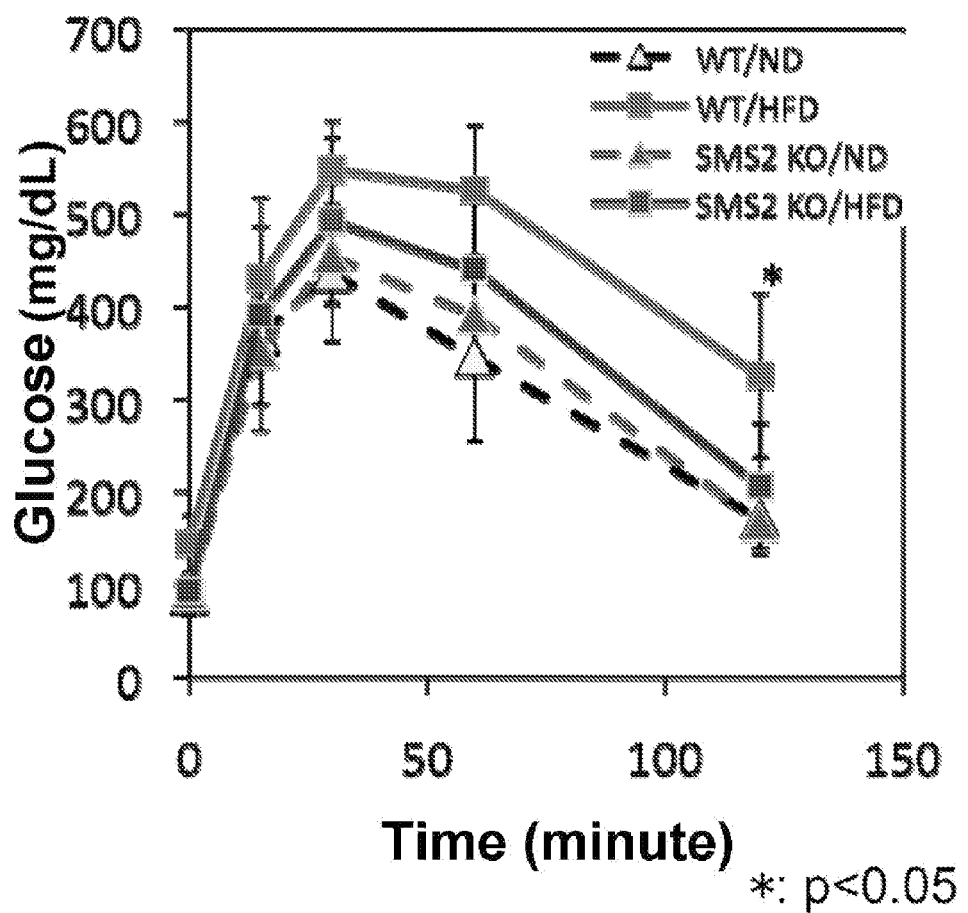
FIG. 5C shows the result in Example 1 wherein the effect of 60% fat diet administration on blood glucose level was investigated. Wild type (WT) and SMS2-KO mice were administered high fat diet (HFD; 60% fat diet) or control normal diet (ND) for 9 weeks, then fasted for 24 hours, then intraperitonealy administered 2 g/kg glucose. Blood glucose levels were measured immediately before administration, 15 minutes after administration, at 30 minutes after administration, at 60 minutes after administration, and at 120 minutes after administration. Immediately before administration, no significant difference existed among the 4 groups, while at 120 minutes after administration, blood glucose level was significantly decreased in SMS2 KO/HFD group compared to in WT/HFD group. White triangle shows WT/ND, thin square shows WT/HFD, triangle that is filled in shows SMS2 KO/ND, and thick square shows SMS2 KO/HFD. Y axis shows blood glucose concentration (mg/dL), and X axis shows time (minute).
Figure 5D:
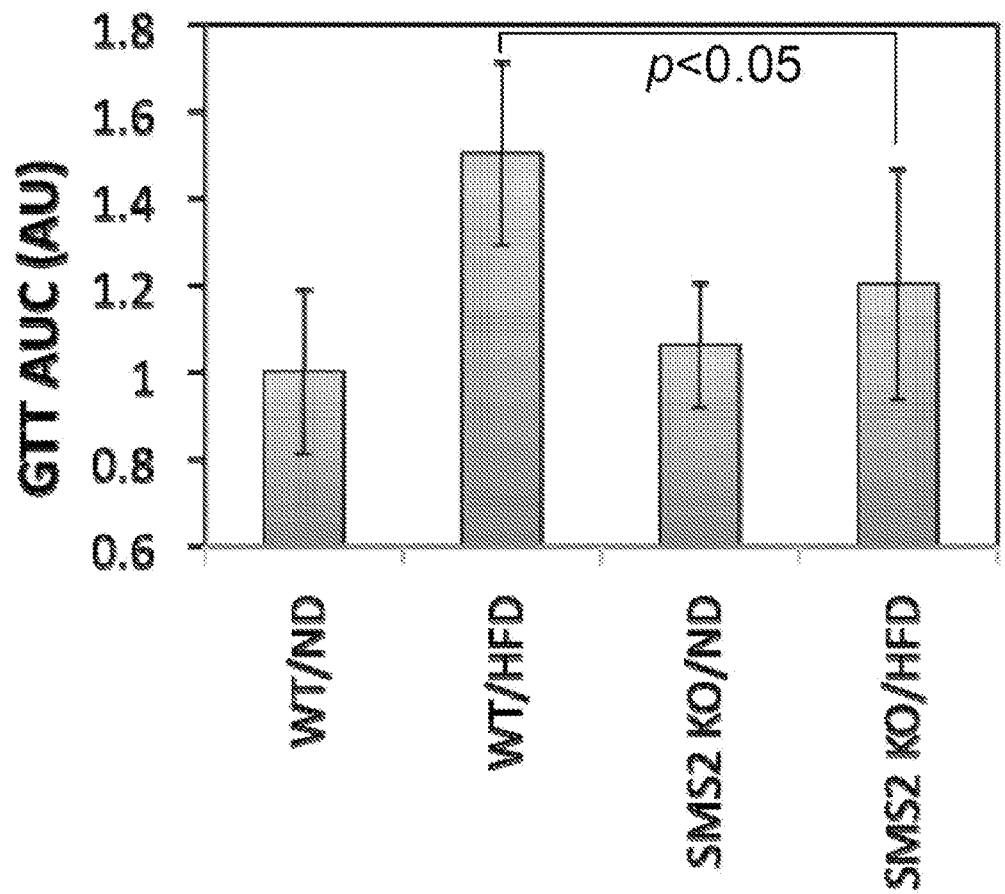
FIG. 5D represents the area under curve of FIG. 5C (AUC) in bar graph. In the order from left, shown are a group wherein wild types were fed by normal diet (WT/ND), a group wherein wild types were fed by high fat diet (WT/HFD), a group wherein SMS2-KO mice were fed by normal diet (SMS2 KO/ND), and a group wherein SMS2-KO mice were fed by high fat diet (SMS2 KO/HFD). A significant difference was recognized between WT/HFD and SMS2 KO/HFD ($p<0.05$). Y axis shows relative values of GTT AUC (area=AU, unit is $m^2$ (area unit)).

The control normal diet (ND) or high fat diet (HFD; 60% fat diet) described in "2) Investigation of the effect of 60% fat diet administration on body weight" above were administered to wild type (WT) or SMS2KO mice. The mice which were further grown for 9 weeks were used for carrying out glucose tolerance test. The mice were fasted for 24 hours and intraperitoneally administered 2 g/kg of glucose. Blood glucose levels were measured in the blood obtained from tail vein immediately before administration, 15 minutes after administration, at 30 minutes after administration, at 60 minutes after administration, and at 120 minutes after administration. For the measurement, a glucometer was used. As a result, it was found between the wild type and SMS2-KO mice to which the high fat diet was administered, that at 120 minutes after administration, the blood glucose level was significantly decreased in the SMS2 KO/HFD group (P<0.05; FIG. 5C). When the areas under curve of the graph of the glucose tolerance test were compared (GTT AUC; FIG. 5D), between the wild type and the SMS2-KO mice to which the high fat diet was administered, the area was significantly decreased in the SMS2-KO mice (P<0.05).

FIG. 5D shows the area under curve (AUC) of FIG. 5C as a bar graph. Also from such expression, it can be understood that blood glucose level was significantly decreased in the SMS2 KO/HFD group compared to the WT/HFD group.

From the results, it could be confirmed that they become significantly sensitive to glucose load.

Figure 5E:
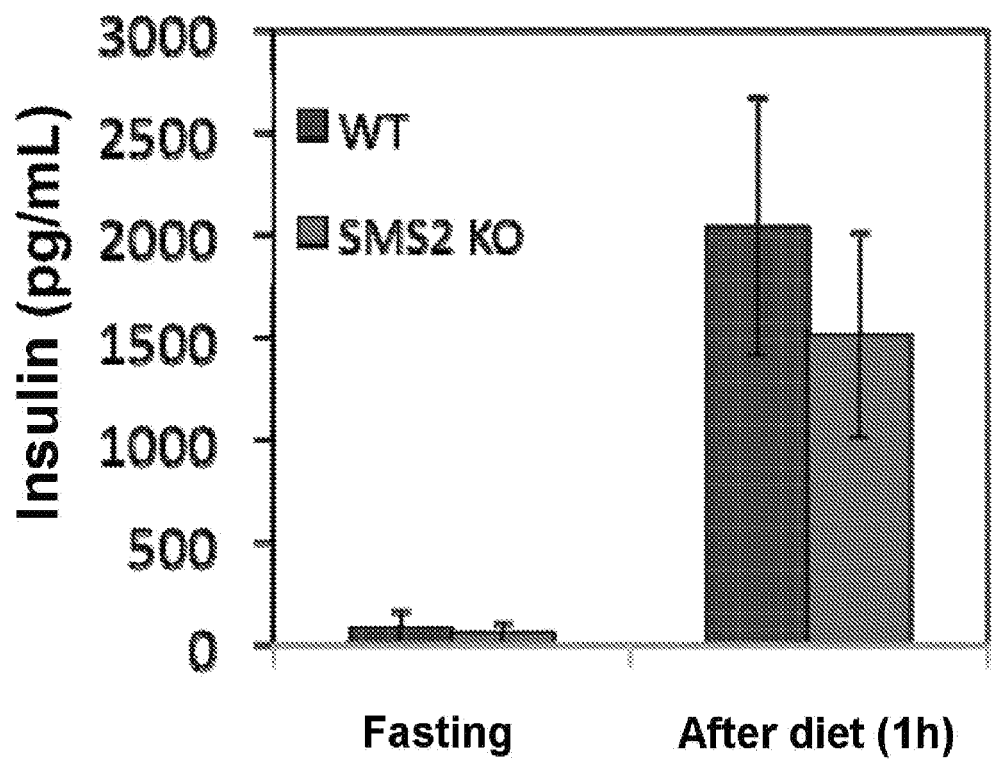
FIG. 5E shows the result in Example 1 wherein the effect of normal diet (ND) on blood insulin amount was investigated. Wild type (WT) and SMS2-KO mice were administered normal diet for 4 weeks, then fasted for 24 hours, then administered normal diet. Blood insulin concentration was measured at 24 hours fasting and 1 hour after normal diet administration. Left shows at fasting and right shows 1 hour after feeding. In each pair, left (thick column) shows wild type (WT) and right (thin column) shows SMS2 KO. Y axis shows blood insulin concentration (pg/ml). Between wild type (WT) and SMS2-KO mice, no significant difference in blood insulin concentration was observed at 24 hours fasting and 1 hour after normal diet administration. From the experiments, it can be said that even if SMS2 is knocked out, the amount of insulin and insulin secretion response itself to feeding are not affected. Therefore, any concern such as decrease in body weight and decrease in blood glucose level which is expected to result from abnormal secretion of insulin due to abnormality of beta cell of pancreas could be solved.

Next, plasma insulin amount was measured. Wild type (WT) and SMS2-KO mice were administered a normal diet from the time of 8 weeks old for 4 weeks, and then fasted for 24 hours, and then administered a normal diet. Blood insulin concentration was measured at 24 hours fasting and 1 hour after the normal diet administration. The results are shown in FIG. 5E. As apparent from FIG. 5E, between the wild type (WT) and SMS2-KO mice, no significant difference in blood insulin concentration was observed at 24 hours fasting and 1 hour after the normal diet administration. Therefore, it can be said that no significant difference in blood insulin concentration and reactivity was observed between the wild type (WT) and SMS2-KO mice. From the results, it could be confirmed that the SMS2-KO mice did not have any abnormality in insulin producing capability and reactivity to glucose, and thus any abnormality in pancreatic beta cell was observed.

Figure 5F:
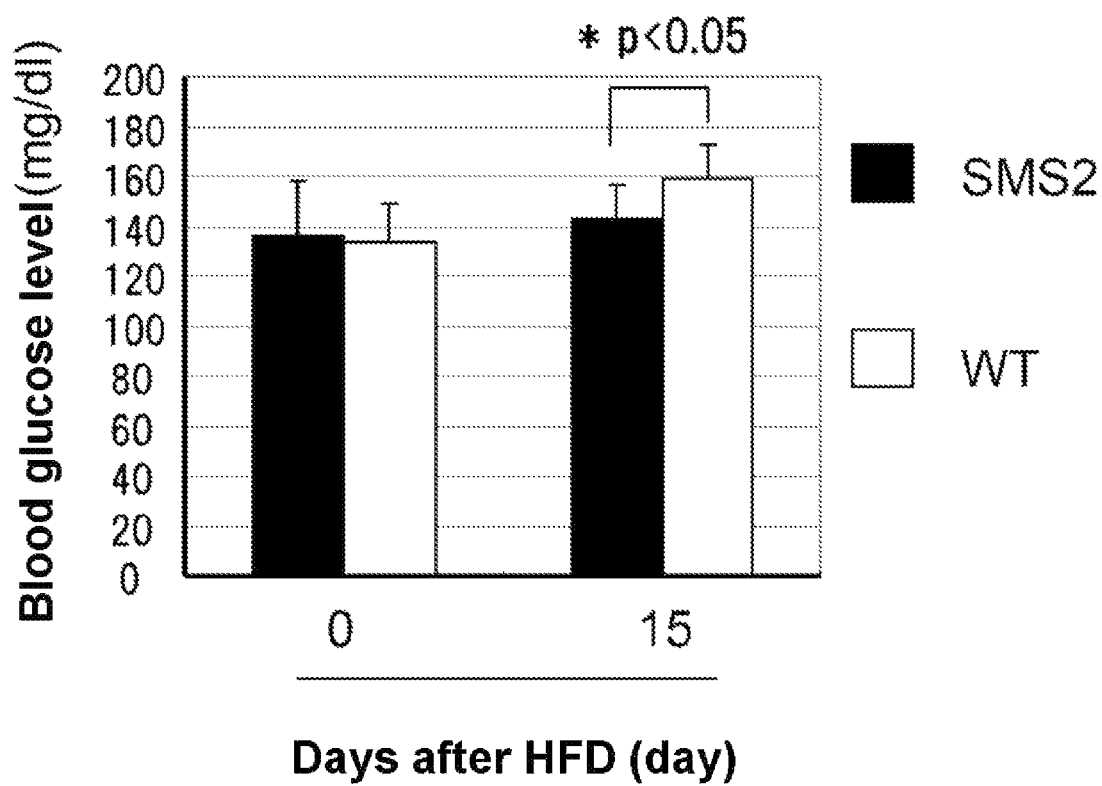
FIG. 5F shows the result in Example 1 wherein the effect of high fat diet on blood glucose level was investigated. 4 weeks old wild type (WT) and SMS2-KO mice were administered high fat diet (HFD; 60% fat diet) for 2 weeks. Blood glucose level was measured at the time of 4 hours fasting before high fat diet administration and at the time of 4 hours fasting after 2 weeks of high fat diet administration. Left group shows Day 0 and right group shows Day 15. Black bars show SMS2-KO mice and white bars show wild type (WT). Y axis shows blood glucose level (mg/dl). Although no significant difference in blood glucose level was observed before administering high fat diet between wild type mice and SMS2-KO mice, blood glucose level in wild type mice was significantly higher compared to in SMS2-KO mice after administering high fat diet for 2 weeks ($p<0.05$). From the results, it is meant that in SMS2-KO mice, blood glucose level was decreased with a significant difference. Combining with the results of FIG. 5E, it can be said that if SMS2 is knocked out, diabetes with insulin resistance does not occur.

Next, the effect of a high fat diet on blood glucose level was investigated. 4 weeks old wild type (WT) and SMS2-KO mice were administered a high fat diet (HFD; 60% fat diet) for 2 weeks. Blood glucose level was measured at the time of 4 hours fasting before the high fat diet administration and at the time of 4 hours fasting after 2 weeks of high fat diet administration. As shown in FIG. 5F, although no significant difference in blood glucose level was observed before administering the high fat diet between the wild type mice and SMS2-KO mice, blood glucose level in the wild type mice was significantly higher compared to in the SMS2-KO mice after administering the high fat diet for 2 weeks.

Figure 5G:
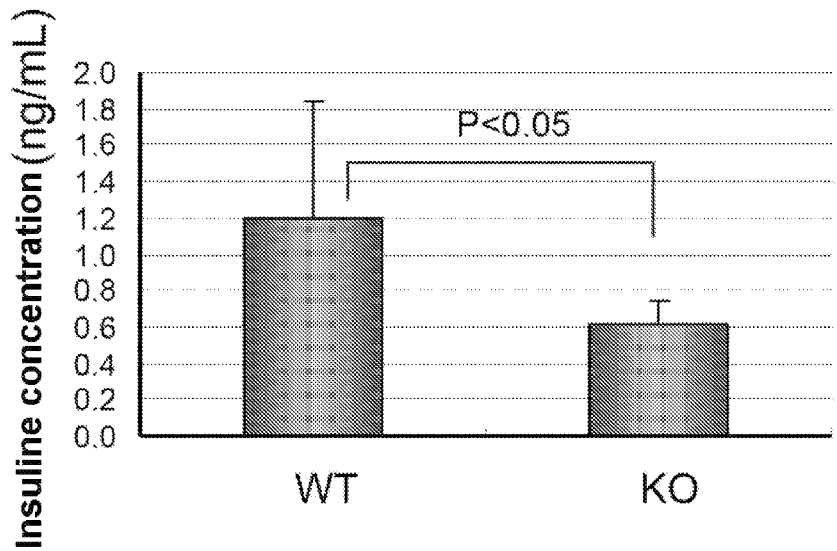
FIG. 5G shows the result in Example 1 wherein the effect of a high fat diet administration on blood insulin amount was investigated. Wild type (WT) and SMS2-KO mice were administered high fat diet (HFD; 60% fat diet) for 2 weeks, and then fasted for 4 hours, and then blood insulin amount was measured. Left shows wild type (WT) and right shows SMS2-KO mice (KO). Y axis shows blood insulin concentration (ng/ml). Consequently, in SMS2-KO mice, blood insulin amount was decreased with a significant difference compared to in wild type mice.

Next, the effect of a high fat diet on blood insulin amount was investigated. Wild type (WT) and SMS2-KO mice were administered a high fat diet (HFD; 60% fat diet) for 2 weeks, then fasted for 4 hours, and then blood insulin amount was measured. As a result, as shown in FIG. 5G, in the SMS2-KO mice, blood insulin amount was decreased with a significant difference compared to in the wild type mice.

Figures 1, 5H:
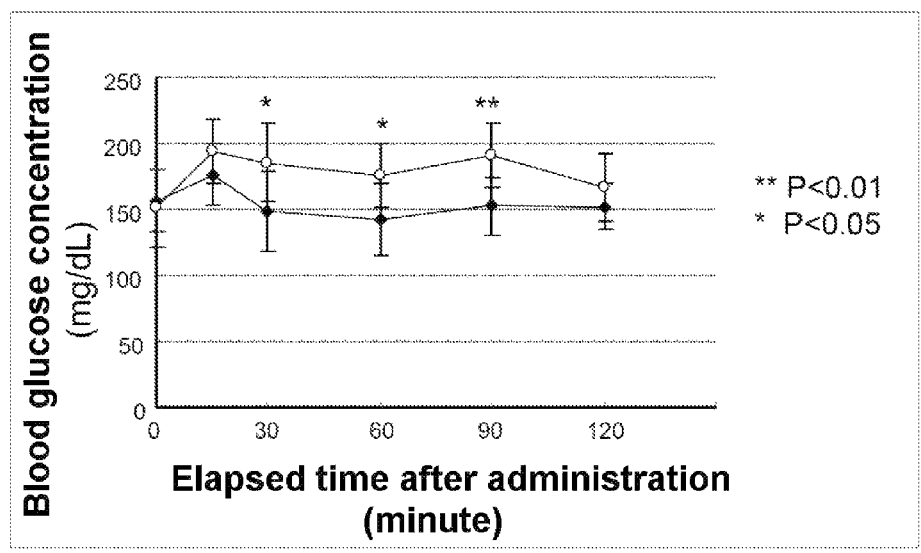
Figures 2, 5H:
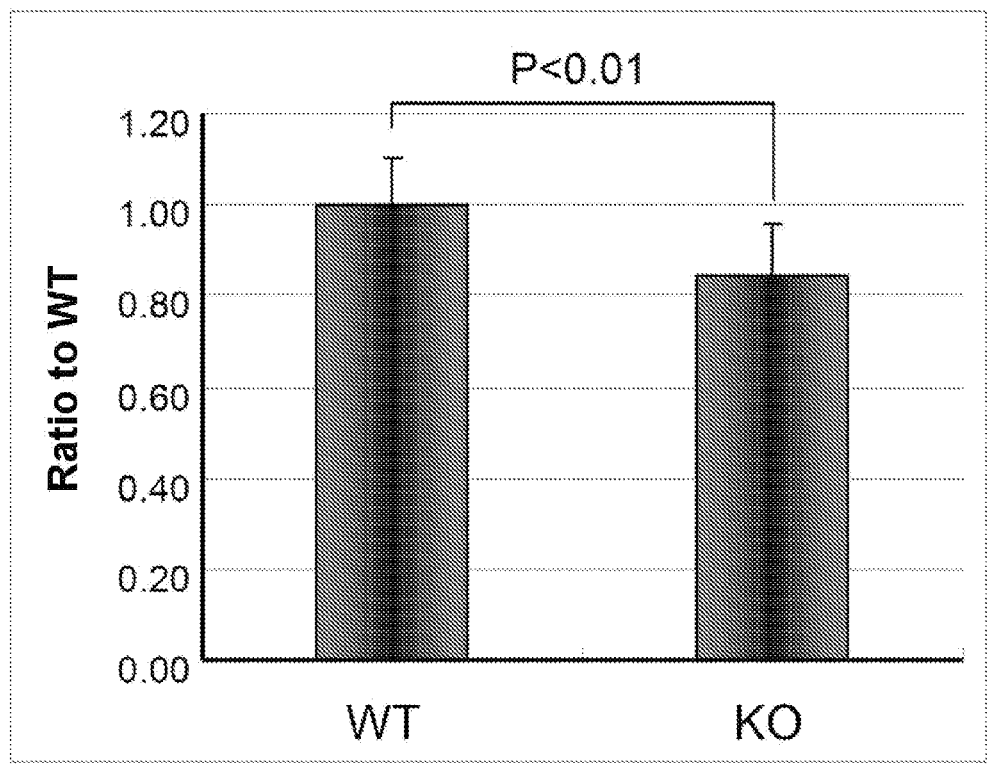

Next, the blood glucose concentration in response to insulin was investigated. 4 weeks old wild type (WT) and SMS2-KO mice were administered a high fat diet (HFD; 60% fat diet) for 6 weeks, and insulin were intraperitoneally administered in 0.5 U/kg. The results of blood glucose concentrations that were measured before administration and at 15, 30, 60, 90 and 120 minutes after administration are shown in FIG. 5H-1. As shown in FIG. 5H-1, in particular, since blood glucose concentration in the SMS2-KO mice was significantly decreased compared to in the wild type mice at 30, 60 and 90 minutes after administration, it became apparent that the SMS2-KO mice were more sensitive to insulin.

As also apparent from FIG. 5H-2 which shows the area under curve (AUC) in FIG. 5H-1, since it was significantly decreased by about 20% in the SMS2-KO mice compared to in the wild type mice, it became apparent that they were more sensitive to insulin.

In the SMS2-KO mice, plasma insulin amount was decreased compared to the WT. It was thus demonstrated that the SMS2KO mice did not become insulin resistance. Therefore, the SMS2-KO mice was sensitive to insulin, and insulin resistance was not raised therein as in the wild type mice (see, in particular, FIG. 5E, FIG. 5F and FIG. 5G).

From the above results, it could be found that there is possibility that diabetes can be treated, in particular, insulin resistance can be ameliorated, by inhibiting SMS2.

Example 2

Production of SMSs-Reconstructed Cells

1) Production of Immortalized MEF Cells

As described in Shin Baiyo Saibo Jikken Ho [New Cultured Cell Experimental Method], Yodosha Co., Ltd., Chapter 4, Shyodai Baiyo Seniga Saibo [A Primary Cultured Fibroblast], p. 66-70, the SMS1-KO mouse and SMS2-KO mouse made in Example 1 were mated and from the thus obtained fetus of double knockout that were deficient in both SMS1 and SMS2 (SMS1, 2-wKO), an MEF (mouse embryonic fibroblast) was isolated. The MEF was infected with a retrovirus that was released into the culture supernatant of 293T cell stably retaining pMFG-SV40Tst, thereby immortalizing MEF.

a) Preparation of a Viral Solution

As a virus producing cell, NIH3T3 ecotroic producer cell psiCRE-MFGtsT (RCB1119; SV40 T antigen-expressing virus producer cell; see, http://www2.brc.riken.jp/lab/cell/detail.cgi?cell_no=RCB1119&type=1) was used. The psi-CRE-MFGtsT cell releases a retrovirus expressing SV40tsT into a medium and it infects a mouse host cell. A subconfluent psiCRE-MFGtsT cell was cultured in a DMEM including 10% FBS overnight under conditions of 37 degrees Celsius, 5% $CO_2$. At the next day, the supernatant was recovered as a viral solution and filtered with a 0.20 mm syringe filter (available from CORNING).

b) Viral Infection and Cloning of Cell Strains

In the culture of MEF, the medium was replaced with 5 mL of DMEM including 10% FBS, 1 mL of the viral solution, it was cultured for 24 hours under conditions of 34 degrees Celsius, 5% $CO_2$ and infected with the virus, then added 5 mL of DMEM including 10% FBS and further cultured overnight. At the next day, the medium was replaced with 10 mL of DMEM including 10% FBS. The medium was exchanged every 2-3 days, and immortalized MEF cell strains were established. Furthermore, some cell strains were cloned from the immortalized MEF and one of them was designated as ZS2.

2) Production of Immortalized MEF Cells that Overexpress SMS1 or SMS2

Figure 6:
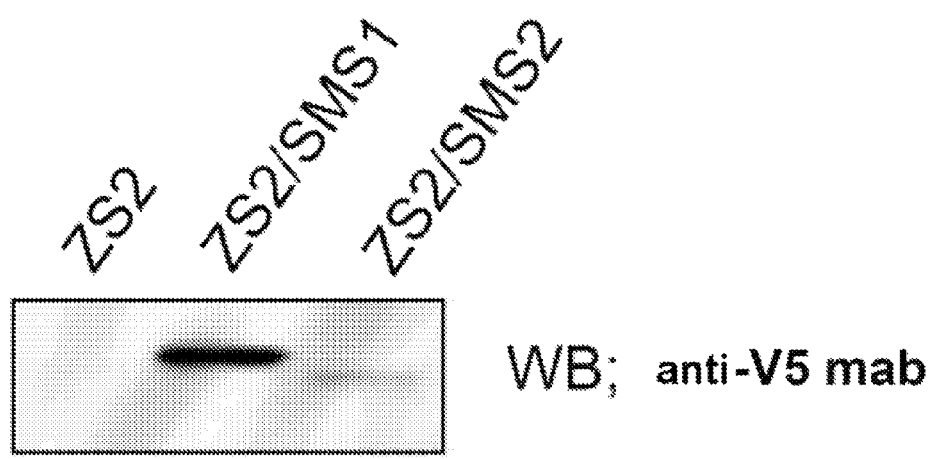
FIG. 6 shows result of Western blotting wherein anti-V5 monoclonal antibody was used on ZS2 cell with SMS1 and SMS2 deleted, SMS1-overexpresing cell (ZS2/SMS1) and SMS2-overexperssing cell (ZS2/SMS2) which were made in Example 2. In ZS2 cell, no band was detected, while in ZS2/SMS 1 and ZS2/SMS2, bands of SMS1 and SMS2 which can be detected with anti-V5 mab were respectively confirmed.

A retroviral vector was made by incorporating SMS1 and SMS2 with a V5 tag at C terminus added into pQCXIP (Clontech). Using this plasmid and GP2-293 cell (Clontech), retroviruses expressing SMS 1 or SMS2, respectively were made and, in accordance with the instructions of Clontech, infected into the ZS2 cell that was one of the cell strains cloned in 1). Uninfected cells were removed with 4 microgram/ml puromycin, cell ZS2/SMS1 that overexpreesed SMS1 and cell strain ZS2/SMS2 that overexpressed SMS2 were obtained. On three these cell strains, a Western blot was carried out with an anti-V5 mab (invitrogen) antibody. In the SMS1 expressing cell and the SMS2 expressing cell, as shown in FIG. 6, bands of SMS 1 or SMS2 which can be detected with the anti-V5 mab were respectively confirmed.

Example 3

Investigation of Function of ZS2, ZS2/SMS1 and ZS2/SMS2 Cells

The function, in particular, SMS activity and TG synthesis, of the ZS2, ZS2/SMS 1 and ZS2/SMS2 cells made in Example 2.

1) An SMS Activity

Figure 7:
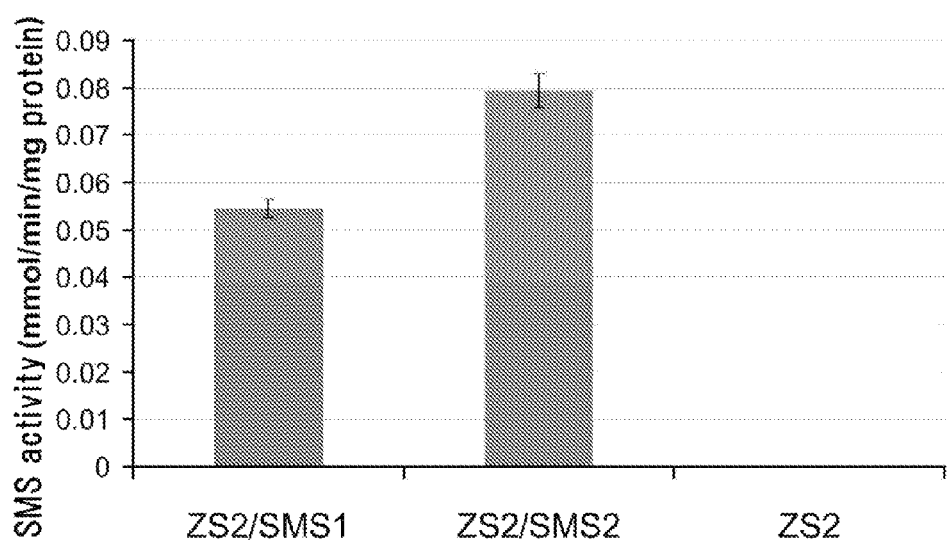
FIG. 7 shows the result of investigation in Example 3 on SMS activity of ZS2 cell, ZS2/SMS1 cell and ZS2/SMS2 cell. ZS2/SMS1 cell (left) and ZS2/SMS2 cell (middle) had an SMS activity, while ZS2 cell (right) did not have an SMS activity. Vertical axis of the graph shows SMS activity (Unit: nmol/minute/mg protein).

The cells made in Example 2 were spread in 6-well plates each ($2\times10^5$ cell/well), was cultured overnight in DMEM including 10% FBS, then the mediums were replaced with DMEM without serum, and BODIPY-C5-ceramide (molecular probe) adjusted to a final concentration of 1 micromolar was added and they were allowed to react at 37 degrees Celsius for 30 minutes. After the cells were detached by pipetting, they were solubilized with 100 microliter of a solubilizing buffer (20 mM Tris-HCl, pH7.5, 0.2% Triton X-100, 1× complete (Roche), 1 mM PMSF) and the protein amounts were measured with BCA protein assay (Pierce). Lipids were extracted from the solubilized solution with Bligh & Dyer method, and using HPTLC (Merck), BODIPY-ceramide and the produced BODIPY-C5-sphingomyelin were quantified with Fla7000 (Fuji film) and the SMS activity was calculated. The SMS activity was corrected for protein amount. As shown in FIG. 7, ZS2/SMS1 cell and ZS2/SMS2 cell had an SMS activity, while ZS2 cell did not have an SMS activity.

2) TG Synthesis

Figure 8:
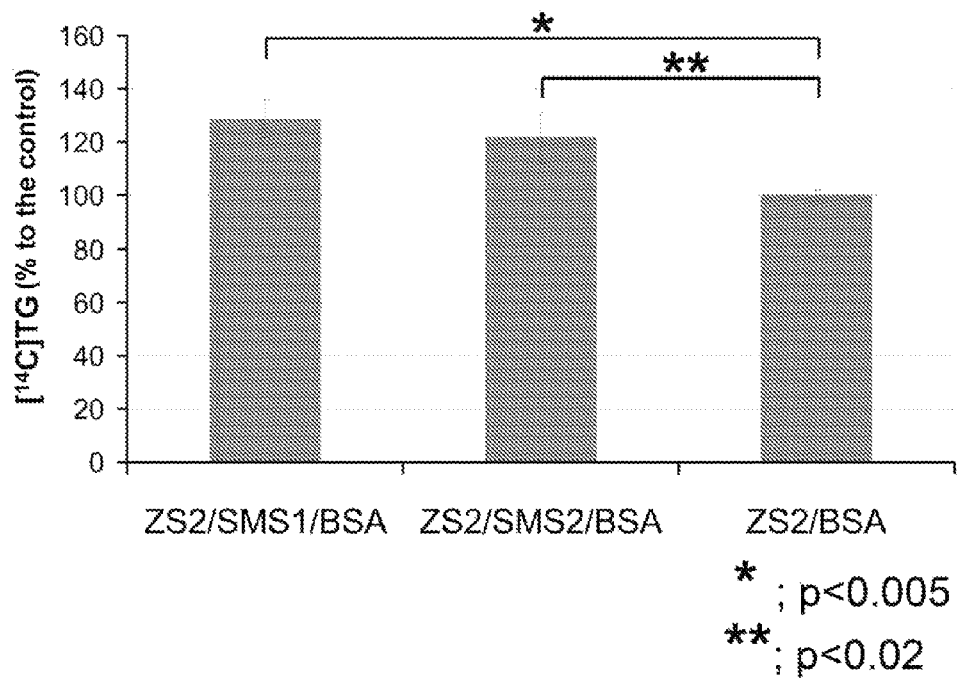
FIG. 8 shows the result of investigation in Example 3 on TG synthesis by ZS2 cell, ZS2/SMS1 cell and ZS2/SMS2 cell. There was a significant difference between the TG amount in ZS2/SMS 1 cell (left) and ZS2/SMS2 cell (middle), and the TG mount of ZS2 cell (right) ($p<0.005$ and $p<0.02$, respectively). Vertical axis of the graph shows percentage (%) of $[^{14}C]TG$ to control (ZS2 cell).

The cells made in Example 2 were spread into 6-well plates ($2\times10^5$ cell/plate), cultured overnight in DMEM with 10% FBS, then the mediums was DMEM without serum, and [$^{14}$C] oleic acid (American Radiolabeled Chemicals) at a final concentration of 1 microcurie was added and allowed to react at 37 degrees Celsius for 30 minutes. After the cells were detached by pipetting, they were solubilized with 100 microliter of a solubilizing buffer (20 mM Tris-HCl, pH 7.5, 0.2% Triton X-100, 1× complete (Roche), 1 mM PMSF) and the protein amounts were measured with BCA protein assay (Pierce). Lipids were extracted from the solubized solution with Bligh & Dyer method, and using HPTLC (Merck), [$^{14}$C] oleic acid and the produced [$^{14}$C] oleic acid-triglyceride were quantified with Fla7000 (Fuji film) and the TG amounts were calculated. As shown in FIG. 8, there was a significant difference between the TG amount in the ZS2/SMS 1 cell and the ZS2/SMS2 cell and the TG mount of the ZS2 cell ($p<0.005$ and $p<0.02$, respectively).

Example 4

Screening siRNAs Toward SMS2

In the Example, screening siRNAs toward SMS2 was carried out. Specific procedures were as follows.

siRNAs shown below whose sequences were orinally designed were synthesized and transformed into Hepa1c1c7 cells or HeLa cells. By measuring SMS2 mRNA amounts 48 hours after, the rates of suppressing SMS2 expression by siRNAs (knockdown rates) were compared. Both cells were cultured in DMEM including 10% FCS (fetal calf serum) under conditions of 5% $CO_2$ and 37 degrees Celsius. At the day before transfection, the cells were spread into 12-well plates and cultured for 24 hours. With RNAiMAX (Invitrogen), each siRNA was transfected at a final concentration of 100 nM, and 48 hours after, the mRNA amounts of SMS2 were measured. After treating with DNase I using RNeasy Mini Kit (QIAGEN) according to the attached manual, total RNA was recovered and cDNA was synthesized by using SuperScriptIII First Strand Synthesis System (Invitrogen) according to the attached manual. By carrying out a realtime quantitative PCR on the synthesized cDNA as templates, the mRNA amounts of SMS2 were quantified. In the realtime quantitative PCR, SYBR Green PCR Master Mix (ABI) was used as a reaction reagent and the measurement was carried out with Applied Biosystems 7500 Realtime PCR Symtem (ABI). cDNA was normalized among samples with the expression amount of G3PDH.

As realtime quantitative PCR primer sequences used for measuring the expression amounts of human and mouse SMS2,

```
                                     (SEQ ID NO: 33)
Fw primer:     TCAATGGAGACTCTCAGGC;

(SEQ ID NO: 34)
Rv primer:     CCGCTGAAGAGGAAGTCTC
``` were used, as realtime quantitative PCR primer sequences used for measuring the expression amounts of human G3PDH.

```
                                            (SEQ ID NO: 35)
    Fw primer:      CCTTCCGTGTCCCCACTG;

(SEQ ID NO: 36)
    Rv primer:      ACCCTGTTGCTGTAGCCAA
``` were used, as realtime quantitative PCR primer sequences used for measuring the expression amounts of mouse G3PDH,

```
                                            (SEQ ID NO: 37)
    Fw primer:      CAACTCCCACTCTTCCACCTTC;

(SEQ ID NO: 38)
    Rv primer:      CTTACTCCTTGGAGGCCATGTAG
``` were used.

The sequences of mouse specific siRNAs used are shown below.

```
    SMS2-i1:
                                            (SEQ ID NO: 39)
    5'-ggucacuuggaaagucaaa-3' (a sense strand)
```

Its antisense strand that is a complementary sequence thereto (SEQ ID NO: 40)

```
    SMS2-i2:
                                            (SEQ ID NO: 41)
    5'-ccggacuacauccagauuu-3' (a sense strand)
```

Its antisense strand that is a complementary sequence thereto (SEQ ID NO: 42)

```
    SMS2-i3:
                                            (SEQ ID NO: 21)
    5'-ggaugguauugguugggu-3' (a sense strand)
```

Its antisense strand that is a complementary sequence thereto (SEQ ID NO: 22)

```
    SMS2-i4:
                                            (SEQ ID NO: 43)
    5'-gcagauuguuguugaucau-3' (a sense strand)
```

Its antisense strand that is a complementary sequence thereto (SEQ ID NO: 44).

The sequences of siRNAs used that are homologous between a human and a mouse are shown below.

```
    SMS2-i5:
                                            (SEQ ID NO: 45)
    5'-cauagagacagcaaaacuu-3' (a sense strand
```

Its antisense strand that is a complementary sequence thereto (SEQ ID NO: 46)

```
                                            (SEQ ID NO: 1)
    SMS2-i6: 5'-gcauuuucuguaucagaaa-3' (a sense
    strand
```

Its antisense strand that is a complementary sequence thereto (SEQ ID NO: 2)

```
                                            (SEQ ID NO: 3)
    SMS2-i7: 5'-gucacuucguggguauca-3' (a sense
    strand)
```

Its antisense strand that is a complementary sequence thereto (SEQ ID NO: 4)

```
                                            (SEQ ID NO: 5)
    SMS2-i8: 5'-cuguuuggugguaccauu-3' (a sense
    strand)
```

Its antisense strand that is a complementary sequence thereto (SEQ ID NO: 6).

The sequences of human specific siRNAs used are shown.

```
                                            (SEQ ID NO: 7)
    SMS2-i104: 5'-gggcauugccuucauauau-3' (a sense
    strand)
```

Its antisense strand that is a complementary sequence thereto (SEQ ID NO: 8)

```
                                            (SEQ ID NO: 9)
    SMS2-i105: 5'-ggcuguuucugagauacaa-3' (a sense
    strand)
```

Its antisense strand that is a complementary sequence thereto (SEQ ID NO: 10)

```
                                            (SEQ ID NO: 11)
    SMS2-i106: 5'-gguggugauuguccauaa-3' (a sense
    strand)
```

Its antisense strand that is a complementary sequence thereto (SEQ ID NO: 12)

```
                                            (SEQ ID NO: 13)
    SMS2-i107: 5'-ggauuguccauaacuggau-3' (a sense
    strand)
```

Its antisense strand that is a complementary sequence thereto (SEQ ID NO: 14)

```
                                            (SEQ ID NO: 15)
    SMS2-i108: 5'-ccauaacuggaucacauau-3' (a sense
    strand)
```

Its antisense strand that is a complementary sequence thereto (SEQ ID NO: 16)

```
                                            (SEQ ID NO: 17)
    SMS2-i109: 5'-gcacacgaacacuacacua-3' (a sense
    strand)
```

Its antisense strand that is a complementary sequence thereto (SEQ ID NO: 18)

Figure 9:
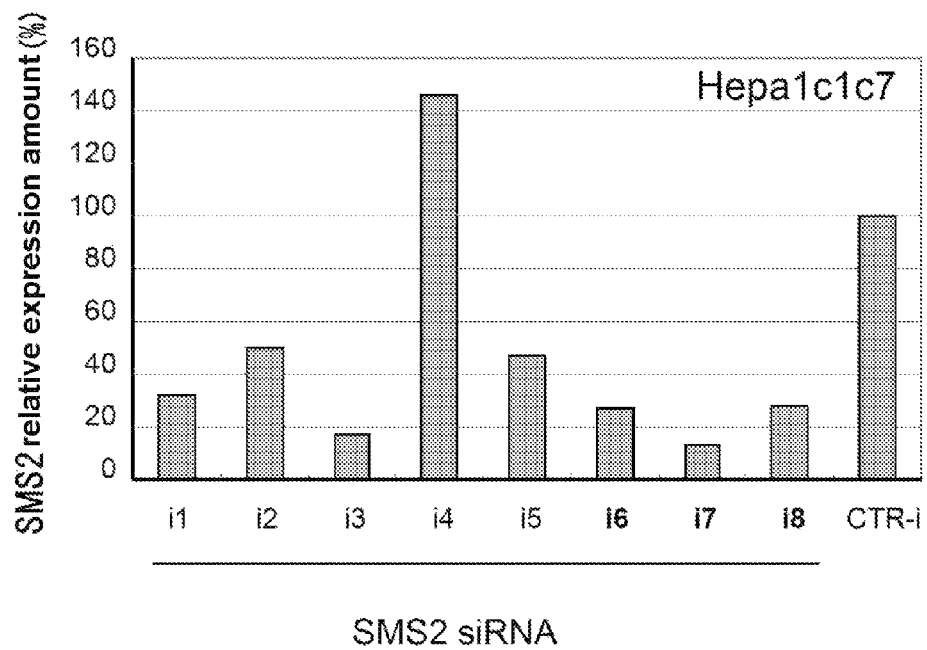
FIG. 9 shows a result of investigation wherein various siRNAs were administered to Hepa1c1c7 cell and screened if they functioned as siRNA toward mouse SMS2. SMS2-i1, SMS2-i3, SMS2-i6, SMS2-i7 and SMS2-i8 retained 65% or more of a knocking-down activity toward mouse SMS2 expressed in Hepa1c1c7 cell that is a mouse cell.

As a result, as shown in FIG. 9, all of the siRNA sequences that are homologous between a human and a mouse (SMS2-

Figure 10:
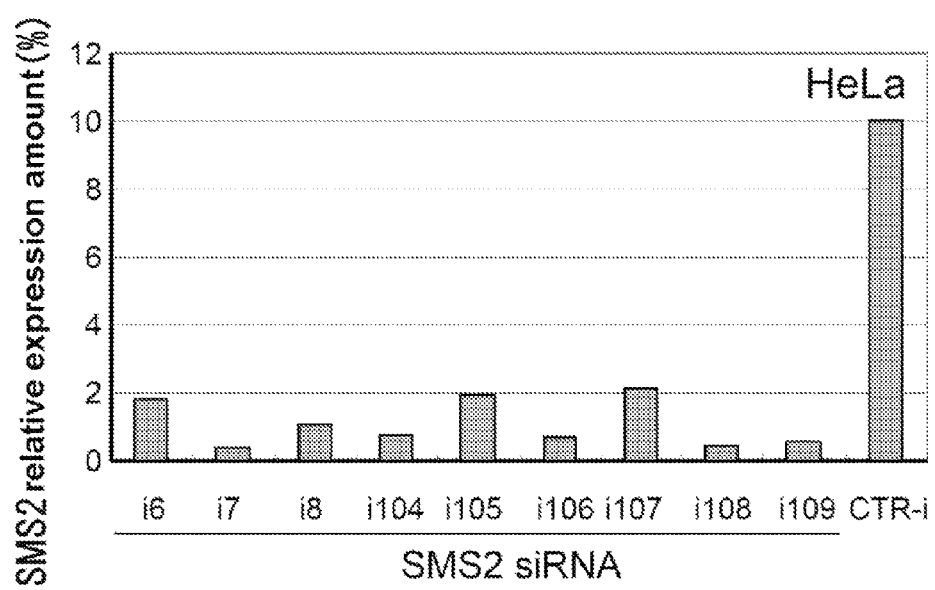
FIG. 10 shows a result of investigation wherein various siRNAs were administered to HeLa cell and screened if they functioned as siRNA toward human SMS2. SMS2-16, SMS2-17, SMS2-18, SMS2-i104, SMS2-i105, SMS2-i106, SMS2-i107, SMS2-i108 and SMS2-i109 retained at least 75% or more of a knocking-down activity toward human SMS2 expressed in HeLa cell that is a human cell.

16, SMS2-17, and SMS2-18) retained 70% or more of a knocking-down activity toward mouse SMS2 in Hepa1c1c7 cell that is a mouse cell (represented a control CTR-i as 100%). In addition, as shown in FIG. 10, three these siRNA sequences also retained 80% or more of a knocking-down activity in human HeLa cell (represented CTR-i as 100%). Furthermore, as shown in FIG. 10, all of SMS2-i104 to SMS2-i109 that are siRNAs specific to human SMS2 retained 75% or more of a knocking-down activity in HeLa cell.

Example 5

Knockdown of SMS2 in SMSs-Reconstructed Cells

Figure 11:
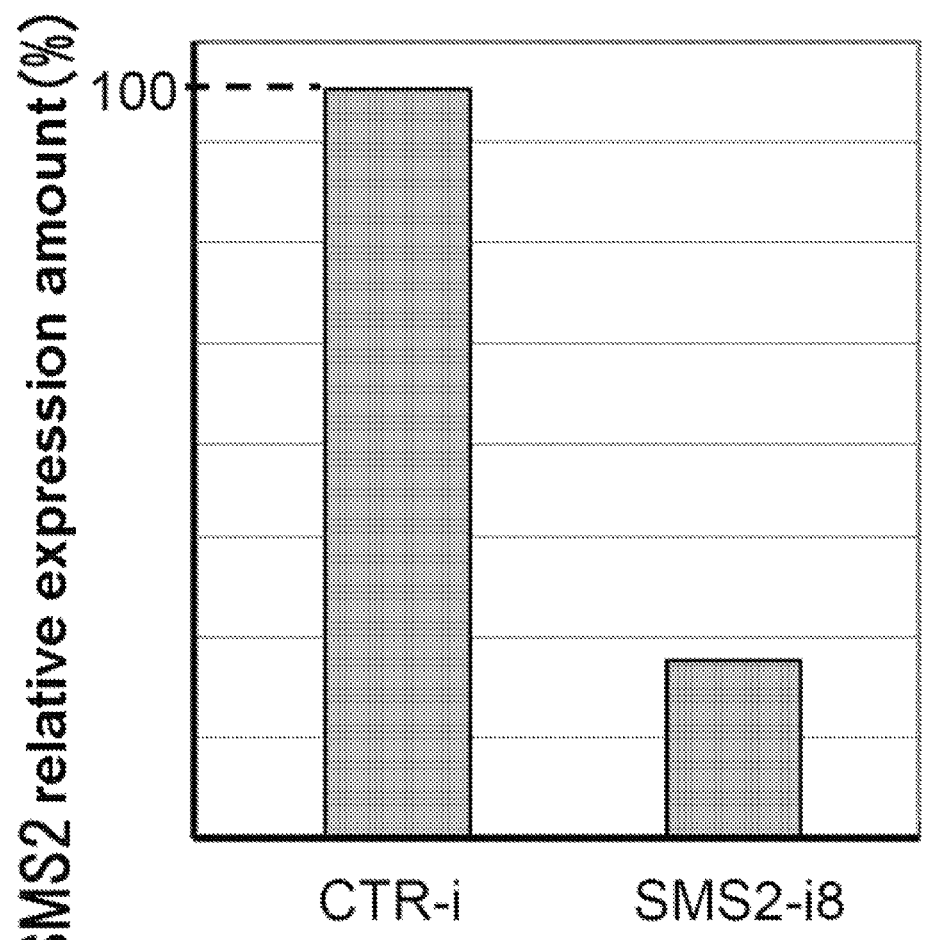
FIG. 11 shows a result that it was investigated whether SMS2-i8 has an effect of suppressing the SMS2 expression on ZS2/SMS2 cell made in Example 2. When SMS2-i8 was administered, SMS2 expression was suppressed by 80% or more compared to when control siRNA was administered.

As shown in FIG. 11, using SMS2-i8 and mouse ZS2/SMS2 cell, same experiment as in Example 4 was carried out. The final concentration of siRNA was 100 nM, and quantitative PCR was carried out 48 hours after transformation. As a result, suppression in gene expression of SMS2 by about 80% was confirmed. As an endogenous control, G3PDH was used.

Figure 12:
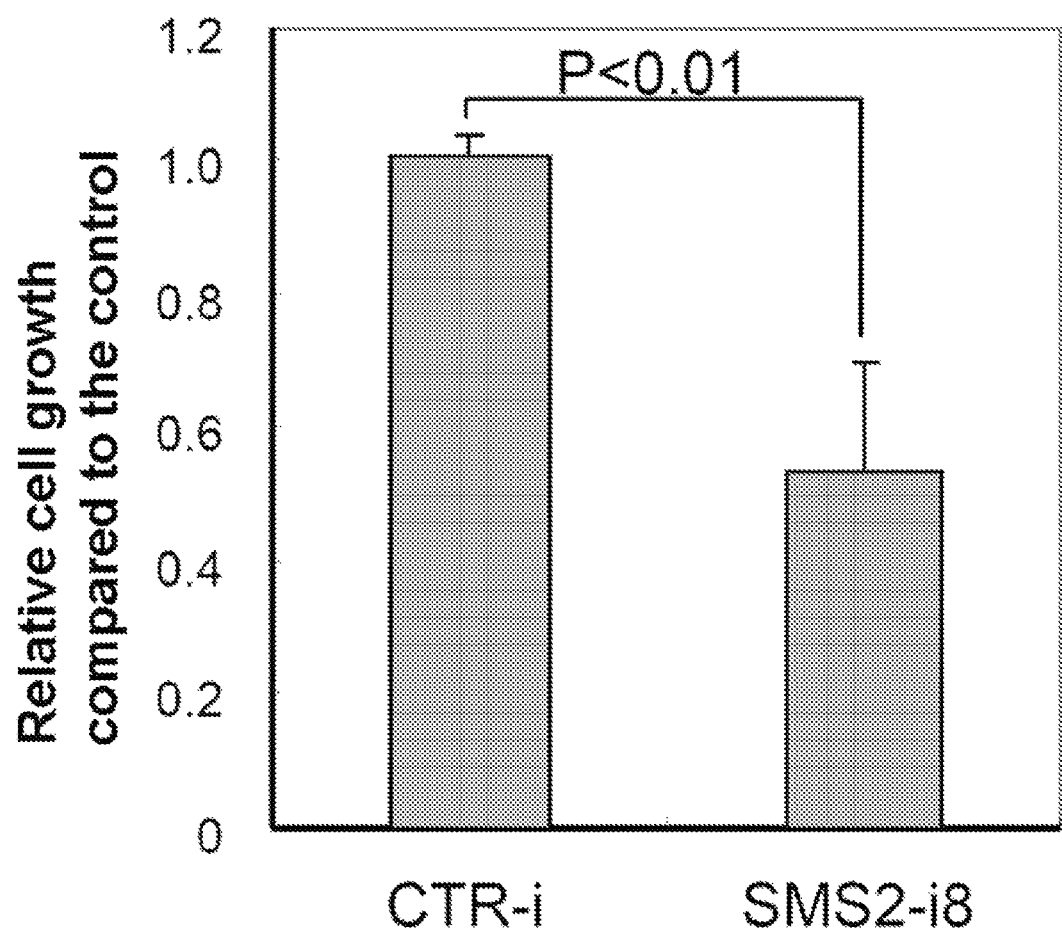
FIG. 12 shows a result that it was investigated whether administration of SMS2-i8 to ZS2/SMS2 cell made in Example 2 changed the sensitivity of the cell to Me-beta-CD. When SMS2-i8 was administered, the survival rate of the cell was significantly lower compared to when control siRNA was administered.

Next, it was investigated to confirm whether SMS2-i8 suppressed SMS2 gene expression in the mouse ZS2 cell and decreased SM on its cell membrane. As shown in FIG. 12, by using the ZS2/SMS2 cell, it was knocked down with SMS2-i8 toward human SMS2, and a test of evaluating Me-beta-CD sensitivity was carried out.

Into 6-well dishes, $2\times10^5$ of ZS2/SMS2 cells suspended in 2 ml of 10% FCS/DMEM medium were spread and various siRNAs were mixed with a commercially aviable transformation reagent RNAiMAX (Invitrogen) and added at a final concentration of 100 nM. Following the manufacturer's protocol, transformation was carried out. After 24 hours, the mediums was replaced with 0.3% FCS OPTIPRO SFM (GIBCO), and cultured for additional 24 hours, then Me-beta-CD was added at a final concentration of 5 mM and they were further cultured at 5% $CO_2$ and 37 degrees Celsius for 16 hours. Seisaibo Su Sokutei Shiyaku [Reagent for measuring living cell counts]including WST8 was added at 10 microliter/well, and further cultured for 6 hours at 5% $CO_2$ and 37 degrees Celsius. Living cell counts were measured following the protocol.

When the ZS2/SMS2 cell was knocked out with siRNA (SMS2-18) toward a human SMS2, the cell became Me-beta-CD-sensitive, and the cell growth was significantly decrease at final Me-beta-CD concentration of 5 mM (test for a significant difference test P<0.01).

Therefore, it is recognized that due to that SMS2 of the ZS2/SMS2 cell is knocked down with the siRNA, SM on the cell membrane is decreased and the ZS2/SMS2 cell became Me-beta-CD-sensitive. Therefore, it is recognized that the siRNA has an activity of decreasing SM on a cell membrane.

The sequences of the siRNA used as a control (CTR-i) are shown.

(SEQ ID NO: 19)
CTR-i: 5'-uucuccgaacgugucacgu-3' (a sense strand)

Its antisense strand (SEQ ID NO: 20).

Example 6

Knockdown of SMS2 in a Mouse Liver

In the Example, by using two kinds of siRNAs toward a mouse SMS2 (SMS2-i3, SMS2-i11), SMS2 in Hepa1c1c7 cell (ATCC) that is a mouse liver parenchymal cell strain was knocked down and the effect was confirmed.

Into 12-well dishes, $1\times10^4$ of the cells were spread. After 24 hours, transformation was carried out using a commercially aviable transformation reagent RNAiMAX (Invitrogen) following the manufacturer's protocol. The final concentration of siRNA was 100 nM. After 48 hours, the cells were solubilized with 0.5 ml of Trizol (Invitrogen), and RNA was extracted following the protocol. Reverse transcription into cDNA was carried out following usual methods by using a commercially available kit Superscript III (Invitrogen). A quantitative PCR was carried out by using the above primers and a commercially available kit (ABI).

Figure 13:
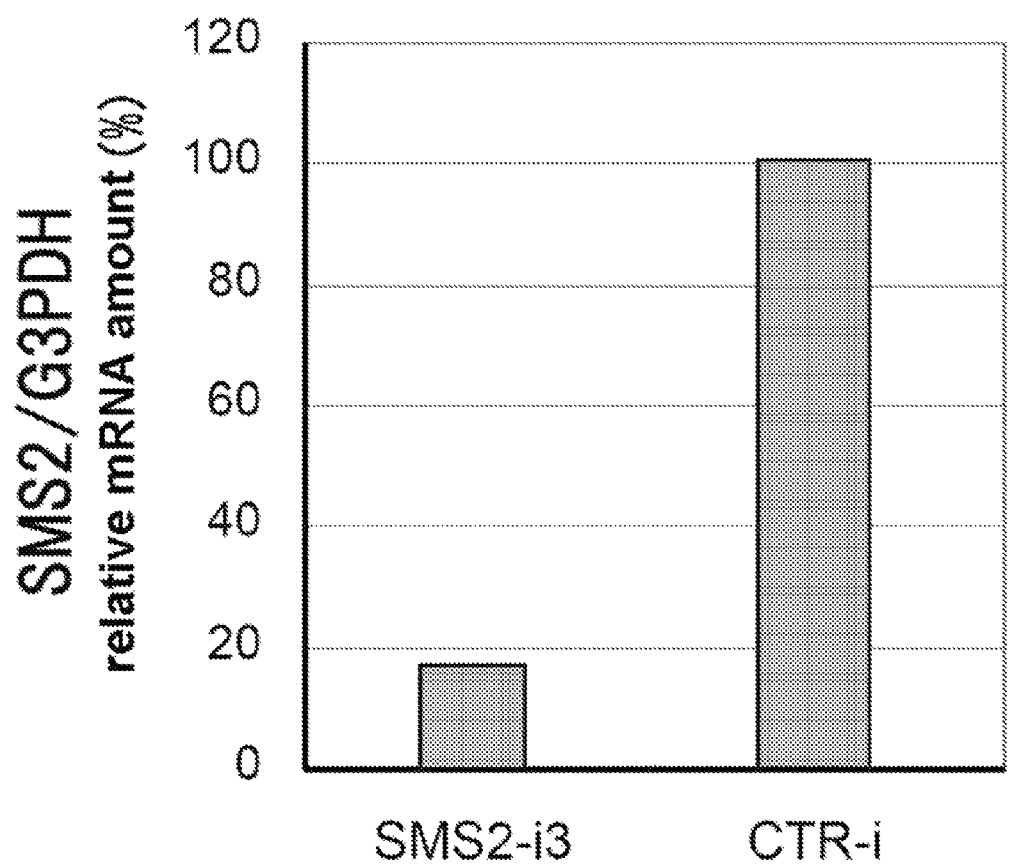
FIG. 13 shows a result that it was investigated whether introduction of SMS2-i3 into Hepa1c1c7 cell suppressed the SMS2 expression in the cell. When SMS2-i3 was introduced, SMS2 expression amount in the cell was suppressed by 80% or more compared to when control siRNA was administered.
Figure 14:
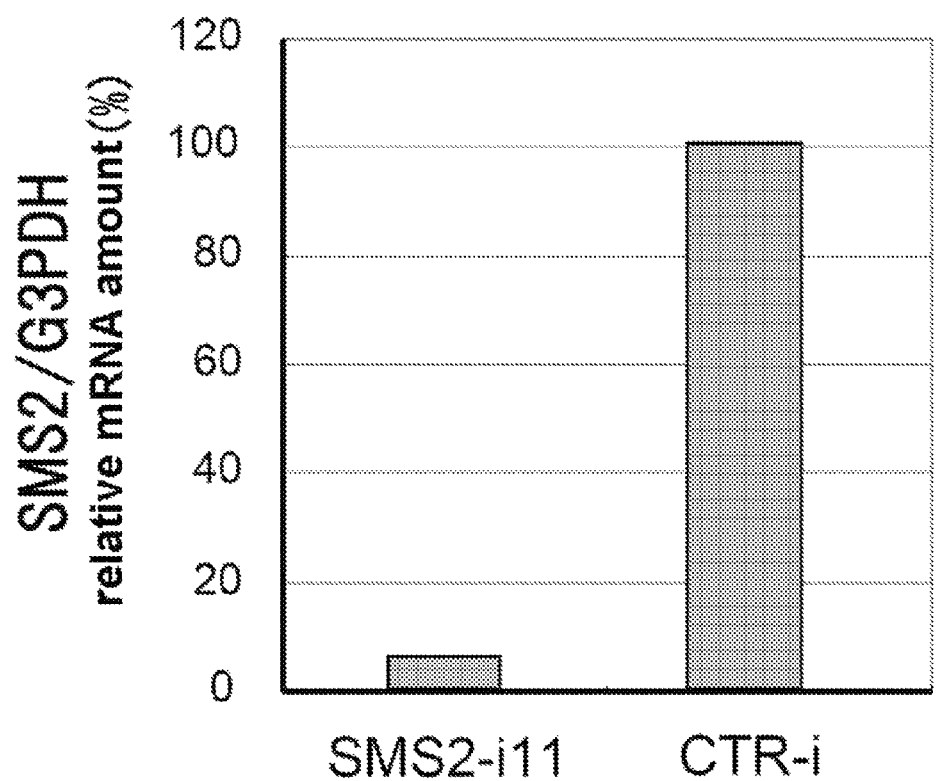
FIG. 14 shows a result that it was investigated whether introduction of SMS2-i11 into Hepa1c1c7 cell suppressed the SMS2 expression in the cell. When SMS2-i11 was administered, SMS2 expression amount in the cell was suppressed by 80% or more compared to when control siRNA was introduced.
Figure 15:
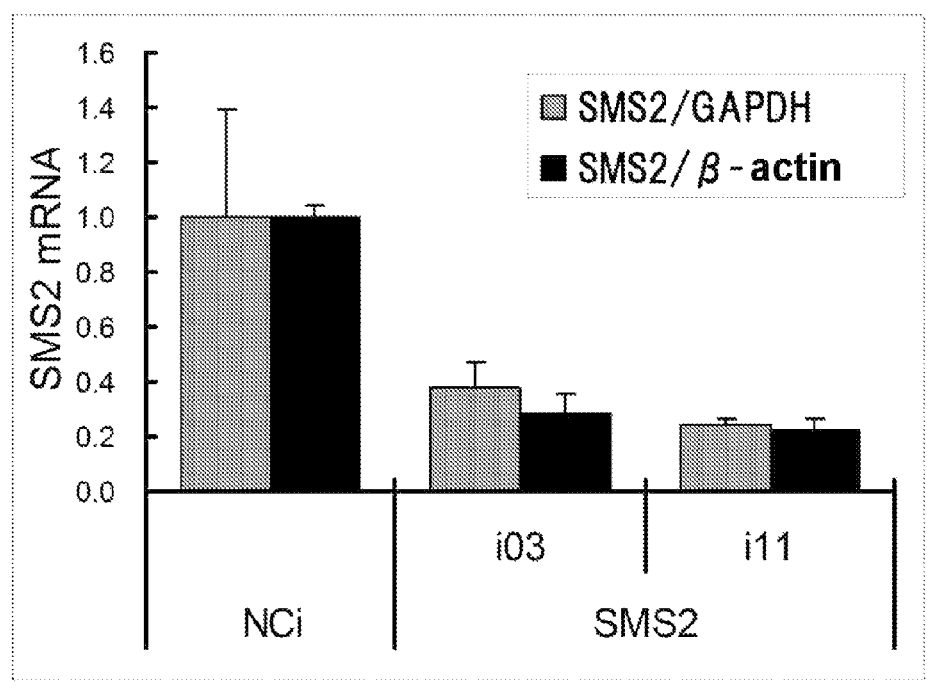
FIG. 15 shows a result that it was investigated whether administration of SMS2-i3 or SMS2-i11 into leptin deficient obesity mice via tail vein injection suppressed the SMS2 expression in the liver of the mice. When SMS2-i3 was administered, SMS2 expression amount in the liver of the mouse was suppressed by 60% or more compared to when control siRNA was introduced. When SMS2-i11 was administered, SMS2 expression amount in the liver of the mouse was suppressed by 70% or more compared to when control siRNA was introduced.

In the cases using any of the siRNA sequences, 80% or more knockdown was confirmed (FIG. 13 and FIG. 14). For normalization of cDNA, G3PDH was used.

The sequences of mouse SMS2 specific siRNAs used are shown.

(SEQ ID NO: 21)
SMS2-i3: 5'-ggaugguauugguuggguu-3' (a sense strand

Its antisense strand that is complementary sequence thereto (SEQ ID NO: 22)

(SEQ ID NO: 23)
SMS2-i11: 5'-ggcucuuucugcguuacaa-3' (a sense strand)

Its antisense strand that is complementary sequence thereto (SEQ ID NO: 24).

In order to administer these siRNAs (i3 and i11) which were confirmed for their knocking down activity at cell level to mice, so-called siRNA loaded liposomes were made. The siRNA loaded liposomes were made with reference to the following paper (Nature Biotechnology, Vol. 28, No. 2, p 172-176, 2010). They were made by mixing lipids and siRNAs with ethanol injection method. Compared to the paper, lipid composition was slightly modified to be C18PEG:Dlin-KC2-DMA:DPPC:Chol.=2:56.6:3.5:34.3(%). When the particle diameters of the liposomes made were measured, they were about 100 nm in the cases that any of the siRNAs were used, and their zeta potential were almost neutral.

Next, leptin deficient obesity mice were prepared by feeding a normal diet to C57BL/6JHamSlc-ob/ob (Japan SLC, hereinafter, ob/ob mice). The siRNA loaded liposomes made as described above were administered to the ob/ob mice (5 weeks old, female) in 1.25 mg/kg as siRNA amount by injecting into their tail vein (n=3). On the day 3 after administration, the livers were recovered and knockdown rate was measured by the same method as the method of quantifying RNA from cell shown in FIG. 9. SMS2-i3 or SMS2-i11 (respectively, n=3) as groups wherein SMS2 expression were suppressed and CTR-i (n=3) as a negative group were administered and evaluated. As a result of analyzing the expression of SMS2 in the liver, the expression level of the mRNA was suppressed by 80% in the group which SMS2-i11 was administered and by about 70% in the group which SMS2-i3 was administered. From above, it could be confirmed that the suppression of the expression of SMS2 in the liver was succeeded.

Example 7

Figure 17:
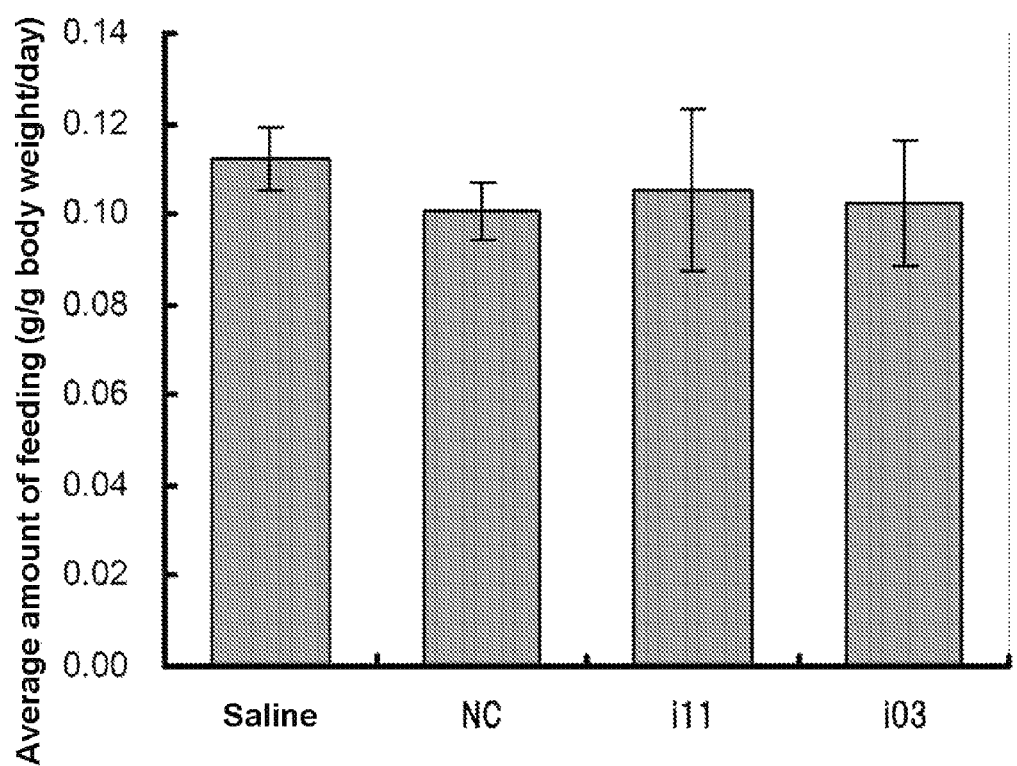
FIG. 17 shows a result wherein SMS2-i3 or SMS2-i11 were administered into mice via tail vein injection and average amount of feeding was investigated for 10 days after administration. In the cases which SMS2-i3 or SMS2-i11 were administered and in the control group mice, there was no significant difference in average amount of feeding.

Decrease in Liver Triglyceride by Suppression of SMS2 in Mouse Liver siRNA loaded liposomes were administered into 7 weeks old ob/ob mice (male) in 1.25 mg/kg as siRNA amount by injecting into their tail vein (n=3). After administration, the body weight and amount of feeding were measured for 10 days. At 10 days after administration, the liver tissues of the ob/ob mice were recovered after 4 hours fasting. The results of measuring the change of body weight at the time when 10 days has elapsed after administration and average amount of feeding for the 10 days are shown in FIG. 16 and FIG. 17. There was no significant difference in body weight gain and average amount of feeding compared to the control group.

Figure 18:
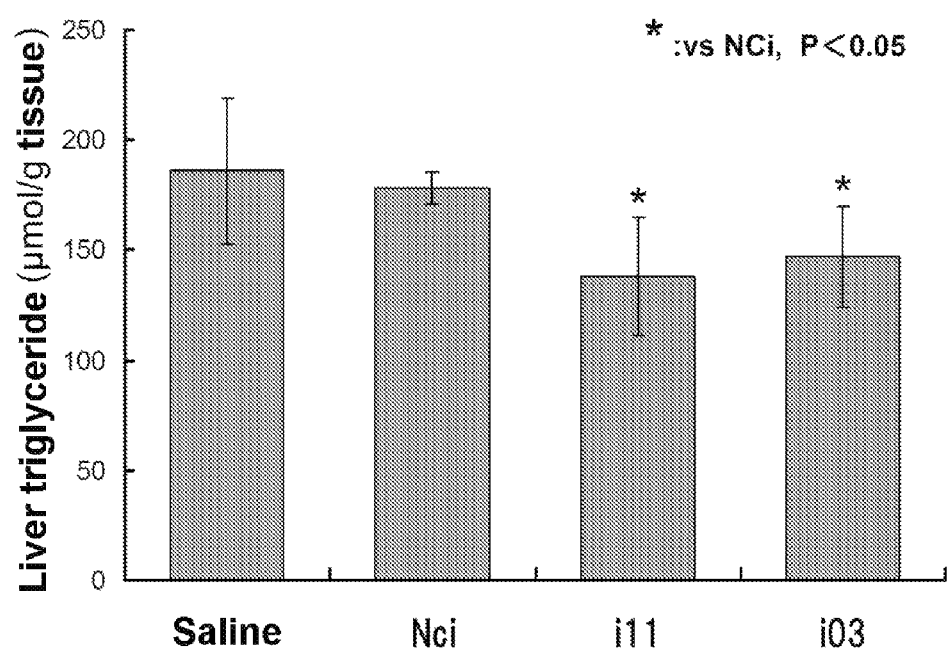
FIG. 18 shows a result wherein SMS2-i3 or SMS2-i11 were administered into mice via tail vein injection and triglyceride amount in the liver of mice after fasted for 4 hours on 10 days after administration was investigated. When SMS2-i3 or SMS2-i11 were administered, triglyceride amount in the liver was significantly decreased compared to in the control group mice.

Extraction of lipid components from the liver was in accordance with Folch method. 0.5 g of livers were homogenized and placed into microtubes, added 0.1M KCl and filled up to 1.4 mL, stirred well and then transferred into 15 mL Falcon tubes. Then, 6 mL of a mixture solution of $CHCl_3$ and MeOH (2:1) was added and stirred at room temperature for 2 hours. 2 mL of distilled water was added, stirred well and left for 5 minutes. They were centrifuged at 3000 rpm for 10 minutes, and the lower layer (organic layer) was recovered to 720 microliter. After completely removing organic solvents by evaporation, yellow transparent lipid component was obtained. The extracted triglyceride was measured with Triglyceride E-Test Wako (GPO-DAOS method: Wako Pure Chemical Industries, Ltd.) following the attached manual. The results of measuring triglyceride amount in the liver are shown in FIG. 18. From the results of measurement, decrease in liver triglyceride by suppressing the expression of SMS2 (SMS2-i3 or SMS2-i11 administration) compared to the control group (CTR-i administration) was observed ($p<0.05$) (n=3).

From the results, since decrease in liver triglyceride by two different kinds of siRNA sequences toward a mouse SMS2 could be confirmed, it could be confirmed that the effect was not so-called off-target effect but raised by suppression of SMS2 expression. From the above results, suppression of visceral fat accumulation and suppression of fatty liver were confirmed.

In addition, since the ob/ob model is also a model for diabetes, it is understood from the experimental results of Example 8 or the like that the siRNAs of the present invention can be also expected for effect on diabetes.

Example 8

Decrease in Triglyceride by Suppression of SMS2 in HepG2 Cell

Figure 19:
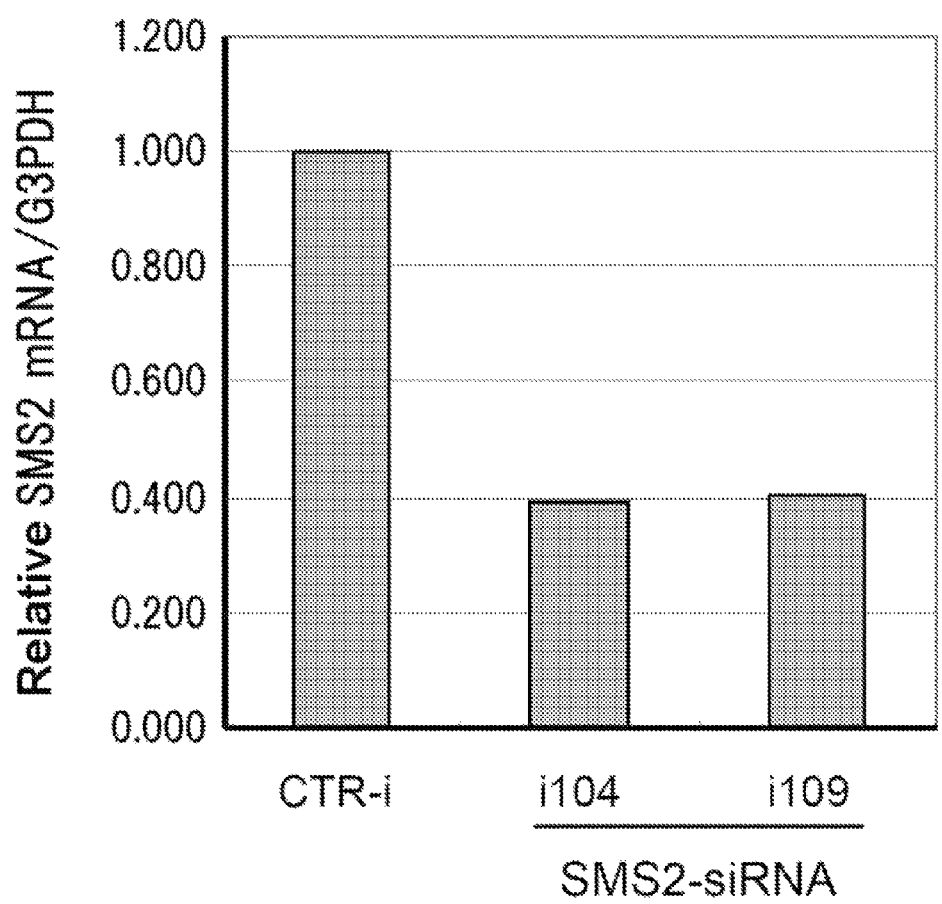
FIG. 19 shows a result wherein HepG2 cell, a human liver parenchymal cell strain, was transformed with control siRNA sequence (CTR-i), SMS2-i104 or SMS2-i109, and SMS2 expression amount after 48 hours was measured in the same method as in FIG. 9. In any of the cases which SMS2-i104 or SMS2-i109 were used, SMS2 expression amount were decreased by about 60% compared to when the control sequence was used.

HepG2 cell that is a human liver parenchymal cell was transformed with a control siRNA sequence CTR-i, SMS2-i104 or SMS2-i109. Knockdown rates of SMS2 after 48 hours were measured by the same method as for FIG. 9. As a result, in the cases using any of the siRNA sequences, about 60% knockdown could be confirmed (FIG. 19).

Figure 20:
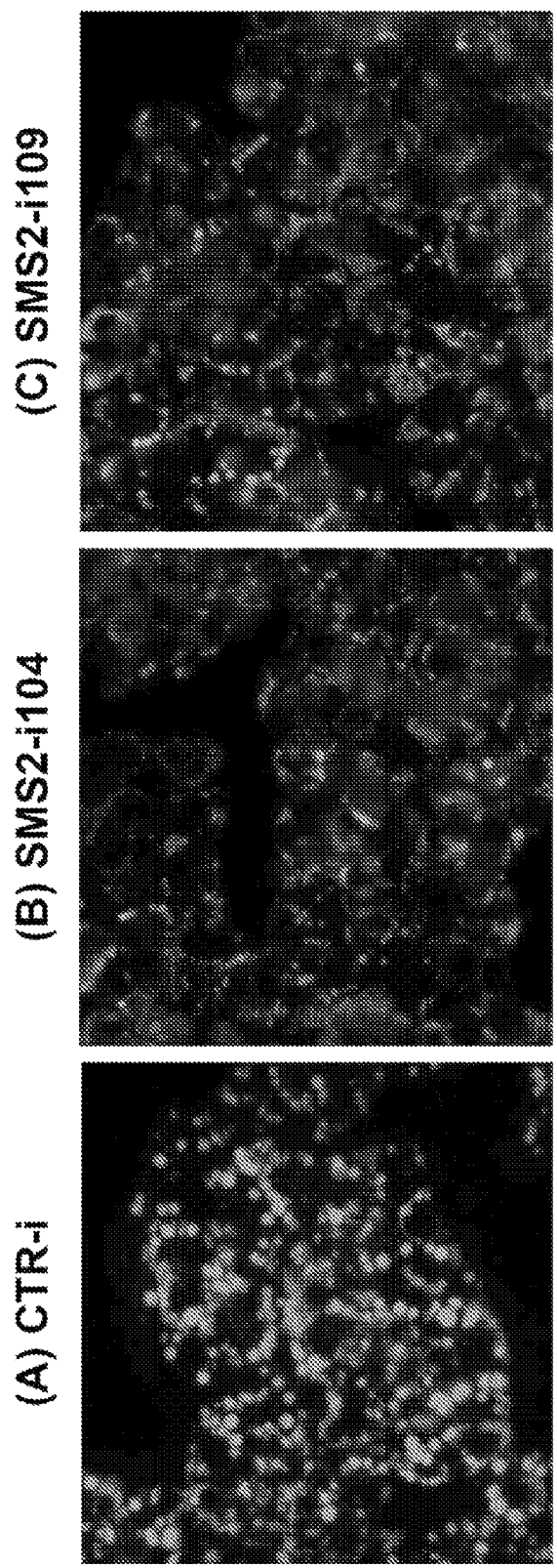
FIG. 20-B shows a result wherein HepG2 cell that is a human liver parenchymal cell strain, was transformed with SMS2-i104 and stained with a fluorescent reagent AdipoRed (NileRed) after 72 hours which can specifically stain triglyceride, and the cell was observed with a fluorescent microscope after 5 minutes. It could be confirmed that when the cell was transformed with SMS2-i104, particle size of lipid droplet in the cell was smaller compared to when CTR-i was used.
Figure 21:
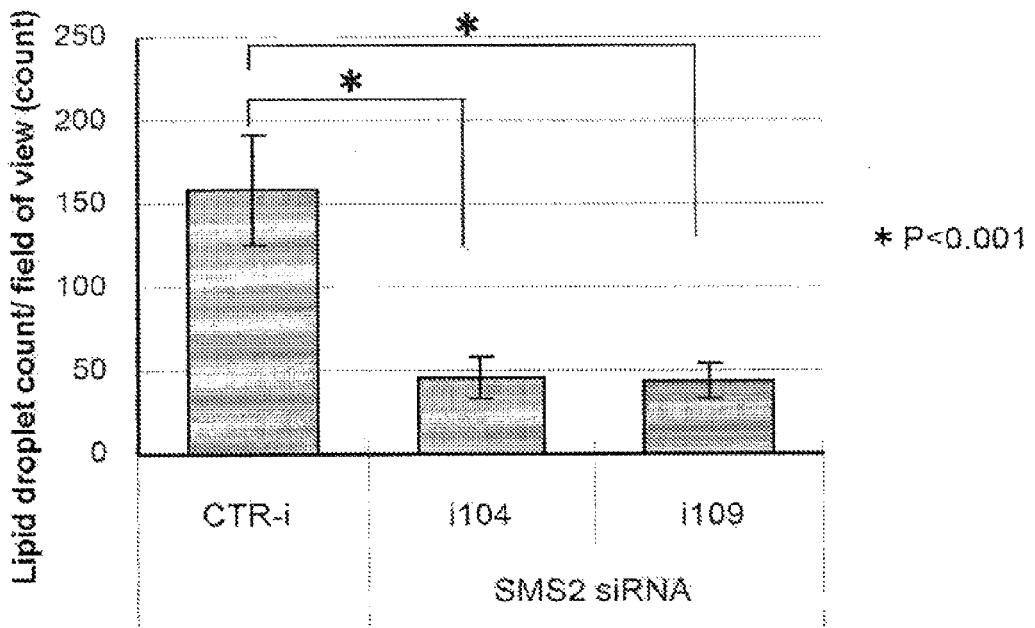
FIG. 21 shows a result wherein cells that were fluorescently stained in FIGS. 20A-C were taken photograph randomly in 5 field of view, and the number of lipid droplets with a diameter of 1.25 micrometer or more was counted. It could be confirmed that when the cell was transformed with SMS2-i104 or SMS2-i109, the number of lipid droplets with a diameter of 1.25 micrometer or more was significantly decreased to about 30% compared to when transformed with the control siRNA sequence. From that, it was suggested that by inhibition of SMS2 in liver cells, anti-obesity effect was raised.
Figure 22:
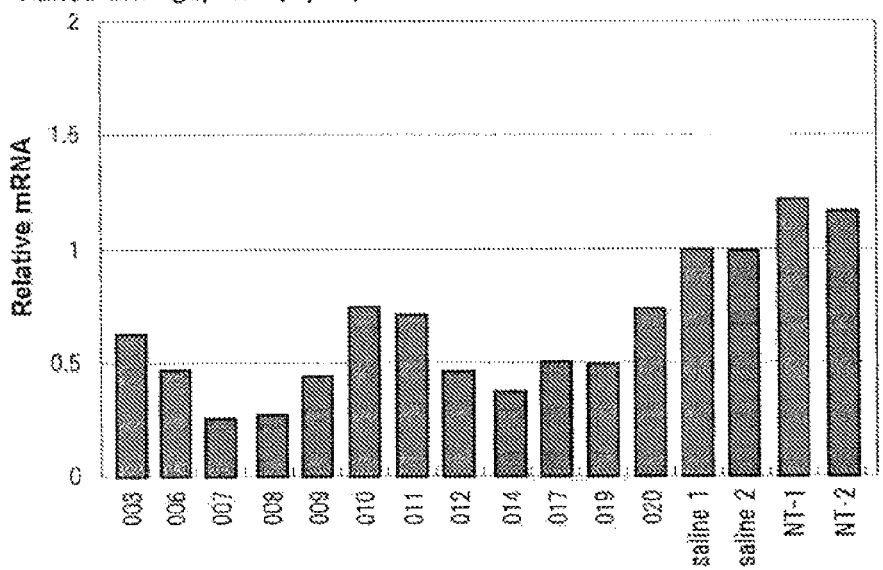
FIG. 22 shows the result in Example 10 wherein an LNA type Gapmer antisense oligonucleotide was used as an example of an LNA-containing nucleic acid to carry out a knockdown experiment in human HEK 293 cell. The LNA type Gapmer antisense oligonucleotide used was added in a naked form at a final concentration of 5 micromolar to the cell culture solution. The result of a quantitative PCR carried out 72 hours after transformation is shown. The numbers at the horizontal axis show those which correspond to "XXX" in the antisense oligos SMS2-13-XXX used (which correspond to SEQ ID NOs: 81-92, from left to right, respectively). Saline 1 and Saline 2 are respectively controls to which saline was added. NT-1 and NT-2 respecvitly shows untreated controls to which nothing was added.

After confirming the knockdown, HepG2 cells were transformed with 3 kinds of siRNAs: CTR-i, SMS2-i104 or SMS2-i109, and after 24 hours, FCS of the medium was changed to 0.5%. After additional 24 hours, oleic acid dissolved in ethanol was mixed with BSA, sonicated with a bath-type sonicator, and the dispersed oleic acid-BSA mixture was added to the medium. The final concentration of oleic acid added was 0.4 mM and that of BSA added was 1%. After additional 24 hours, the medium was removed, the cells was washed with PBS twice, then 10% formalin-PBS solution was added and the cells were fixed for 10 minutes. Then, the formalin solution was removed from the cells, the cells were washed with PBS three times to completely remove PBS. AdipoRed (NileRed) (Lonza) solution that is a fluorescent reagent capable of specifically staining triglyceride was added to a PBS solution at a final concentration of 4% and the PBS solution was added to the cells. After 5 minutes, the cells were observed with a fluorescent microscopy (FIGS. 20A-C). Since it was considered that the particle diameter of lipid droplets in the cells became smaller in the case SMS2-i104 or SMS2-i109 were transformed than in the case CTR-i was transformed, they were taken photograph randomly in 5 fields of view and the number of lipid droplets with a diameter of 1.25 micrometer or more was counted. As a result, when the cell was transformed with SMS2-i104 or SMS2-i109, the number of lipid droplets with a diameter of 1.25 micrometer or more was decreased to about 30% compared to when transformed with CTR-i (FIG. 21). Such phenomenon was known to result from, for example, inhibition of caveolin or perilipin, DGAT2 or the like. In addition, all of the mice wherein these genes are knocked out have an anti-obesity effect. Therefore, combining with the results of Example 8 and Example 7, it was suggested that by inhibition of SMS2 in liver cells, anti-obesity effect was raised.

Next, the TG amount in these lipid droplets was calculated as luminance by quantifying the amount of fluorescence in the images. BZII Analysis Software of KEYENCE was used as a measuring software. As a result, when the cell was transformed with SMS2-i104 or SMS2-i109, the amount of fluorescence was significantly decreased compared to when transformed with CTR-i. It was thus fond that uptake or conversion into TG of oleic acid or both were inhibited in the human liver parenchymal cells. As such, the effect of suppressing TG accumulation is also caused in the inhibition of caveolin above or the like. In addition, generally speaking, it is known that an effect of suppressing TG accumulation within cells raises an anti-obesity effect. Therefore, also in the analysis at cell level that uses a human siRNA by inhibiting SMS2, an effect of suppressing liver TG accumulation by knockdown it in a mouse liver as well as an effect that suggests suppression of visceral fat accumulation and suppression of fatty liver could be confirmed.

Example 9

Examples of Nucleic Acids Other than siRNA (a Ribozyme)

Next, using, for example, the method described in Kikuchi, Y. & Sasaki, N., Nucl Acids Res, 1991, 19, 6751, Yo KIKUCHI, Kagaku to Seibutsu [Chemistry and Biology], 1992, 30, 112, based on the nucleic acid sequences of SMS2 set forth in SEQ ID NO: 79 or 80, ribozyme sequences are designed.

These can be confirmed for the effect of the ribozyme of the present invention by the methods described in Examples 7 and 8 which use mice and HepG2 cell.

Example 10

Screening Antisense Nucleic Acids Against SMS2

In the Example, the effectiveness of antisense nucleic acids designed based on a homologous region (a continuous homologous region of 13 mer or more) between human and mouse SMS2 nucleotide sequences was demonstrated.

The antisense oligonucleotides were designed and made, and knockdown experiments in human HEK 293 cell were carried out with them. "Efficient gene silencing by delivery of locked nucleic acid antisense oligonucleotides, unassisted by transfection reagents", Nucleic Acid Research 2010, Vol 38, No. 1 was referred to for designing their sequence structure.

Sequences and forms of 13 mer antisense oligonucleotides used in the Example are shown below. The nucleic acids used were an LNA-containing nucleic acid that is also called as an LNA type Gapmer antisense oligonucleotide. Capital letters mean an LNA (Locked nucleic acid) and lower-case letters mean DNA. LNA is a kind of BNA (Bridged Nucleic Acid). 10 kinds or more of BNAs are known. LNA is an artificial nucleic acid wherein positions 2' and 4' of the sugar are crosslinked with —O—CH$_2$—, thereby its conformation is fixed in N-form and which is available from Funakoshi Corporation or the like. In the oligonucleotides, all nucleic acids are linked via phosphorothioate modified backbone. All Cs in LNA portions are methylcytosines. In the examples below, 3 locked nucleic acids (LNAs) are included at 5' end and 2 locked nucleic acids are included at 3' end.

```
Name  Antisense nucleic acid sequence(5'-3')
                                          (SEQ ID NO: 81)
1     SMS2-13-003 -> TGAtaccaccaGA (SEQ ID NO: 82)
2     SMS2-13-006 -> TGCagatgatcCC (SEQ ID NO: 83)
3     SMS2-13-007 -> CGTgttgtgatAT (SEQ ID NO: 84)
4     SMS2-13-008 -> ACTtgtctgggAG (SEQ ID NO: 85)
5     SMS2-13-009 -> AGAggaagtctCC (SEQ ID NO: 86)
6     SMS2-13-010 -> AGAtggggaacCA (SEQ ID NO: 87)
7     SMS2-13-011 -> AGTctccattgAG (SEQ ID NO: 88)
8     SMS2-13-012 -> CCAgaagtgacGA (SEQ ID NO: 89)
9     SMS2-13-014 -> TTGcctgagagTC (SEQ ID NO: 90)
10    SMS2-13-017 -> AAGttttgctgTC (SEQ ID NO: 91)
11    SMS2-13-019 -> TTGaagcagccAG (SEQ ID NO: 92)
12    SMS2-13-020 -> GCAgcaaggaaTT
```

Using the 12 kinds of LNA type Gapmer antisense oligonucleotides made above, knockdown experiments in human HEK 293 cell were carried out. The LNA type Gapmer antisense oligonucleotide was added in a naked form at a final concentration of 5 micromolar to the cell culture solution. Quantitative PCR carried out 72 hours after transformation were carried out. G3PDH was used as an endogenous control.

As primer sequences used for measuring the expression amount of human SMS2,

```
                                          (SEQ ID NO: 33)
     Fw primer: TCAATGGAGACTCTCAGGC;

(SEQ ID NO: 34)
     Rv primer: CCGCTGAAGAGGAAGTCTC
``` were used, and as primer sequences used for measuring the expression amount of human G3PDH,

```
                                          (SEQ ID NO: 35)
     Fw primer: CCTTCCGTGTCCCCACTG;

(SEQ ID NO: 36)
     Rv primer: ACCCTGTTGCTGTAGCCAA
``` were used.

As a result, the suppression of the gene expression of SMS2 was confirmed in any embodiment with the above oligonucleotides compared to cells to which saline was administered (cells to which antisense was not added) and 50% or more suppression in the gene expression of SMS2 was confirmed with SMS2-13-006, SMS2-13-007, SMS2-13-008, SMS2-13-012, SMS2-13-014, SMS2-13-017 and SMS2-13-019 <SEQ ID NOs: 82, 83, 84, 88, 89, 90 and 91, respectively>compared to cells to which saline was administered (cells to which antisense was not added).

While, as described above, the present invention has been illustrated with preferred embodiments of the present invention, it is understood that the scope of the present invention should be interpreted only by the Claims. It is understood that the content of the patents, patent applications and literatures referred herein should be incorporated herein for reference same as if the content thereof itself is specifically described herein. The present application claims priority to U.S. Provisional Application Ser. No. 61/385,377 that was filed on Sep. 22, 2010. It is understood that the entire content of it is to be incorporated as constituting a part of the present specification in a similar manner to as if it is specifically described herein.

INDUSTRIAL APPLICABILITY

The present invention provides a drug for treating and preventing a metabolic disease.

Sequence Listing Free Text

SEQ ID NO: 1: a sequence of the sense strand portion of the duplex portion of SMS2-i6

SEQ ID NO: 2: a sequence of the antisense strand of the duplex portion of SMS2-i6

SEQ ID NO: 3: a sequence of the sense strand portion of the duplex portion of SMS2-i7

SEQ ID NO: 4: a sequence of the antisense strand of the duplex portion of SMS2-i7

SEQ ID NO: 5: a sequence of the sense strand portion of the duplex portion of SMS2-i8

SEQ ID NO: 6: a sequence of the antisense strand of the duplex portion of SMS2-i8

SEQ ID NO: 7: a sequence of the sense strand portion of the duplex portion of SMS2-i104

SEQ ID NO: 8: a sequence of the antisense strand of the duplex portion of SMS2-i104

SEQ ID NO: 9: a sequence of the sense strand of the duplex portion of SMS2-i105

SEQ ID NO: 10: a sequence of the antisense strand of the duplex portion of SMS2-i105

SEQ ID NO: 11: a sequence of the sense strand of the duplex portion of SMS2-i106

SEQ ID NO: 12: a sequence of the antisense portion of the duplex portion of SMS2-i106

SEQ ID NO: 13: a sequence of the sense strand of the duplex portion of SMS2-i107

SEQ ID NO: 14: a sequence of the antisense strand of the duplex portion of SMS2-i107

SEQ ID NO: 15: a sequence of the sense strand of the duplex portion of SMS2-i108

SEQ ID NO: 16: a sequence of the antisense strand of the duplex portion of SMS2-i108

SEQ ID NO: 17: a sequence of the sense strand of the duplex portion of SMS2-i109

SEQ ID NO: 18: a sequence of the antisense strand of the duplex portion of SMS2-i109

SEQ ID NO: 19: a sequence of the sense strand of the duplex portion of CTR-i

SEQ ID NO: 20: a sequence of the antisense strand of the duplex portion of CTR-i SEQ ID NO: 21: a sequence of the sense strand of the duplex portion of SMS2-i3

SEQ ID NO: 22: a sequence of the antisense strand of the duplex portion of SMS2-i3

SEQ ID NO: 23: a sequence of the sense strand of the duplex portion of SMS2-i11

SEQ ID NO: 24: a sequence of the antisense strand of the duplex portion of SMS2-i11

SEQ ID NO: 25: a Fw primer for adiponectin used in Example 1

SEQ ID NO: 26: a Rv primer for adiponectin used in Example 1

SEQ ID NO: 27: a Fw primer for insulin receptor (IR)

SEQ ID NO: 28: a Rv primer for insulin receptor (IR)

SEQ ID NO: 29: a Fw primer for GLUT4

SEQ ID NO: 30: a Rv primer for GLUT4

SEQ ID NO: 31: a Fw primer for hypoxanthine-guanine phosphoribosyltransferase (HPRT)

SEQ ID NO: 32: a Rv primer for hypoxanthine-guanine phosphoribosyltransferase (HPRT)

SEQ ID NO: 33: a Fw primer for realtime quantitative PCR used for measuring the expression amount of human and mouse SMS2

SEQ ID NO: 34: a Rv primer for realtime quantitative PCR used for measuring the expression amount of human and mouse SMS2

SEQ ID NO: 35: a Fw primer for human G3PDH

SEQ ID NO: 36: a Rv primer for human G3PDH

SEQ ID NO: 37: a Fw primer for mouse G3PDH

SEQ ID NO: 38: a Rv primer for mouse G3PDH

SEQ ID NO: 39: a sequence of the sense strand portion of the duplex portion of SMS2-i1

SEQ ID NO: 40: a sequence of the antisense strand of the duplex portion of SMS2-i1

SEQ ID NO: 41: a sequence of the sense strand portion of the duplex portion of SMS2-i2

SEQ ID NO: 42: a sequence of the antisense strand of the duplex portion of SMS2-i2

SEQ ID NO: 43: a sequence of the sense strand of the duplex portion of SMS2-i4

SEQ ID NO: 44: a sequence of the antisense strand of the duplex portion of SMS2-i4

SEQ ID NO: 45: a sequence of the sense strand of the duplex portion of SMS2-i5

SEQ ID NO: 46: a sequence of the antisense strand of the duplex portion of SMS2-i5

SEQ ID NO: 47: a sequence of the sense strand of SMS2-i6

SEQ ID NO: 48: a sequence of the antisense strand of SMS2-i6

SEQ ID NO: 49: a sequence of the sense strand of SMS2-i7

SEQ ID NO: 50: a sequence of the antisense strand of SMS2-i7

SEQ ID NO: 51: a sequence of the sense strand of SMS2-i8

SEQ ID NO: 52: a sequence of the antisense strand of SMS2-i8

SEQ ID NO: 53: a sequence of the sense strand of SMS2-i104

SEQ ID NO: 54: a sequence of the antisense strand of SMS2-i104

SEQ ID NO: 55: a sequence of the sense strand of SMS2-i105

SEQ ID NO: 56: a sequence of the antisense strand of SMS2-i105

SEQ ID NO: 57: a sequence of the sense strand of SMS2-i106

SEQ ID NO: 58: a sequence of the antisense strand of SMS2-i106

SEQ ID NO: 59: a sequence of the sense strand of SMS2-i107

SEQ ID NO: 60: a sequence of the antisense strand of SMS2-i107

SEQ ID NO: 61: a sequence of the sense strand of SMS2-i108

SEQ ID NO: 62: a sequence of the antisense strand of SMS2-i108

SEQ ID NO: 63: a sequence of the sense strand of SMS2-i109

SEQ ID NO: 64: a sequence of the antisense strand of SMS2-i109

SEQ ID NO: 65: a sequence of the sense strand of CTR-i

SEQ ID NO: 66: a sequence of the antisense strand of CTR-i

SEQ ID NO: 67: a sequence of the sense strand of SMS2-i3

SEQ ID NO: 68: a sequence of the antisense strand of SMS2-i3

SEQ ID NO: 69: a sequence of the sense strand of SMS2-i11

SEQ ID NO: 70: a sequence of the antisense strand of SMS2-i11

SEQ ID NO: 71: a sequence of the sense strand of SMS2-i1

SEQ ID NO: 72: a sequence of the antisense strand of SMS2-i1

SEQ ID NO: 73: a sequence of the sense strand of SMS2-i2

SEQ ID NO: 74: a sequence of the antisense strand of SMS2-i2

SEQ ID NO: 75: a sequence of the sense strand of SMS2-i4

SEQ ID NO: 76: a sequence of the antisense strand of SMS2-i4

SEQ ID NO: 77: a sequence of the sense strand of SMS2-i5

SEQ ID NO: 78: a sequence of the antisense strand of SMS2-i5

SEQ ID NO: 79: a nucleic acid sequence of human SMS2

SEQ ID NO: 80: a nucleic acid sequence of mouse SMS2

SEQ ID NO: 81: a sequence of an SMS2-13-003 antisense nucleic acid used in Example 10

SEQ ID NO: 82: a sequence of an SMS2-13-006 antisense nucleic acid used in Example 10

SEQ ID NO: 83: a sequence of an SMS2-13-007 antisense nucleic acid used in Example 10

SEQ ID NO: 84: a sequence of an SMS2-13-008 antisense nucleic acid used in Example 10

SEQ ID NO: 85: a sequence of an SMS2-13-009 antisense nucleic acid used in Example 10

SEQ ID NO: 86: a sequence of an SMS2-13-010 antisense nucleic acid used in Example 10

SEQ ID NO: 87: a sequence of an SMS2-13-011 antisense nucleic acid used in Example 10

SEQ ID NO: 88: a sequence of an SMS2-13-012 antisense nucleic acid used in Example 10

SEQ ID NO: 89: a sequence of an SMS2-13-014 antisense nucleic acid used in Example 10

SEQ ID NO: 90: a sequence of an SMS2-13-017 antisense nucleic acid used in Example 10

SEQ ID NO: 91: a sequence of an SMS2-13-019 antisense nucleic acid used in Example 10

SEQ ID NO: 92: a sequence of an SMS2-13-020 antisense nucleic acid used in Example 10

The invention claimed is:

1. A pharmaceutical composition for treating or preventing a metabolic syndrome, comprising an siRNA that suppresses the expression of SMS2, wherein said siRNA consists of any one or more siRNAs selected from the group consisting of:

(a) an siRNA wherein one strand of the duplex RNA portion is a base sequence set forth by SEQ ID NO: 1 and the other strand of the duplex RNA portion is a base sequence set forth by SEQ ID NO: 2;

(b) an siRNA wherein one strand of the duplex RNA portion is a base sequence set forth by SEQ ID NO: 3 and the other strand of the duplex RNA portion is a base sequence set forth by SEQ ID NO: 4;

(c) an siRNA wherein one strand of the duplex RNA portion is a base sequence set forth by SEQ ID NO: 7 and the other strand of the duplex RNA portion is a base sequence set forth by SEQ ID NO: 8;

(d) an siRNA wherein one strand of the duplex RNA portion is a base sequence set forth by SEQ ID NO: 9 and the other strand of the duplex RNA portion is a base sequence set forth by SEQ ID NO: 10;
(e) an siRNA wherein one strand of the duplex RNA portion is a base sequence set forth by SEQ ID NO: 11 and the other strand of the duplex RNA portion is a base sequence set forth by SEQ ID NO: 12;
(f) an siRNA wherein one strand of the duplex RNA portion is a base sequence set forth by SEQ ID NO: 13 and the other strand of the duplex RNA portion is a base sequence set forth by SEQ ID NO: 14;
(g) an siRNA wherein one strand of the duplex RNA portion is a base sequence set forth by SEQ ID NO: 15 and the other strand of the duplex RNA portion is a base sequence set forth by SEQ ID NO: 16;
(h) an siRNA wherein one strand of the duplex RNA portion is a base sequence set forth by SEQ ID NO: 21 and the other strand of the duplex RNA portion is a base sequence set forth by SEQ ID NO: 22;
(i) an siRNA wherein one strand of the duplex RNA portion is a base sequence set forth by SEQ ID NO: 23 and the other strand of the duplex RNA portion is a base sequence set forth by SEQ ID NO: 24;
(j) an siRNA wherein one strand of the duplex RNA portion is a base sequence set forth by SEQ ID NO: 39 and the other strand of the duplex RNA portion is a base sequence set forth by SEQ ID NO: 40;
(k) an siRNA wherein one strand of the duplex RNA portion is a base sequence set forth by SEQ ID NO: 45 and the other strand of the duplex RNA portion is a base sequence set forth by SEQ ID NO: 46; and
(l) an siRNA of any one of (a)-(k), wherein one or more nucleotides are added, inserted, deleted or substituted in one or both of the base sequences, said siRNA having an activity of suppressing the expression of SMS2.

2. A pharmaceutical composition for treating or preventing a metabolic syndrome, comprising a nucleic acid that suppresses the expression of SMS2, wherein the sequence of said nucleic acid consists of any one or more of the nucleic acid sequences of SEQ ID NOs: 83, 88, 89 or 90, wherein said nucleic acid comprises at least one locked nucleic acid (LNA) nucleotide.

3. An siRNA selected from the group consisting of:
(a) an siRNA wherein one strand of the duplex RNA portion is a base sequence set forth by SEQ ID NO: 1 and the other strand of the duplex RNA portion is a base sequence set forth by SEQ ID NO: 2;
(b) an siRNA wherein one strand of the duplex RNA portion is a base sequence set forth by SEQ ID NO: 3 and the other strand of the duplex RNA portion is a base sequence set forth by SEQ ID NO: 4;
(c) an siRNA wherein one strand of the duplex RNA portion is a base sequence set forth by SEQ ID NO: 7 and the other strand of the duplex RNA portion is a base sequence set forth by SEQ ID NO: 8;
(d) an siRNA wherein one strand of the duplex RNA portion is a base sequence set forth by SEQ ID NO: 9 and the other strand of the duplex RNA portion is a base sequence set forth by SEQ ID NO: 10;
(e) an siRNA wherein one strand of the duplex RNA portion is a base sequence set forth by SEQ ID NO: 11 and the other strand of the duplex RNA portion is a base sequence set forth by SEQ ID NO: 12;
(f) an siRNA wherein one strand of the duplex RNA portion is a base sequence set forth by SEQ ID NO: 13 and the other strand of the duplex RNA portion is a base sequence set forth by SEQ ID NO: 14;
(g) an siRNA wherein one strand of the duplex RNA portion is a base sequence set forth by SEQ ID NO: 15 and the other strand of the duplex RNA portion is a base sequence set forth by SEQ ID NO: 16;
(h) an siRNA wherein one strand of the duplex RNA portion is a base sequence set forth by SEQ ID NO: 21 and the other strand of the duplex RNA portion is a base sequence set forth by SEQ ID NO: 22;
(i) an siRNA wherein one strand of the duplex RNA portion is a base sequence set forth by SEQ ID NO: 23 and the other strand of the duplex RNA portion is a base sequence set forth by SEQ ID NO: 24;
(j) an siRNA wherein one strand of the duplex RNA portion is a base sequence set forth by SEQ ID NO: 39 and the other strand of the duplex RNA portion is a base sequence set forth by SEQ ID NO: 40;
(k) an siRNA wherein one strand of the duplex RNA portion is a base sequence set forth by SEQ ID NO: 45 and the other strand of the duplex RNA portion is a base sequence set forth by SEQ ID NO: 46; and
(l) an siRNA of any of (a)-(k), wherein one or more nucleotides are added, inserted, deleted or substituted in one or both of the base sequences, said siRNA having an activity of suppressing the expression of SMS2.

4. A locked nucleic acid (LNA)-containing nucleic acid, wherein the sequence of said LNA-containing nucleic acid consists of any one or more of the nucleic acid sequences of SEQ ID NOs: 81-91 or 92.

5. A method for treating or preventing a metabolic syndrome, said method comprising administering a pharmaceutical composition to a subject in need thereof in an effective amount to treat or prevent said metabolic syndrome, wherein said pharmaceutical composition comprises an siRNA that suppresses the expression of SMS2.

6. The method according to claim 5, wherein said metabolic syndrome is one or more selected from the group consisting of obesity, diabetes, dyslipidemia and fatty liver.

7. A method for treating or preventing a metabolic syndrome, said method comprising administering an siRNA that suppresses the expression of SMS2 to a subject in need thereof in an effective amount to treat or prevent said metabolic syndrome.

8. The method according to claim 7, wherein said metabolic syndrome is one or more selected from the group consisting of obesity, diabetes, dyslipidemia and fatty liver.

9. A method for treating or preventing a metabolic syndrome, said method comprising administering a locked nucleic acid (LNA)-containing nucleic acid that suppresses the expression of SMS2 to a subject in need thereof in an effective amount to treat or prevent said metabolic syndrome.

10. The method according to claim 9, wherein said metabolic syndrome is one or more selected from the group consisting of obesity, diabetes, dyslipidemia and fatty liver.

11. A method for treating or preventing a metabolic syndrome, said method comprising administering an siRNA that suppresses the expression of SMS2 to a subject in need thereof in an effective amount to treat or prevent said metabolic syndrome, wherein said siRNA consists of any one or more siRNAs selected from the group consisting of:
(a) an siRNA wherein one strand of the duplex RNA portion is a base sequence set forth by SEQ ID NO: 1 and the other strand of the duplex RNA portion is a base sequence set forth by SEQ ID NO: 2;
(b) an siRNA wherein one strand of the duplex RNA portion is a base sequence set forth by SEQ ID NO: 3 and the other strand of the duplex RNA portion is a base sequence set forth by SEQ ID NO: 4;

(c) an siRNA wherein one strand of the duplex RNA portion is a base sequence set forth by SEQ ID NO: 5 and the other strand of the duplex RNA portion is a base sequence set forth by SEQ ID NO: 6;

(d) an siRNA wherein one strand of the duplex RNA portion is a base sequence set forth by SEQ ID NO: 7 and the other strand of the duplex RNA portion is a base sequence set forth by SEQ ID NO: 8;

(e) an siRNA wherein one strand of the duplex RNA portion is a base sequence set forth by SEQ ID NO: 9 and the other strand of the duplex RNA portion is a base sequence set forth by SEQ ID NO: 10;

(f) an siRNA wherein one strand of the duplex RNA portion is a base sequence set forth by SEQ ID NO: 11 and the other strand of the duplex RNA portion is a base sequence set forth by SEQ ID NO: 12;

(g) an siRNA wherein one strand of the duplex RNA portion is a base sequence set forth by SEQ ID NO: 13 and the other strand of the duplex RNA portion is a base sequence set forth by SEQ ID NO: 14;

(h) an siRNA wherein one strand of the duplex RNA portion is a base sequence set forth by SEQ ID NO: 15 and the other strand of the duplex RNA portion is a base sequence set forth by SEQ ID NO: 16;

(i) an siRNA wherein one strand of the duplex RNA portion is a base sequence set forth by SEQ ID NO: 17 and the other strand of the duplex RNA portion is a base sequence set forth by SEQ ID NO: 18;

(j) an siRNA wherein one strand of the duplex RNA portion is a base sequence set forth by SEQ ID NO: 21 and the other strand of the duplex RNA portion is a base sequence set forth by SEQ ID NO: 22;

(k) an siRNA wherein one strand of the duplex RNA portion is a base sequence set forth by SEQ ID NO: 23 and the other strand of the duplex RNA portion is a base sequence set forth by SEQ ID NO: 24;

(l) an siRNA wherein one strand of the duplex RNA portion is a base sequence set forth by SEQ ID NO: 39 and the other strand of the duplex RNA portion is a base sequence set forth by SEQ ID NO: 40;

(m) an siRNA wherein one strand of the duplex RNA portion is a base sequence set forth by SEQ ID NO: 41 and the other strand of the duplex RNA portion is a base sequence set forth by SEQ ID NO: 42;

(n) an siRNA wherein one strand of the duplex RNA portion is a base sequence set forth by SEQ ID NO: 45 and the other strand of the duplex RNA portion is a base sequence set forth by SEQ ID NO: 46; and (o) an siRNA of any of (a)-(n), wherein one or more nucleotides are added, inserted, deleted or substituted in one or both of the base sequences, said siRNA having an activity of suppressing the expression of SMS2.

12. A method for treating or preventing a metabolic syndrome, said method comprising administering a locked nucleic acid (LNA)-containing nucleic acid that suppresses the expression of SMS2 to a subject in need thereof in an effective amount to treat or prevent said metabolic syndrome, wherein the sequence of said LNA-containing nucleic acid consists of any one or more of the nucleic acid sequences of SEQ ID NOs: 81-91 or 92.

13. The method according to claim 11 or 12, wherein said metabolic syndrome is one or more selected from the group consisting of obesity, diabetes, dyslipidemia and fatty liver.

* * * * *